United States Patent
Ghosh et al.

(10) Patent No.: US 7,157,489 B2
(45) Date of Patent: Jan. 2, 2007

(54) HIV PROTEASE INHIBITORS

(75) Inventors: Arun K. Ghosh, River Forest, IL (US);
Geoffrey M. Bilcer, Chicago, IL (US);
Thippeswamy Devasamudram, Chicago, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 242 days.

(21) Appl. No.: 10/382,435

(22) Filed: Mar. 6, 2003

(65) Prior Publication Data

US 2004/0039016 A1 Feb. 26, 2004

Related U.S. Application Data

(60) Provisional application No. 60/433,627, filed on Dec. 13, 2002, provisional application No. 60/363,628, filed on Mar. 12, 2002.

(51) Int. Cl.
*C07D 493/04* (2006.01)
*C07D 493/10* (2006.01)
*A61K 31/401* (2006.01)
*C07D 307/93* (2006.01)

(52) U.S. Cl. ............ 514/422; 514/459; 514/460; 514/469; 548/525; 549/415; 549/465

(58) Field of Classification Search ........... 549/415, 549/465; 548/525; 514/422, 459, 460, 469
See application file for complete search history.

(56) References Cited

U.S. PATENT DOCUMENTS

| | | | |
|---|---|---|---|
| 5,196,438 A | 3/1993 | Martin et al. | |
| 5,475,027 A | 12/1995 | Talley et al. | |
| 5,502,060 A | 3/1996 | Thompson et al. | |
| 5,585,357 A | 12/1996 | Dolle et al. | |
| 5,585,397 A * | 12/1996 | Tung et al. | 514/473 |
| 5,691,372 A | 11/1997 | Tung et al. | |
| 5,703,076 A | 12/1997 | Talley et al. | |
| 5,705,500 A | 1/1998 | Getman et al. | |
| 5,723,490 A | 3/1998 | Tung | |
| 5,728,718 A | 3/1998 | Randad et al. | |
| 5,753,660 A | 5/1998 | Sikorski et al. | |
| 5,843,946 A | 12/1998 | Vazquez et al. | |
| 5,968,942 A | 10/1999 | Vazquez et al. | |
| 5,990,155 A | 11/1999 | Tung et al. | |
| 6,008,228 A | 12/1999 | Bailey et al. | |
| 6,060,476 A | 5/2000 | Vazquez et al. | |
| 6,100,277 A | 8/2000 | Tucker et al. | |
| 6,245,806 B1 | 6/2001 | Dombrowski et al. | |
| 6,248,775 B1 | 6/2001 | Vazquez et al. | |
| 6,319,946 B1 | 11/2001 | Hale et al. | |

FOREIGN PATENT DOCUMENTS

| | | |
|---|---|---|
| EP | 0 715 618 | 6/1996 |
| EP | 1 136 479 | 9/2001 |
| WO | WO 94/04492 | 3/1994 |
| WO | WO 94/14793 | 7/1994 |
| WO | WO 95/06030 | 3/1995 |
| WO | WO 96/28463 | 9/1996 |
| WO | WO 96/33184 | 10/1996 |
| WO | WO 97/19055 | 5/1997 |
| WO | WO 99/65870 | 12/1999 |
| WO | WO 99/67254 | 12/1999 |
| WO | WO 01/25240 | 4/2001 |
| WO | WO 02/081478 | 10/2002 |
| WO | WO 02/083657 | 10/2002 |
| WO | WO 02/092595 | 11/2002 |

OTHER PUBLICATIONS van Heeswijk et al., PubMed Abstract (Antivir Ther. 6(4):201-29), Dec. 2001.*
Marcus et al., PubMed Abstract (Intervirology, 45(4-6):260-6), 2002.*
Miles, Medline Abstract (Community Pract, vol. 78, Issue 8, pp. 292-294) Aug. 2005.*
Ghosh et al., *Bioorganic & Medicinal Chemistry Letters 8*, pp. 687-690 (1998).
Ghosh et al., *J. Med. Chem.*, 39, pp. 3278-3290 (1996).
Beaulieu et al., *J. Med. Chem.*, 43, pp. 1094-1108 (2000).
P. Spradling et al., *Clinical Infectious Diseases*, 35(9), 1106-1112 (2002).

* cited by examiner

*Primary Examiner*—Deepak Rao
(74) *Attorney, Agent, or Firm*—Marshall, Gerstein & Borun LLP

(57) ABSTRACT

Compounds useful for inhibiting HIV protease are disclosed. Methods of making the compounds, and their use as therapeutic agents, for example, in treating wild-type HIV and of multidrug-resistant strains of HIV, also are disclosed.

19 Claims, No Drawings

HIV PROTEASE INHIBITORS

CROSS-REFERENCE TO RELATED APPLICATIONS

This application claims the benefit of provisional U.S. Patent Application Ser. No. 60/363,628, filed Mar. 12, 2002 and provisional U.S. Patent Application Ser. No. 60/433, 627, filed Dec. 13, 2002.

STATEMENT OF GOVERNMENTAL INTEREST

This invention was made with Government support under contract GM53386 awarded by the National Institutes of Health. The Government has certain rights in this invention.

FIELD OF THE INVENTION

The present invention relates to compounds useful for inhibiting HIV protease enzymes. More particularly, the present invention relates to HIV protease inhibitors, methods of manufacturing the inhibitors, and their use as therapeutic agents, for example, in treating wild-type HIV and multidrug-resistant strains of HIV.

BACKGROUND OF THE INVENTION

It is well known that a wide range of diseases are caused by retroviruses As presently understood, acquired immunodeficiency syndrome (AIDS) is a disease of the immune system caused by the retrovirus HIV (Human Immunodeficiency Virus). According to estimates from the World Health Organization, AIDS affects millions of people and is continuing to spread. In virtually all cases, AIDS results in death of the infected individual.

Retroviruses HIV-1 and HIV-2 have been identified as a cause of AIDS. A retroviral protease is a proteolytic enzyme that participates in the maturation of new infectious virions in infected cells during the reproductive cycle. In a number of retroviruses, for example, HIV-1 and HIV-2, each have a region in their genome that codes for a "gag-protease." The "gag-protease" is responsible for the correct proteolytic cleavage of the precursor proteins that are produced from the genome regions coding for the "Group Specific Antigens" (gag).

The "gag-protease" cleaves the major core protein p24 of HIV-1 and HIV-2 preferentially N-terminally of proline residues, for example, in the divalent residues Phe-Pro, Leu-Pro, or Tyr-Pro. It is a protease having a catalytically active aspartate residue in the active center, i.e., an aspartate protease. During cleavage, the structural proteins of the virus core are liberated. The "gag-protease" itself is a component of a precursor protein encoded by the pol-genome region of HIV-1 and HIV-2, which also contain regions for the "reverse transcriptase" and "integrase" and is thought to be cleaved by autoproteolysis.

Retroviral protease is a critical enzyme in the retroviral replication process. Propagation of a retrovirus, such as HIV, can be impeded by exposing the virus to a retroviral protease inhibitor. As used herein, protease inhibitor refers to compounds that inhibit proteases of viral origin, and that are useful in the prophylaxis or treatment of viral infections caused by retroviruses, such as HIV, in mammals, both human and nonhuman. Protease inhibitors perform at the final stage of viral replication, and prevent HIV from making new copies of itself by interfering with the HIV protease enzyme. As a result, the new copies of HIV are not able to infect new cells.

Retroviral protease inhibition typically involves a transition-state mimetic whereby the retroviral protease is exposed to a compound that binds, typically in a reversible manner, to the enzyme in competition with the gag and gag-pol proteins to inhibit specific processing of structural proteins and the release of retroviral protease itself. In this manner, retroviral replication proteases can be effectively inhibited.

Several classes of compounds for inhibition of proteases, including HIV protease, have been proposed. Such compounds include hydroxyethylamine isosteres, reduced amide isosteres, and nonpeptide isosteres. See, for example, EP 0 346 847; EP 0 342 541; Roberts et al., "Rational Design of Peptide-Based Proteinase Inhibitors," Science, 248, 358 (1990); Erickson et al., "Design Activity, and 2.8 Å Crystal Structure of a C2 Symmetric Inhibitor Complexed to HIV-1 Protease," Science, 249, 527 (1990); and S. Thaisrivongs, "Structure-Based Design of Non-Peptide HIV Protease Inhibitors," 35th Annual Buffalo Medicinal Chemistry Meeting, State University of New York at Buffalo, Buffalo, N.Y., May, 1994. Also, see, for example, U.S. Pat. Nos. 6,008,228; 6,100,277; and 6,245,806.

Some antiviral compounds that act as inhibitors of HIV replication are effective agents in the treatment of AIDS and similar diseases, e.g., azidothymidine or AZT. WO 99/67254 contains a discussion of AIDS and HIV protease inhibitors, and is incorporated herein by reference. However, a typical problem associated with retroviral protease inhibitors, like HIV protease inhibitors, has been the development of strains of the virus resistant to the inhibitor. The present invention provides nonpeptidic compounds that are effective inhibitors of HIV protease, and are useful in the treatment of AIDS or HIV infections, including multidrug-resistant strains of HIV.

SUMMARY OF THE INVENTION

The present invention is directed to a novel class of highly potent HIV protease inhibitors. This class of compounds is useful in the treatment of HIV infection. Protease inhibitors of this new class of compounds have been synthesized and tested for efficacy.

Compounds of the present invention have a general structural formula (I):

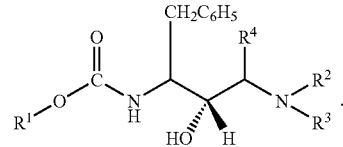

These compounds include, but are not limited to, those having the following structural components: (a) compounds containing a lactam at $R^3$, including 5-, 6-, and 7-membered lactams; (b) compounds containing an extension of the $R^3$ lactam via a fused or spirocyclic ring system, especially systems containing basic amine substituents and hydroxymethyl substituents for increased binding affinity for HIV protease; (c) compounds containing various $R^2$ groups, including isobutyl, lactams, urethanes, furans, pyrans, pyrrolidines, and piperidines, as well as fused or spirocyclic ring systems extending from the above-mentioned moieties at the $R^2$ position; (d) compounds having an $R^1$ group such as bistetrahydrofuran or a fused cyclopentyl tetrahydrofuran, as well as other bicyclic ring systems disclosed herein. A judicious selection of $R^1$, $R^2$, $R^3$, and $R^4$ groups provides compounds having excellent inhibitor properties including in vitro potency, in vivo potency, and oral bioavailability.

One aspect of the present invention is to provide compounds having a structural formula (I)

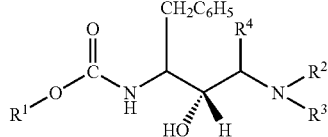

wherein $R^1$ is selected from the group consisting of $C_{1-6}$alkyl, aryl, $C_{1-3}$alkyleneheteroaryl,

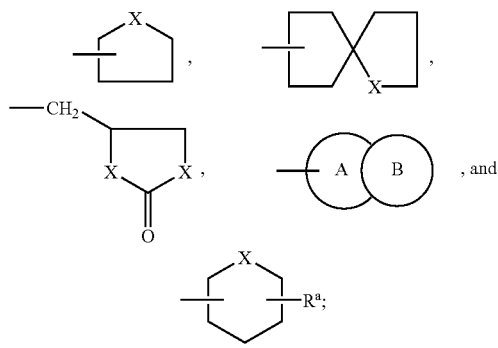

$R^2$ is selected from the group consisting of $C_{1-6}$alkyl, $C_{2-6}$alkenyl, $C_{1-3}$alkyleneN(R$^e$)$_2$, heterocycloalkyl, —NH$_2$, —NHBoc, $C_{1-3}$alkyleneheterocycloalkyl,

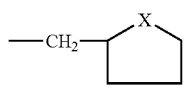

optionally substituted with oxo(=O),

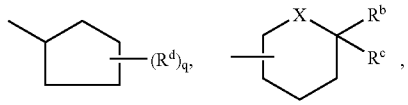

optionally substituted with oxo,

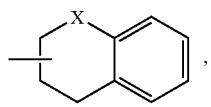

optionally substituted with oxo,

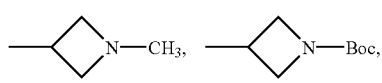

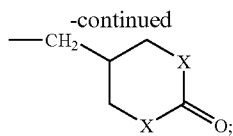

$R^3$ is selected from the group consisting of

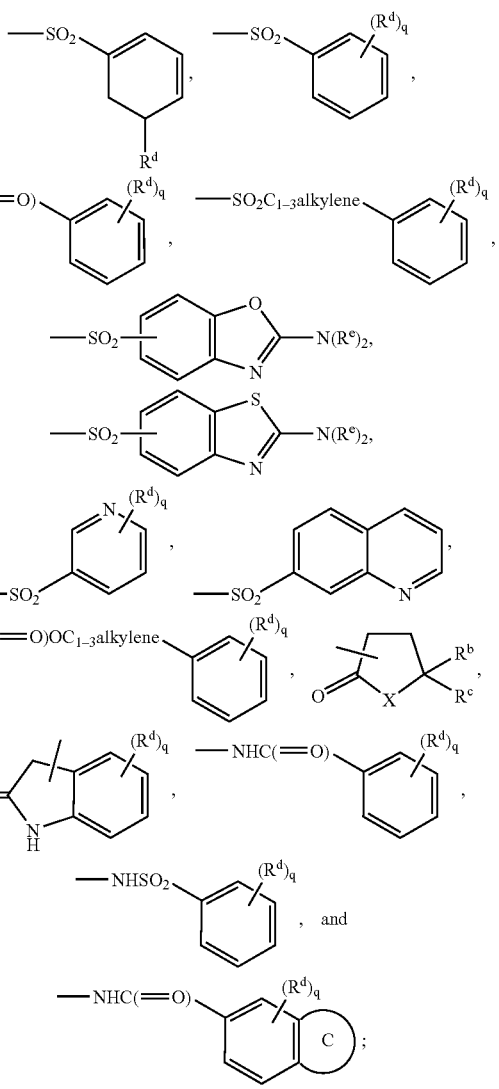

or $R^2$ and $R^3$ are taken together to form either an optionally substituted monocyclic or bicyclic aliphatic ring system, or an optionally substituted macrocyclic ring system containing twelve to twenty atoms, including one to three heteroatoms selected from oxygen, nitrogen, and sulfur;

$R^4$ is selected from the group consisting of hydro and $C_{1-3}$alkyleneheterocycloalkyl optionally substituted with C(=O)aryl or $C_{1-3}$alkylenearyl;

X is selected from the group consisting of O, NR$^e$, S, SO, and SO$_2$;

A and B, independently, are a five-, six-, or seven-membered aliphatic ring, wherein at least one ring contains one or two of the moiety X;

C is a five- or six-membered aliphatic ring containing one to three of the moiety X, and optionally substituted with oxo;

$R^a$ is a five- or six-membered aliphatic ring containing one or two of the moiety X;

$R^b$ and $R^c$, independently, are selected from the group consisting of hydro, OH, $C_{1-3}$alkyl, $C_{1-3}$alkyleneOH, and $C_{1-3}$alkyleneN$(R^e)_2$, or $R^b$ and $R^c$ are taken together to form a five-, six-, or seven-membered aliphatic ring optionally containing one or two of the moiety X;

$R^d$ is selected from the group consisting of $C_{1-4}$alkyl, $C_{2-6}$alkenyl, $C_{1-3}$alkyleneC$_{3-8}$heterocycloalkyl, $OR^e$, $C_{1-3}$alkyleneOR$^e$, N$(R^e)_2$, SR$^e$, halo, nitro, CHO, cyano, NC, C(=O)R$^e$, OC(=O)R$^e$, C(=O)OR$^e$, C(=O)—N$(R^e)_2$, CH=NOH, CH=CHCH$_2$OH, N$(R^e)$COR$^e$, and $C_{1-3}$alkyleneN$(R^e)_2$, or two $R^d$ groups are taken together to form a five-, six-, or seven-membered aliphatic ring optionally containing one or two of the moiety X;

$R^e$ is selected from the group consisting of hydro, $C_{1-6}$alkyl, $C_{2-6}$alkenyl, aryl, heteroaryl, $C_{3-8}$cycloalkyl, THP, Ts, Boc, and $C_{3-8}$heterocycloalkyl;

q is 0 through 3;

and pharmaceutically acceptable salts, prodrugs, or solvates thereof.

Another aspect of the present invention is to provide a potent HIV protease inhibitor useful in the treatment of HIV and AIDS, particularly in the treatment of wild-type HIV and multidrug-resistant strains of HIV. The compounds of structural formula (I) have demonstrated significant HIV protease inhibition activity.

Another aspect of the present invention is to provide a method of treating mammalian HIV infections using a retroviral protease inhibitor which is effective in preventing the replication of retroviruses in vitro or in vivo. A present protease inhibitor can be used alone, or in combination with (a) a second protease inhibitor, (b) another antiviral agent, or (c) both (a) and (b).

Still another aspect of the present invention is to provide pharmaceutical compositions containing one or more compounds of structural formula (I), to use of the compounds and compositions containing the compounds in the therapeutic treatment of a disease or disorder, and to methods of preparing the compounds of structural formula (I) and intermediates involved in the synthesis thereof.

Yet another aspect of the present invention is to provide a method of inhibiting the protease of a multidrug-resistant retrovirus in a mammal infected with the retrovirus, said method comprising administering a therapeutically effective amount of one or more compounds of structural formula (I) to the mammal to inhibit proliferation of the retrovirus.

Another aspect of the present invention is to provide a kit for the treatment of HIV or AIDS comprising a compound of structural formula (I), or a composition containing the same, packaged with instructions for administration of the compound or composition to treat HIV or AIDS.

Yet another aspect of the present invention is to provide an article of manufacture for human pharmaceutical use, comprising (a) a package insert, (b) a container, and either (c1) a packaged composition comprising a compound of structural formula (I) and a second pharmaceutical drug or (c2) a packaged composition comprising a compound of structural formula (I) and a packaged composition comprising a second pharmaceutical drug. The second pharmaceutical drug typically is useful in the treatment of HIV or AIDS.

The above and other aspects and advantages of the present invention are set forth in the following detailed description of the preferred embodiments.

DETAILED DESCRIPTION OF THE PREFERRED EMBODIMENTS

Retroviral protease is a critical enzyme in the retroviral replication process. Propagation of a retrovirus, such as HIV, can be impeded by exposing the virus to a retroviral protease inhibitor. The present invention is directed to compounds of structural formula (I), the inhibition of HIV protease, the prevention or treatment of infection by HIV, and the treatment of AIDS. In particular, the present invention is directed to compounds that treat multidrug-resistant strains of HIV.

Several protease inhibitors currently are available commercially, including saquinavir (also known as INVIRASE®, FORTOVASE®, and Ro31-8959), nelfinavir (also known as VIRACEPT®), amprenavir (also known as AGENERASE®, VX-478, and 141W94), indinavir (also known as CRIXIVAN®, L-735,524, and MK-639), ritonavir (also known as NORVIR®, and ABT-538), and lopinavir (also known as ALUVIRAN® and ABT-378). All of the above compounds suffer from an inability to treat multidrug-resistant strains of HIV.

The compounds of structural formula (I) are defined as follows:

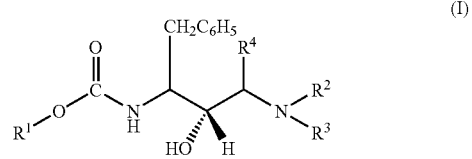

wherein $R^1$ is selected from the group consisting of $C_{1-6}$alkyl, aryl, $C_{1-3}$alkyleneheteroaryl,

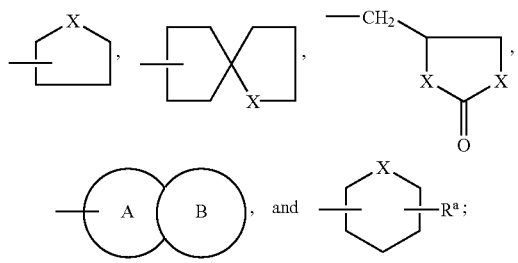

$R^2$ is selected from the group consisting of $C_{1-6}$alkyl, $C_{2-6}$alkenyl, $C_{1-3}$alkyleneN$(R^e)_2$, heterocycloalkyl, NH$_2$, NHBoc, $C_{1-3}$alkyleneheterocycloalkyl,

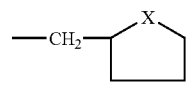

optionally substituted with oxo(=O),

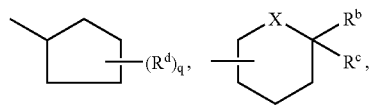

optionally substituted with oxo,

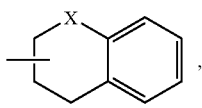

optionally substituted with oxo,

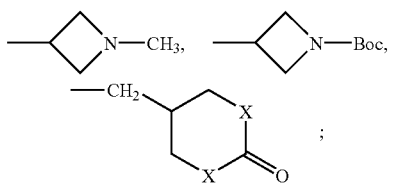

R³ is selected from the group consisting of

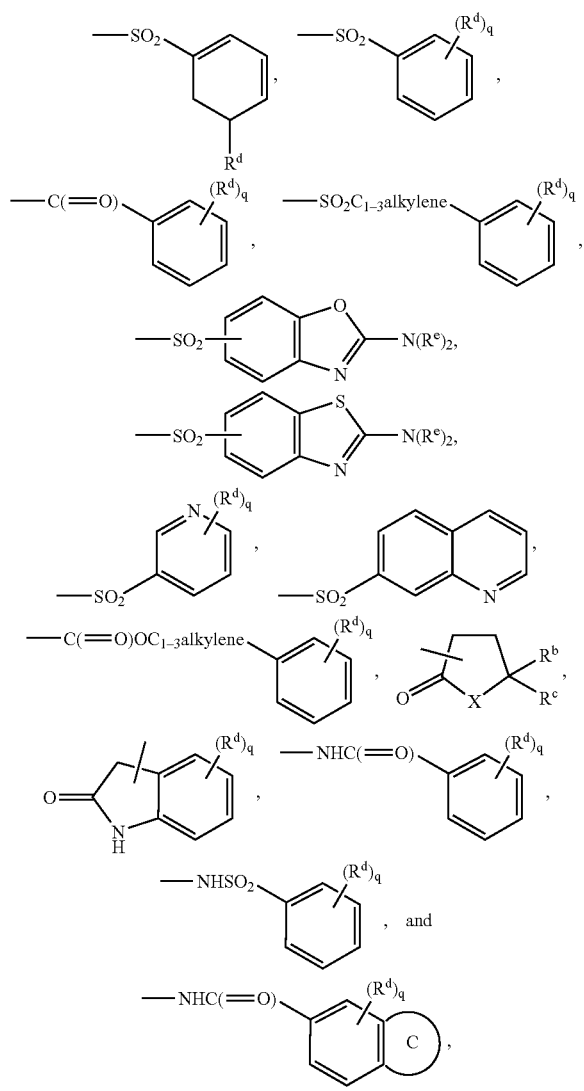

or R² and R³ are taken together to form either an optionally substituted monocyclic or bicyclic aliphatic ring system, or an optionally substituted macrocyclic ring system containing twelve to twenty atoms, including one to three heteroatoms selected from oxygen, nitrogen, and sulfur;

R⁴ is selected from the group consisting of hydro and C₁₋₃alkyleneheterocycloalkyl optionally substituted with C(=O)aryl or C₁₋₃alkylenearyl;

X is selected from the group consisting of O, NRᵉ, and S; SO, and SO₂;

A and B, independently, are five-, six-, or seven-membered aliphatic ring, wherein at least one ring contains one or two of the moiety X;

C is a five- or six-membered aliphatic ring containing one to three of the moiety X, and optionally substituted with oxo;

Rᵃ is a five- or six-membered aliphatic ring containing one or two of the moiety X;

Rᵇ and Rᶜ, independently, are selected from the group consisting of hydro, OH, C₁₋₃alkyl, C₁₋₃alkyleneOH, and C₁₋₃alkyleneN(Rᵉ)₂, or Rᵇ and Rᶜ are taken together to form a five-, six-, or seven-membered aliphatic ring optionally containing one or two of the moiety X;

Rᵈ is selected from the group consisting of C₁₋₄alkyl, C₂₋₆alkenyl, C₁₋₃alkyleneC₃₋₈heterocycloalkyl, ORᵉ, C₁₋₃alkyleneORᵉ, N(Rᵉ)₂, SRᵉ, halo, nitro, CHO, cyano, NC, C(=O)Rᵉ, OC(=O)Rᵉ, C(=O)ORᵉ, C(=O)—N(Rᵉ)₂, CH=NOH, CH=CHCH₂OH, N(Rᵉ)CORᵉ, and C₁₋₃alkyleneN(Rᵉ)₂, or two Rᵈ groups are taken together to form a five-, six-, or seven-membered aliphatic ring optionally containing one or two of the moiety X;

Rᵉ is selected from the group consisting of hydro, C₁₋₆alkyl, C₂₋₆alkenyl, aryl, heteroaryl, C₃₋₈cycloalkyl, THP, Ts, Boc, and C₃₋₈heterocycloalkyl;

q is 0 through 3;

and pharmaceutically acceptable salts, solvates, or prodrugs thereof.

The present invention also is directed to pharmaceutical compositions useful for inhibiting HIV protease, said compositions comprising a compound of structural formula (I) and a pharmaceutically acceptable carrier. These pharmaceutical compositions are useful for treating infection by HIV, or for treating AIDS or ARC. The present invention also is directed to methods of inhibiting HIV protease, methods of treating infection by HIV, and methods of treating AIDS or ARC comprising administration of a therapeutically effective amount of a compound of structural formula (I) or a composition containing a compound of structural formula (I) to an individual in need thereof.

Additionally, the present invention is directed to a pharmaceutical composition comprising a compound of structural formula (I) and an AIDS treatment agent selected from the group consisting of (a) an AIDS antiviral agent, (b) an antiinfective agent, (c) an immunomodulator, and (d) mixtures thereof. The compound of structural formula (I) and the AIDS treatment agent can be packaged separately or together, and administered simultaneously or sequentially.

In preferred embodiments of a compound of structural formula (I), R¹ is selected from the group consisting of

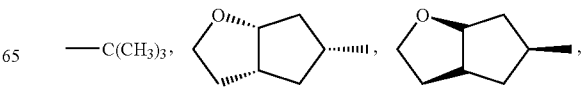

-continued

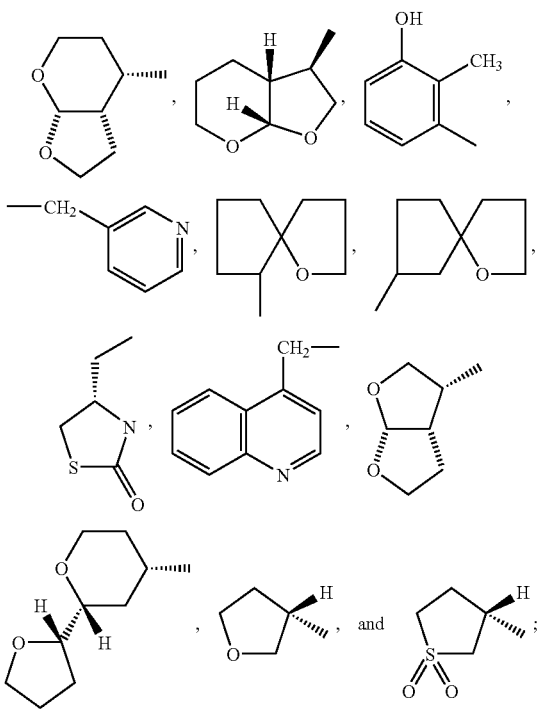

$R^2$ is selected from the group consisting of —CH$_2$CH(CH$_3$)$_2$, —NH$_2$, —NHBoc, —(CH$_2$)$_3$CH=CH$_2$, —(CH$_2$)$_4$—CH=CH$_2$,

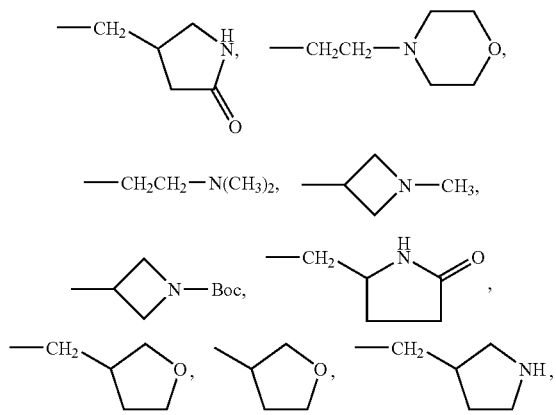

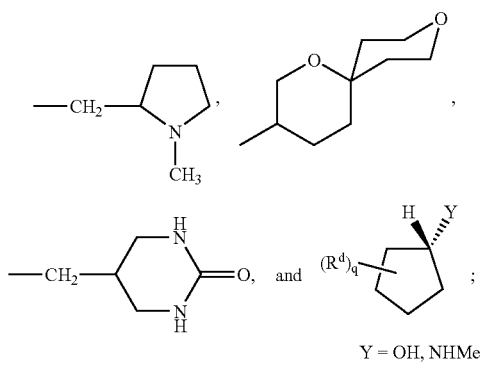

Y = OH, NHMe $R^3$ is selected from the group consisting of

[structures of $R^3$ groups shown on right side of page]

or $R^2$ and $R^3$ are taken together, with the nitrogen atom to which they are attached, to form

[decahydroisoquinoline structure]

optionally substituted with C(=O)NHC$_{1-6}$alkyl, or a macrocyclic ring system containing 16 to 20 carbon atoms, optionally including SO$_2$, oxygen atoms, or both, and optionally substituted with one or more phenyl, benzyl, oxo(=O), and OR$^e$;

$R^4$ is hydro;

$R^b$ and $R^c$, independently, are hydro or C$_{1-3}$alkyl, or are taken together to form (—CH$_2$—)$_4$.

and R$^d$ is selected from the group consisting of C$_{1-3}$alkyleneOR$^e$, N(R$^e$)$_2$, C$_{1-3}$alkyl, halo, nitro, C$_{1-3}$alkyleneC$_{3-8}$heterocycloalkyl, CHO, CH=NOH, and OR$^e$, or two R$^d$ groups are taken together with the carbons to which they are attached to form

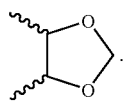

As used herein, the term "alkyl" includes straight chained and branched hydrocarbon groups containing the indicated number of carbon atoms. The hydrocarbon group can contain 1 to 20 carbon atoms, typically methyl, ethyl, and straight-chain and branched propyl and butyl groups. The term "alkyl" includes "bridged alkyl," i.e., a $C_{6-16}$ bicyclic or polycyclic hydrocarbon group, for example, norbornyl, adamantyl, bicyclo[2.2.2]octyl, bicyclo[2.2.1]heptyl, bicyclo[3.2.1]octyl, or decahydronaphthyl. Alkyl groups can be substituted, for example, with hydroxy (OH), halogen, aryl, heteroaryl, heterocycloalkyl, amino ($N(R^e)_2$) groups, and sulfonyl ($SO_2R^e$) groups.

The term "alkenyl" is defined similarly as alkyl, except an alkenyl group contains at least one carbon-carbon double bond.

The term "alkylene" is defined as an alkyl group having a substituent. For example, the term "$C_{1-3}$alkyleneOH" refers to an alkyl group containing one to three carbon atoms and substituted with a hydroxy group.

The term "cycloalkyl" is defined as a cyclic $C_{3-8}$ hydrocarbon group, e.g., cyclopropyl, cyclobutyl, cyclohexyl, and cyclopentyl. "Heterocycloalkyl" is defined similarly as cycloalkyl except the ring contains one to three heteroatoms selected from the group consisting of oxygen, nitrogen, and sulfur. Cycloalkyl and heterocycloalkyl groups can be saturated or partially unsaturated ring systems substituted with, for example, one to three groups, independently selected from $C_{1-4}$alkyl, $C_{1-3}$alkyleneOH, C(=O)$NH_2$, $NH_2$, oxo (=O), aryl, trifluoroethanoyl, and OH.

The term "macrocyclic" is defined as an optionally substituted ring system containing ten to twenty atoms, optionally including up to four heteroatoms selected from oxygen, sulfur, SO, $SO_2$, and $N(R^e)$. Atoms present in an aryl or heteroaryl ring can contribute to the atoms of the macrocyclic ring.

The term "halo" or "halogen" is defined herein to include fluorine, bromine, chlorine, and iodine.

The term "aryl," alone or in combination, is defined as a monocyclic or polycyclic aromatic group, preferably a monocyclic or bicyclic aromatic group, e.g., phenyl or naphthyl. Unless otherwise indicated, an "aryl" group can be unsubstituted or substituted, for example, with one or more, and in particular one to four, halo, CH=NOH, $C_{1-6}$alkyl, $C_{2-6}$alkenyl, $OCF_3$, $NO_2$, CN, NC, $N(R)_2$, OR, $CO_2R$, C(O)N(R)$_2$, C(O)R, $N(R^a)COR^b$, $N(R^a)C(O)OR$, $C_{1-3}$alkyleneOR, and SR, wherein R is selected from the group consisting of hydro, $C_{1-6}$alkyl, $C_{2-6}$alkenyl, cycloalkyl, heterocycloalkyl, aryl, heteroaryl, $SO_2R^e$, OTs, NHBoc, OTHP, and $C_{1-6}$alkyl substituted with halo, hydroxy, aryl, heteroaryl, heterocycloalkyl, $N(R^e)_2$, or $SO_2R^e$, and $R^e$ is as previously defined. Exemplary aryl groups include phenyl, naphthyl, tetrahydronaphthyl, chlorophenyl, methylphenyl, methoxyphenyl, trifluoromethylphenyl, nitrophenyl, hydroxyphenyl, and the like. The terms "aryl$C_{1-3}$alkyl" and "heteroaryl$C_{1-3}$alkyl" are defined as an aryl or heteroaryl group having a $C_{1-3}$alkyl substituent.

The term "heteroaryl" is defined herein as a monocyclic or bicyclic ring system containing one or two aromatic rings and containing at least one nitrogen, oxygen, or sulfur atom in an aromatic ring, and which can be unsubstituted or substituted, for example, with one or more, and in particular one to four, substituents, for example, hydrogen, $C_{1-6}$alkyl, $C_{1-6}$alkoxy, aryl, $N(R^e)_2$, $OR^e$, and halo, wherein $R^e$ is as previously defined. Examples of heteroaryl groups include, but are not limited to, thienyl, furyl, pyridyl, oxazolyl, quinolyl, isoquinolyl, indolyl, triazolyl, isothiazolyl, isoxazolyl, imidizolyl, benzothiazolyl, pyrazinyl, pyrimidinyl, thiazolyl, and thiadiazolyl.

The term "hydroxy" is defined as —OH.
The term "Boc" is defined as t-butoxycarbonyl.
The term "THP" is defined as tetrahydropyranyl.
The term "Ts" is defined as p-toluenesulfonyl or tosyl.
The carbon atom content of hydrocarbon-containing moieties is indicated by a subscript designating the minimum and maximum number of carbon atoms in the moiety, e.g., "$C_{1-6}$alkyl" refers to an alkyl group having one to six carbon atoms, inclusive.

The term "Me" is methyl ($CH_3$), "Et" is ethyl ($C_2H_5$), and "Ph" is phenyl ($C_6H_5$).

In the structures herein, for a bond lacking a substituent, the substituent is methyl, for example,

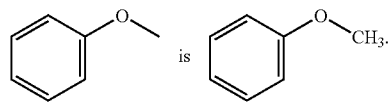

When no substituent is indicated as attached to a carbon atom on a ring; it is understood that the carbon atom contains the appropriate number of hydrogen atoms. In addition, when no substituent is indicated as attached to a carbonyl group or a nitrogen atom, for example, the substituent is understood to be hydrogen, e.g.,

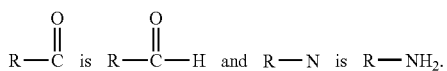

The notation

and similar notations mean that the ring system is attached to the remainder of the compound via any atom of the A or B ring.

The notation $N(R^x)_2$, wherein x represents an alpha or numeric character, such as, for example, $R^a$, $R^b$, $R^1$, $R^2$, and the like, is used to denote two $R^x$ groups attached to a common nitrogen atom. When used in such notation, the $R^x$ group can be the same or different, and is selected from the group as defined by the $R^x$ group.

The present invention also is directed to pharmaceutical compositions containing one or more compounds of structural formula (I), to use of the compounds and compositions containing the compounds in therapeutic treatment of a disease or disorder, and to methods of preparing the compounds and intermediates involved in the synthesis of the compounds of structural formula (I).

As used herein, the term "composition" is intended to encompass a product comprising the specified ingredients in the specified amounts, as well as any product which results directly, or indirectly, from admixing of the specified ingredients in the specified amounts.

The present invention includes all possible stereoisomers and geometric isomers of compounds of structural formula (I). The present invention includes not only racemic compounds but also the optically active isomers as well. When a compound of structural formula (I) is desired as a single enantiomer, it can be obtained either by resolution of the final product or by stereospecific synthesis from either isomerically pure starting material or use of a chiral auxiliary reagent, for example, see Z. Ma et al., *Tetrahedron: Asymmetry*, 8(6), pages 883–888 (1997). Resolution of the final product, an intermediate, or a starting material can be achieved by any suitable method known in the art. Additionally, in situations where tautomers of the compounds of structural formula (I) are possible, the present invention is intended to include all tautomeric forms of the compounds. As demonstrated hereafter, specific stereoisomers can exhibit an exceptional ability to inhibit HIV protease, and can be used alone or in combination with other HIV and AIDS therapies.

As used herein, the term pharmaceutically acceptable salts refers compounds of structural formula (I) which contain acidic moieties and form salts with suitable cations. Suitable pharmaceutically acceptable cations include alkali metal (e.g., sodium or potassium) and alkaline earth metal (e.g., calcium or magnesium) cations. The pharmaceutically acceptable salts of the compounds of structural formula (I), which contain a basic center, are acid addition salts formed with pharmaceutically acceptable acids. Examples include the hydrochloride, hydrobromide, sulfate or bisulfate, phosphate or hydrogen phosphate, acetate, benzoate, succinate, fumarate, maleate, lactate, citrate, tartrate, gluconate, methanesulfonate, benzene sulfonate, and p-toluenesulfonate salts. In light of the foregoing, any reference to compounds of the present invention appearing herein is intended to include compounds of structural formula (I), as well as pharmaceutically acceptable salts, prodrugs, and solvates thereof.

The term "prodrug" as used herein refers to compounds that are rapidly transformed in vivo to a compound having structural formula (I), for example, by hydrolysis. Prodrug design is discussed generally in Hardma et al. (Eds.), *Goodman and Gilman's The Pharmacological Basis of Therapeutics*, 9th ed., pp. 11–16 (1996). A thorough discussion is provided in Higuchi et al., *Prodrugs as Novel Delivery Systems*, Vol. 14, ASCD Symposium Series, and in Roche (ed.), *Bioreversible Carriers in Drug Design*, American Pharmaceutical Association and Pergamon Press (1987). Typically, administration of a drug is followed by elimination from the body or some biotransformation whereby the biological activity of the drug is reduced or eliminated. Alternatively, a biotransformation process can lead to a metabolic by-product, which is itself more or equally active compared to the drug initially administered. Increased understanding of these biotransformation processes permits the design of so-called "prodrugs," which, following a biotransformation, become more physiologically active in their altered state. Prodrugs, therefore, encompass compounds that are converted to pharmacologically active metabolites.

To illustrate, prodrugs can be converted into a pharmacologically active form through hydrolysis of, for example, an ester or amide linkage, thereby introducing or exposing a functional group on the resultant product. The prodrugs can be designed to react with an endogenous compound to form a water-soluble conjugate that further enhances the pharmacological properties of the compound, for example, increased circulatory half-life. Alternatively, prodrugs can be designed to undergo covalent modification on a functional group with, for example, glucuronic acid, sulfate, glutathione, an amino acid, or acetate. The resulting conjugate can be inactivated and excreted in the urine, or rendered more potent than the parent compound. High molecular weight conjugates also can be excreted into the bile, subjected to enzymatic cleavage, and released back into the circulation, thereby effectively increasing the biological half-life of the originally administered compound.

The compounds of the present invention can be therapeutically administered as the neat chemical, but it is preferable to administer compounds of structural formula (I) as a pharmaceutical composition or formulation. Accordingly, the present invention further provides for pharmaceutical formulations comprising a compound of structural formula (I), or pharmaceutically acceptable salts thereof, together with one or more pharmaceutically acceptable carriers and, optionally, other therapeutic and/or prophylactic ingredients. The carriers are "acceptable" in the sense of being compatible with the other ingredients of the formulation and not deleterious to the recipient thereof.

Inhibition of HIV protease typically is measured using a dose-response assay in which a sensitive assay system is contacted with a compound of interest over a range of concentrations at which no or minimal effect is observed, through higher concentrations at which partial effect is observed, to saturating concentrations at which a maximum effect is observed. Assays of the dose-response effect of inhibitor compounds can be described as a curve expressing a degree of inhibition as a function of concentration. The curve theoretically passes through a point at which the concentration is sufficient to reduce activity of the HIV protease enzyme to a level that is 50% that of the difference between minimal and maximal enzyme activity in the assay. This concentration is defined as the Inhibitory Concentration (50%) or $IC_{50}$.

Comparisons of the efficacy of inhibitors often are provided with reference to comparative $IC_{50}$ values, wherein a higher $IC_{50}$ value indicates that the test compound is less potent, and a lower $IC_{50}$ value indicates that the compound is more potent, than a reference compound. Compounds useful for the method of the present invention demonstrate an $IC_{50}$ value of less than 100 µM when measured using the dose-response assay. Preferred compounds demonstrate an $IC_{50}$ value of less than 50 µM. More preferred compounds demonstrate an $IC_{50}$ value of less than 5 µM. Still more preferred compounds for the present invention demonstrate an $IC_{50}$ value of less than 3 µM (3000 nM), less than 0.5 µM (500 nM), and less than 0.1 µM (100 nM), for example, 5 pM to 0.1 nM.

Compounds and pharmaceutical compositions suitable for use in the present invention include those wherein the active ingredient is administered in an effective amount to achieve its intended purpose. More specifically, a "therapeutically effective amount" means an amount effective to inhibit development of, or to alleviate the existing symptoms of, the subject being treated. Determination of the effective amount is well within the capability of those skilled in the art, especially in light of the detailed disclosure provided herein.

A "therapeutically effective dose" refers to that amount of the compound that results in achieving the desired effect. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, which is expressed as the ratio of $LD_{50}$ to $ED_{50}$. Compounds that exhibit high therapeutic indices (i.e., a toxic dose that is substantially higher than the effective dose) are preferred. The data obtained can be used in formulating a dosage range for use in humans. The dosage of such compounds preferably lies within a range of circulating concentrations that include the ED50 with little or no toxicity. The dosage can vary within this range depending upon the dosage form employed, and the route of administration utilized.

The term "container" means any receptacle and closure therefore suitable for storing, shipping, dispensing, and/or handling a pharmaceutical product.

The term "insert" means information accompanying a product that provides a description of how to administer the product, along with the safety and efficacy data required to allow the physician, pharmacist, and patient to make an informed decision regarding use of the product. The package insert generally is regarded as the "label" for a pharmaceutical product.

The exact formulation, route of administration, and dosage can be chosen by the individual physician in view of the patient's condition. Dosage amount and interval can be adjusted individually to provide plasma levels of the active moiety which are sufficient to maintain the therapeutic effects.

Pharmaceutical compositions of the invention can be formulated to include a compound of structural formula (I) and one or more additional agents useful in the treatment of HIV and AIDS. For example, compounds of the present invention can be effectively administered at a period of preexposure and/or postexposure, in combination with a therapeutically effective amount of an AIDS antiviral, immunomodulator, antiinfective, or vaccine, such as those disclosed in U.S. Pat. No. 6,245,806, incorporated herein by reference.

As appreciated by persons skilled in the art, reference herein to treatment extends to prophylaxis, as well as to treatment of established diseases or symptoms. It is further appreciated that the amount of a compound of the invention required for use in treatment varies with the nature of the condition being treated, and with the age and the condition of the patient, and is ultimately determined by the attendant physician or veterinarian.

In general, however, doses employed for adult human treatment typically are in the range of 0.001 mg/kg to about 100 mg/kg per day. The desired dose can be administered in a single dose, or as multiple doses administered at appropriate intervals, for example as two, three, four or more subdoses per day. In practice, the physician determines the actual dosing regimen which is most suitable for an individual patient, and the dosage varies with the age, weight, and response of the particular patient. The above dosages are exemplary of the average case, but there can be individual instances in which higher or lower dosages are merited, and such are within the scope of the present invention.

The terms "administration of" and "administering a" compound should be understood to mean providing a compound of the invention or a prodrug of a compound of the invention to an individual in need of treatment.

Thus, in accordance with important features of the present invention, a method of treating, and a pharmaceutical composition for treating, HIV infection and AIDS are provided. The treatment involves administering to a patient in need of such treatment a pharmaceutical composition comprising a pharmaceutical carrier, a therapeutically effective amount of a compound of structural formula (I), and an optional agent useful in the treatment of HIV or AIDS.

Compounds and compositions of the present invention can be administered in a standard manner for the treatment of the indicated diseases, such as orally, parenterally, transmucosally (e.g., sublingually or via buccal administration), topically, transdermally, rectally, via inhalation (e.g., nasal or deep lung inhalation). Parenteral administration includes, but is not limited to intravenous, intraarterial, intraperitoneal, subcutaneous, intramuscular, intrathecal, and intraarticular. Parenteral administration also can be accomplished using a high pressure technique, like POWDERJECT™.

Such preparations also can be formulated as suppositories, e.g., containing conventional suppository bases, such as cocoa butter or other glycerides. Compositions for inhalation typically can be provided in the form of a solution, suspension, or emulsion that can be administered as a dry powder or in the form of an aerosol using a conventional propellant, such as dichlorodifluoromethane or trichlorofluoromethane. Typical topical and transdermal formulations comprise conventional aqueous or nonaqueous vehicles, such as eye drops, creams, ointments, lotions, and pastes, or are in the form of a medicated plaster, patch, or membrane.

Additionally, compositions of the present invention can be formulated for parenteral administration by injection or continuous infusion. Formulations for injection can be in the form of suspensions, solutions, or emulsions in oily or aqueous vehicles, and can contain formulation agents, such as suspending, stabilizing, and/or dispersing agents. Alternatively, the active ingredient can be in powder form for constitution with a suitable vehicle (e.g., sterile, pyrogen-free water) before use.

A composition of the present invention also can be formulated as a depot preparation. Such long acting formulations can be administered by implantation (for example, subcutaneously or intramuscularly) or by intramuscular injection. Accordingly, the compounds of the invention can be formulated with suitable polymeric or hydrophobic materials (e.g., an emulsion in an acceptable oil), ion exchange resins, or as sparingly soluble derivatives (e.g., a sparingly soluble salt).

For veterinary use, a compound of formula (I), or a nontoxic salt thereof, is administered as a suitably acceptable formulation in accordance with normal veterinary practice. The veterinarian can readily determine the dosing regimen and route of administration that is most appropriate for a particular animal.

As previously stated, the HIV protease inhibitors of the present invention can be administered as the sole active agent, or they can be used in combination with a second active agent which is effective against retroviruses, such as HIV-1. Such second active agents include, but are not limited to, other HIV protease inhibitors, various nucleoside analogs, nonnucleoside reverse transcriptase inhibitors, antivirals, immunomodulators, antiinfectives, tat antagonists, and glycosidase inhibitors. Numerous examples of such second active agents are set forth in U.S. Pat. Nos. 6,100,277 and 6,245,806, both incorporated herein by reference, and include, but are not limited to, Ro 31-859, KNI-272, AZT, DDI, DDC, 3TC, D4T, PMEA, Ro 5-3335, Ro 24-7429, indinavir, ritonavir, saquinavir, nelfinavir, amprenavir, abacavir, castanospremine, castanospermine 6-butryl ester, N-butyl-1-deoxy-nojirimycin, N-butyl-1-deoxynojirimycin per-butryl ester, 097, acemannan, acyclovir, AD-439, AD-519, adefovir clipivoxil, AL-721, alpha interferon, ansamycin, beta-fluoro-ddA, BMS-232623, BMS-234475, CI-1012, cidofovir, delaviridine, EL-10, efaviren, famciclovir, FTC, hypericin, Compound Q, ISIS 2922, lobucavir, nevirapine, novapren, peptide T, octapeptide, PNU-140690, probacol, stavudine, valaciclovir, virazole, zalcitabine, ABT-378, bropirimine, gamma interferon, interleukin-2, TNF, etanercept, infliximab, fluconalzole, piritrexim, trimetrexate, daunorubicin, leukotriene B4 receptor antagonist, and analogs and prodrugs thereof.

The protease inhibitors of the present invention and the second active agent can be formulated as separate compositions which are administered at substantially the same time, i.e., simultaneously or sequentially, or the therapeutic agents can be administered from a single composition, such that all of the active agents are present in the host in a therapeutically effective amount. Alternatively, the therapeutic agents can be administered to the host at different times, i.e., separately, such that only one or two active agents at a time are present in the host in a therapeutically effective amount.

The compounds of structural formula (I) are effective antiviral compounds and, in particular, are effective retroviral inhibitors. Thus, the subject compounds are effective HIV protease inhibitors. The subject compounds of the present invention also inhibit other retroviruses, such as other lentiviruses, in particular, other strains of HIV, e.g., HIV-2, human T-cell leukemia virus, rous sarcoma virus, simian immunodeficiency virus, feline leukemia virus, feline immunodeficiency virus, and the like. The compounds of structural formula (I), therefore, are effective in the treatment and/or prophylaxis of retroviral infections.

In addition, the compounds of structural formula (I) are effective in preventing the growth of retroviruses in a solution. Both human and animal cell cultures, such as T-lymphocyte cultures, are utilized for a variety of purposes, such as research and diagnostic procedures including calibrators and controls. Prior to and during the growth and storage of a cell culture, the present inhibitors can be added to a cell culture medium at an effective concentration to prevent the unexpected or undesired replication of a retrovirus that may inadvertently or unknowingly be present in the cell culture. For example, the virus may be present originally in the cell culture because HIV is known to be present in human T-lymphocytes long before it is detectable in blood, or through exposure to the virus. This use of the present inhibitors prevents the unknowing or inadvertent exposure of a potentially lethal retrovirus to a researcher or clinician.

The present invention, therefore, provides a pharmaceutical composition comprising a compound of structural formula (I), together with a pharmaceutically acceptable diluent or carrier therefor. The present invention also provides a process of preparing a pharmaceutical composition comprising mixing a compound of formula (I), together with a pharmaceutically acceptable diluent or carrier therefor. Further provided are articles of manufacture comprising a compound of structural formula (I) and a second pharmaceutical drug, packaged separately or together, and an insert having instructions for using the active agents.

Specific, nonlimiting examples of compounds of structural formula (I) are provided below, the syntheses of which were performed in accordance with the procedures set forth hereafter.

EXAMPLE 1

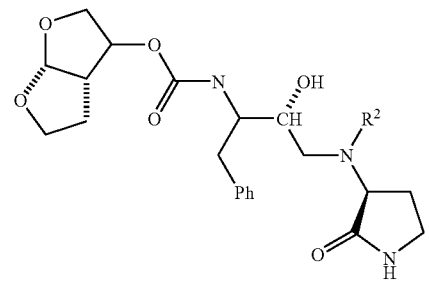

EXAMPLE 2

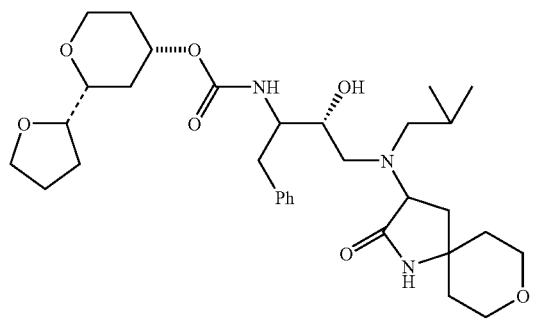

EXAMPLE 3

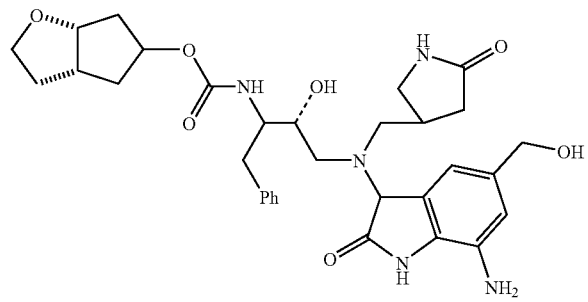

EXAMPLE 4

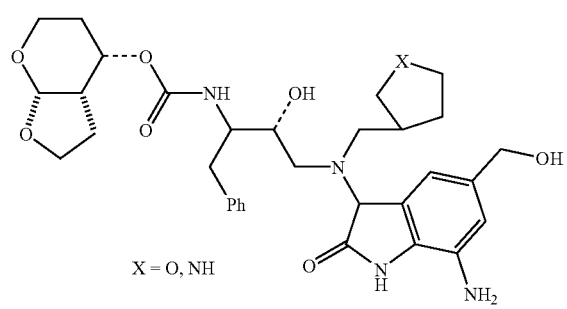

X = O, NH

EXAMPLE 5
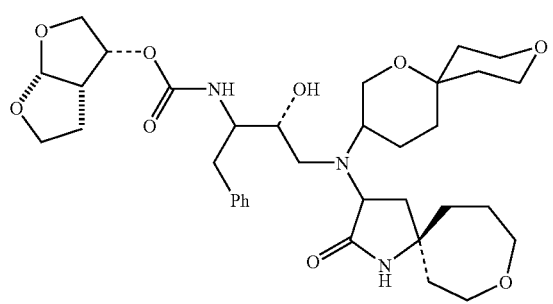
EXAMPLE 9
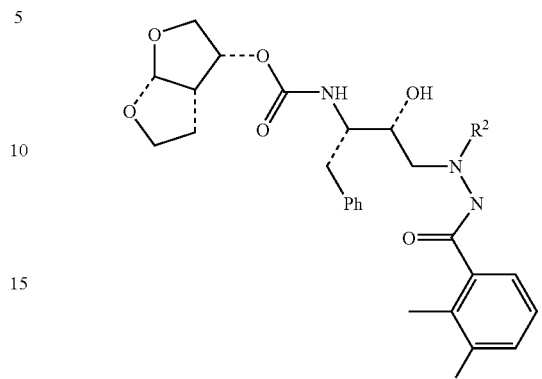
EXAMPLE 6
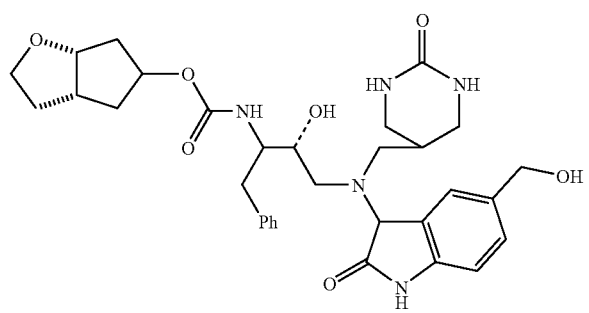
EXAMPLE 10
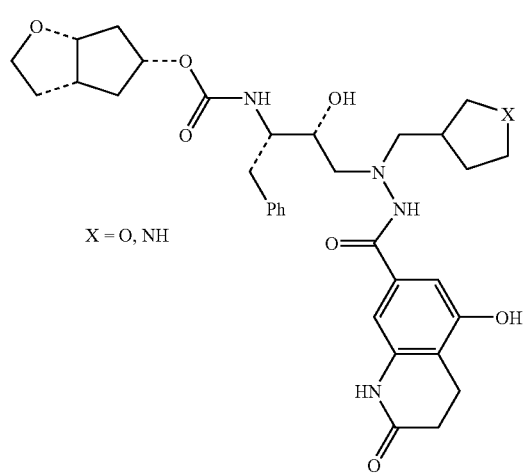
X = O, NH
EXAMPLE 7
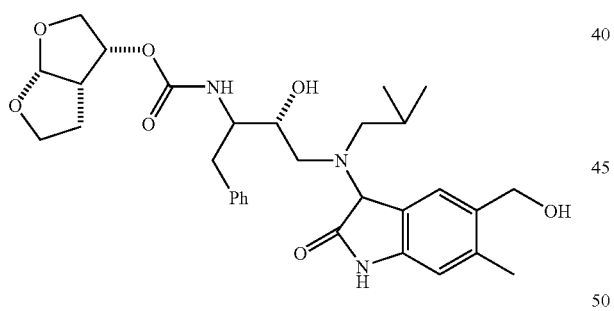
EXAMPLE 11
EXAMPLE 8
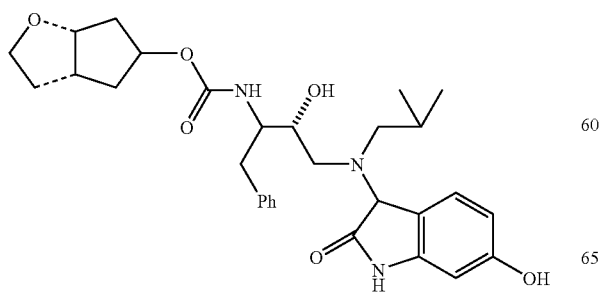
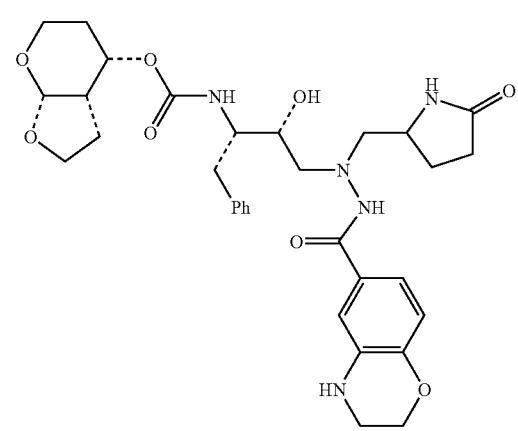

EXAMPLE 12

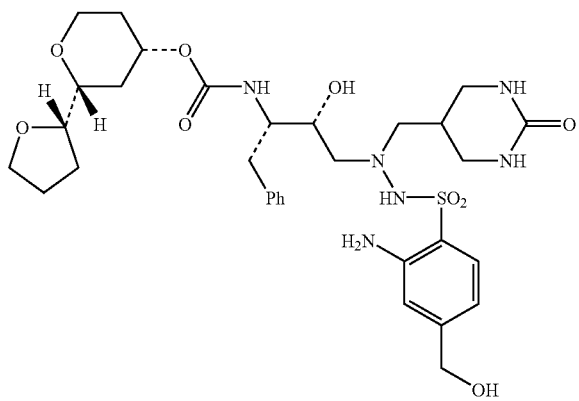

EXAMPLE 13

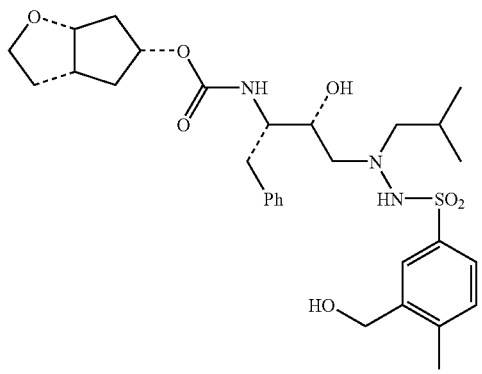

EXAMPLE 14

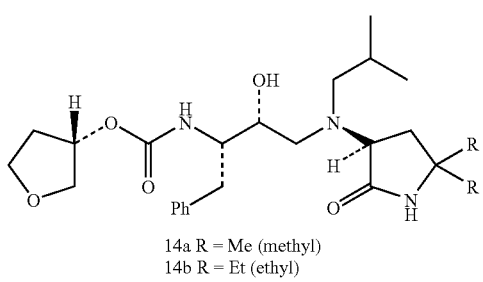

14a R = Me (methyl)
14b R = Et (ethyl)

EXAMPLE 15

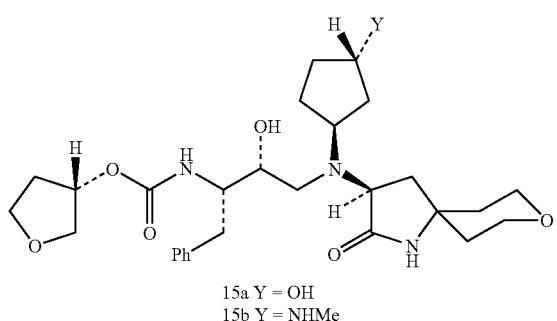

15a Y = OH
15b Y = NHMe

EXAMPLE 16

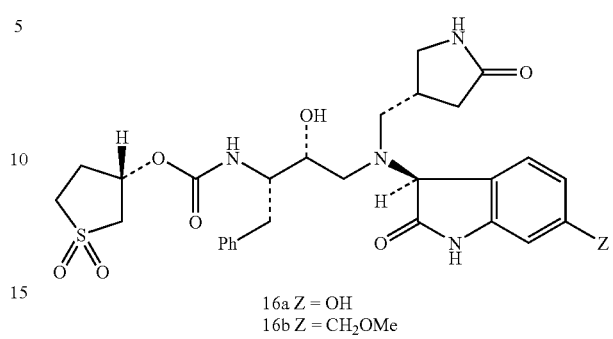

16a Z = OH
16b Z = CH$_2$OMe

Generally, compounds of structural formula (I) can be prepared according to the synthetic schemes depicted herein. In these synthetic schemes, it is understood in the art that protecting groups can be employed where necessary in accordance with general principles of synthetic chemistry. These protecting groups are removed in the final steps of the synthesis under basic, acidic, or hydrogenolytic conditions which are readily apparent to those skilled in the art. By employing appropriate manipulation and protection of chemical functionalities, synthesis of compounds of structural formula (I) not specifically set forth herein can be accomplished by methods analogous to the scheme set forth herein.

Compounds of the present invention were tested for an ability to inhibit HIV-1 protease by the test method set forth below. The data set forth hereafter in the form of IC$_{50}$ values shows that compounds of the present invention are potent inhibitors of HIV protease.

HIV-1 Protease Inhibition Assay

The HIV-1 protease gene was subcloned into the pET30a vector (Novagen) and then transformed into BL21 (dE3) pLysS cells for protein expression. Protein expression and purification were followed according to Tang's procedure (Hong et al., *Biochemistry*, 1996, 35, 10627–10633). Accumulation of protein has resulted in cellular inclusion bodies. The cell lysates analyzed by SDS-polyacrylamide gel electrophoresis showed the expected 11 kDa major band. The inclusion body containing some bacterial proteins was thoroughly washed by using TRITON X-100, solubilized in 8M urea and passed through the Q-sepharose column to remove the bacterial proteins which interfered with subsequent refolding steps. HIV-1 protease was refolded from the urea to an active form by dialysis. As a final step, gel filtration chromatography was used to remove impurities after refolding. Activities of purified HIV-1 protease were examined using a fluorogenic substrate, 2-aminobenzoyl-Thr-Ile-Nle-Phe(pNO2)-Gln-Arg-NH2 (Novabiochem). Kinetic measurements of the cleavage of anthranilyl fluorogenic substrate by HIV-1 protease showed typical Michaelis-Menten behavior. The Michaelis constant for the substrate is $K_m$=4.5 μM. Using the first rate equation, $k_{cat}$ is calculated. In the condition of $S_o<<K_m$, $v=E_o(k_{cat}/K_m)S_o$, where $E_o$ is the total enzyme concentration, and $S_o$ is the substrate concentrate. Then, $k_{cat}$=0.70±0.05 s$^{-1}$. Assays are carried out as described by Toth and Marshall (Toth et al., *Int. J. Pept. Protein Res.*, 1990, 36, 544–50).

EXPERIMENTALS

(3aR,5R,6aR)-(Carbonic acid 2',5'-dioxo-pyrrolidin-1-yl-ester)-hexahydrocyclopenta[b]furan-5-yl-ester (4)

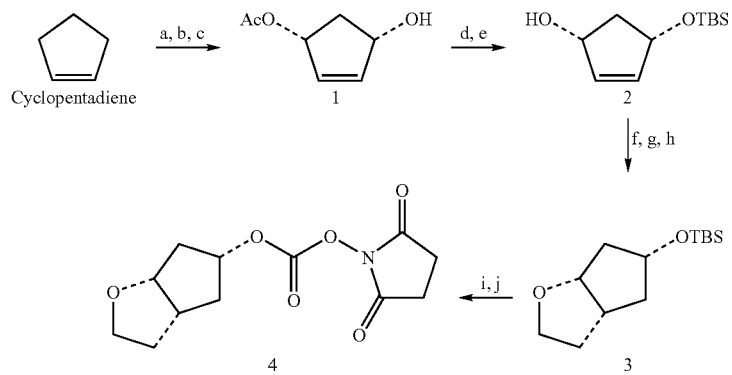

Key: (a) Thiourea, Rose Bengal, $O_2$, MeOH, hv, 8 h; (b) $Ac_2O$, Py, DMAP, $CH_2Cl_2$, 1 hour. 42% for two steps; (c) $NaN_3$, acetyl cholinesterase (type VI-S) phosphonate buffer (0.5 M, pH 7.0), 12 hours, 70%; (d) TBSCl, imidazole, DMF, 30 min; (e) $K_2CO_3$, MeOH, 20 min. 94% for two steps; (f) NBS, ethyl vinyl ether, −45° C. to 23° C., 12 hours; (g) n-$Bu_3$SnH, AIBN, benzene, reflux, 4 hours; (h) $BF_3.OEt_2$, $Et_3$SiH, $CH_2Cl_2$, 0° C., 10 min.; (i) 45% aq. HF, $CH_3$CN, 15 min.; (j) DSC, $Et_3$N, $CH_3$CN, 2 hours, 47% for two steps.

A cold solution of cyclopentadiene (16 mL), thiourea (10 g), and Rose Bengal (300 mg) in methanol (MeOH) (1000 mL) was purged with oxygen and irradiated with a 75 Watt halogen lamp. After 8 hours, the solution was held at room temperature in the absence of light for 12 hours. Solvents were evaporated under reduced pressure, then MeOH (200 mL) was added. After filtering, the filtrate was concentrated and the crude product was passed through a silica gel column to provide a crude diol.

The crude diol, acetic anhydride ($Ac_2O$) (58.8 g, 0.57 moles), pyridine (77 g, 1.15 moles), and DMAP (4-dimethylaminopyridine) (200 mg) in methylene chloride ($CH_2Cl_2$) (1000 mL) were stirred for 2 hours. The reaction mixture was washed with water (2×300 mL) then concentrated. The resulting crude diacetate was purified by silica gel chromatography to obtain 17.9 g (42%, two steps) of the diacetate. $^1$H NMR ($CDCl_3$, 200 MHz): δ 6.07 (m, 2H), 5.5 (m, 2H), 2.85 (m, 1H), 2.05 (s, 6H), 1.7 (m, 1H).

The diacetate (4.1 g, 22.8 mmol), sodium azide ($NaN_3$) (15 mg), and acetyl cholinesterase (2.8 mg, type VI-S; from Electric Eel, Sigma, Inc.) were slowly stirred in phosphate buffer (0.5 M, pH 7.0) for 12 hours. Then, the reaction mixture was extracted with EtOAc (EtOAc) (3×200 mL), washed with brine (200 mL), and concentrated under reduced pressure. The crude product was purified by silica gel chromatography to obtain 2.2 g (70%) of compound 1; $[α]^{25}_D$: +59.35 (89% ee).

(1R,4S)-4-(tert-Butyl-dimethylsilanyloxy)-cyclopent-2-enol (2)

The alcohol (200 mg, 1.48 mmol), tert-butyldimethylsilanyl chloride (TBSCl) (267 mg, 1.48 mmol), and imidazole (191 mg, 2.86 mmol) in dimethylformamide (DMF) (10 mL) were stirred for 30 minutes. Then, the reaction mixture was diluted with EtOAc (50 mL) and washed several times with water (2×50 mL). The organic layer was dried over anhydrous sodium sulfate ($Na_2SO_4$) and the solvents were evaporated in vacuo. Purification of the crude product by silica gel chromatography provided the TBS ether as a colorless liquid. The TBS ether and potassium carbonate ($K_2CO_3$) (323 mg, 2.34 mmol) in MeOH (10 mL) were stirred for 20 minutes at room temperature. The MeOH was evaporated and the reaction mixture was extracted with EtOAc (2×50 mL), dried over anhydrous $Na_2SO_4$, and concentrated under reduced pressure. Silica gel chromatographic purification of the crude product provided compound 2 (300 mg, 94%, two steps) as a colorless oil. $^1$H NMR ($CDCl_3$, 200 MHz): δ 5.92 (m, 2H), 4.6 (m, 2H), 2.68 (m, 1H), 1.77 (m, 1H), 1.49 (m, 1H), 0.90 (s, 9H), 0.09 (s, 6H).

(3aR,5R,6aR)-5-tert-Butyldimethysiloxy-hexahydro-cyclopenta[b]furan (3)

A solution of compound 2 (300 mg, 1.4 mmol) and N-bromosuccinimide (NBS) (248 mg, 1.4 mmol) in $CH_2Cl_2$ (5 mL) at −45° C. was added to ethyl vinyl ether (151 mg, 2.1 mmol). The resulting mixture was warmed to room temperature and, after 12 hours, treated with aq. ammonium chloride ($NH_4Cl$) (10 mL), then washed with brine (50 mL). The organic layer was dried over anhydrous $Na_2SO_4$, then concentrated in vacuo. Purification of the crude product by silica gel chromatography provided a bromoethoxy compound (468 mg) as colorless liquid.

The bromoethoxy compound (464 mg, 1.18 mmol), tri-n-butyltin hydride (n$Bu_3$SnH) (412 mg, 1.41 mmol), and AIBN (10 mg) in benzene (5 mL) were refluxed for 4 hours. The reaction mixture then was cooled to room temperature, and the crude product was chromatographed on silica gel to obtain a bicyclic ether (300 mg) as a viscous liquid.

To the bicyclic ether and triethylsilane ($Et_3$SiH) (331 mg, 2.85 mmol) in $CH_2Cl_2$ (5 mL) at 0° C. was added boron trifluoride etherate ($BF_3.OEt_2$) (2.85 mmol). The reaction was complete in 10 minutes. Sodium bicarbonate ($NaHCO_3$) (10 mL) was added and the reaction mixture was extracted with $CH_2Cl_2$ (2×10 mL). The combined extracts were dried over anhydrous $Na_2SO_4$ and concentrated in vacuo. Purification by silica gel chromatography provided compound 3 as a colorless liquid. $^1$H NMR ($CDCl_3$, 400 MHz): δ 4.39 (m, 1H), 4.06 (m, 1H), 3.88 (m, 1H), 3.78 (m, 1H), 2.53 (m, 1H), 2.1–1.9 (m, 3H),1.72 (m, 1H),1.58 (m, 1H),1.42 (m, 1H),0.91 (s, 9H), 0.03 (s, 6H).

(3aR,5R,6aR)-(Carbonic acid-2',5'-dioxo-pyrrolidin-1-ylester)-hexahydro-cyclopenta[b]furan-5-yl ester (4)

Ether 3 (175 mg, 0.72 mmol), HF (45%, 0.2 mL), and CH$_3$CN (2 mL) were stirred in a plastic container for 15 minutes. Aq. NaHCO$_3$ (5 mL) was added to the mixture and the contents of the flask were extracted with EtOAc. The combined organic layer was washed with brine (10 mL) to obtain the crude alcohol which was purified by silica gel chromatography. [α]$^{25}_D$: –14.67°, c, 1.85, CHCl$_3$. $^1$H NMR (CDCl$_3$, 200 MHz): δ 4.36 (dt, 1H, J=1.43 Hz, 6.4 Hz), 4.22 (m, 1H), 3.98 (m, 1H), 3.58 (m, 1H), 2.71 (m, 1H), 2.5 (s, 1H), 2.2–1.5 (m, 6H).

The above alcohol (73 mg, 609 mmol), N,N'-disuccinimidyl carbonate (187 mg, 0.731 mmol), and triethylamine (Et$_3$N) (92 mg, 0.913 mmol) in CH$_3$CN (2 mL) were stirred for 12 hours. The solvents were evaporated and the crude alcohol was purified by silica gel chromatography to provide carbonate 4 (91 mg, 47%, two steps).

(3aS,5S,6aS)-(Carbonic acid 2',5'-dioxo-pyrrolidin-1-yl ester)-hexahydrocyclopenta[b]furan-5-yl ester (6)

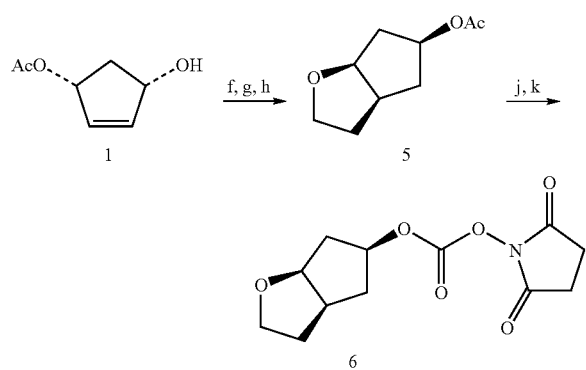

Key: (a) NBS, ethyl vinyl ether, –45° C. to 23° C., 12 hours; (b) n-Bu$_3$SnH, AIBN, benzene, reflux, 4 hours; (c) BF$_3$ OEt$_2$, Et$_3$SiH, CH$_2$Cl$_2$, 0° C., 10 min., 58% for three steps; (d) K$_2$CO$_3$, MeOH, 90 min; and (j) DSC, Et$_3$N, CH$_3$CN, 12 hours, 92% for two steps.

(3aS,5S,6aS)-Acetic acid hexahydrocyclopenta[b]-furan-5-yl ester (5)

To alcohol 1 (199 mg, 1.4 mmol) and N-bromosuccinimide (249 mg, 1.4 mmol) in CH$_2$Cl$_2$ (5 mL) at –45° C. was added ethyl vinyl ether (152 mg, 2.11 mmol) using the same reaction conditions as in the synthesis of compound 3 to obtain a bromo compound (332 mg). $^1$H NMR (CDCl$_3$, 200 MHz): δ 6.0 (m, 2H), 5.5 (m, 1H), 4.7 (m, 2H), 3.6 (m, 2H), 3.35 (d, 2H, J=5.3 Hz), 2.8 (m, 1H), 2.0 (s, 3H), 1.8 (m, 1H), 1.2 (t, 3H, J=7 Hz).

The bromo compound (332 mg, 1.13 mmol), nBu$_3$SnH (395 mg, 1.35 mmol), and 2,2'-azobisisobutyronitrile (AIBN) (20 mg) in toluene were refluxed as described in the synthesis of compound 3 to obtain a bicyclic ether (228 mg) as a colorless oil.

To the bicyclic ether (228 mg, 1.065 mmol) and Et$_3$SiH (370 mg, 3.196 mmol) in CH$_2$Cl$_2$ (5 mL) at room temperature, was added BF$_3$.OEt$_2$ (450 mg, 3.196 mmol) following the same reaction conditions as described in the synthesis of compound 3 to obtain compound 5 (140 mg, 58% three steps) as an oil. $^1$H NMR (CDCl$_3$, 200 MHz): δ 5 (m, 1H), 4.5 (m, 1H), 3.95 (m, 1H), 3.74 (m, 1H), 2.7 (m, 1H), 2.1 (m, 3H), 2 (s, 3H), 1.5–1.9 (m, 3H).

(3aS,5S,6aS)-(Carbonic acid 2',5'-dioxo-pyrrolidin-1-yl ester)-hexahydrocyclopenta[b]furan-5-yl ester (6)

Compound 5 (133 mg, 0.78 mmol) and K$_2$CO$_3$ (215 mg, 1.56 mmol) in MeOH (5 mL) were stirred for 1.5 hours. The reaction mixture then was diluted with EtOAc (20 mL) and washed several times with water. The organic layer was dried over anhydrous Na$_2$SO$_4$ and concentrated under reduced pressure at 30° C. to obtain a volatile alcohol. [α]$^{25}_D$: +8.6, c, 0.7, CHCl$_3$.

The alcohol, N,N'-disuccinimidyl carbonate (240 mg, 0.938 mmol), and Et$_3$N (157 mg, 1.56 mmol) in acetonitrile (5 mL) were stirred for 12 hours. Then, the reaction mixture was diluted with EtOAc (20 mL), and washed with brine (20 mL). The organic layer was dried over anhydrous Na$_2$SO$_4$ and concentrated under reduced pressure. The crude product was purified by a silica gel column to obtain compound 6 (195 mg, 92%, two steps) as an oil. $^1$H NMR (CDCl$_3$, 300 MHz): δ 5.1 (m, 1H), 4.48 (m, 1H), 3.95 (m, 1H), 2.0–2.3 (m, 4H), 1.8 (m, 2H).

Synthesis of 4-hydroxy-3-methylbenzoic acid (8)

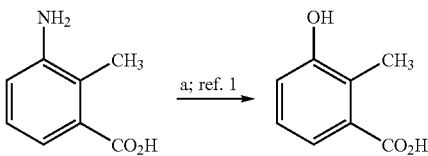

Carbonic acid 2,5-dioxo-pyrrolidin-1-yl ester hexahydro-furo[2,3-b]furan-3-yl ester (15) and (16)

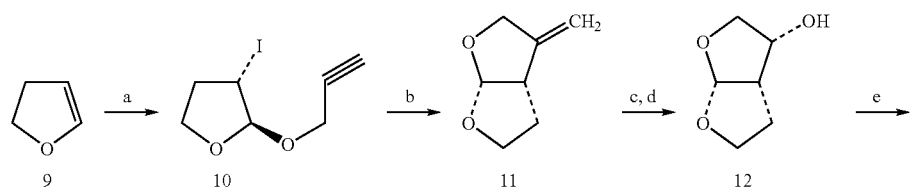

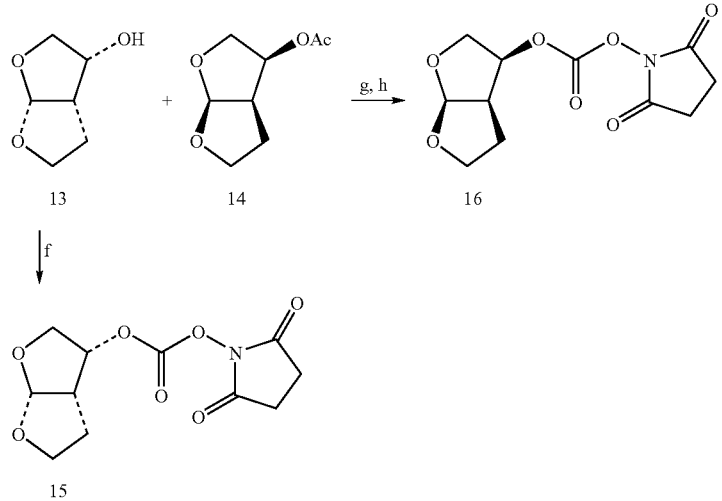

Key: (a) N-iodosuccinimide, propargyl alcohol, $CH_2Cl_2$, 0–23° C., 2 hours, 92%; (b) Cobaloxime (cat), $NaBH_4$, EtOH, 50° C., 2 hours, 73% or $Bu_3SnH$, AIBN, toluene, reflux, 1 hour, 76%; (c) $O_3$, $CH_2Cl_2$ MeOH, 30 min, $Me_2S$, −78 0° C. to 23° C., 30 min; (d) $NaBH_4$, EtOH, 0° C., 2 hours, 75%; (e) immobilized lipase 30, $Ac_2O$, DME, 23° C. 42%; (f) DSC, $Et_3N$, $CH_3CN$, 24 hours, 75%; (g) $K_2CO_3$, MeOH, 1 h; (h) DSC, $Et_3N$, $CH_3CN$, 1 hour, 73% for two steps.

Trans-2-(propargyloxy)-3-iodotetrahydrofuran (10)

To a stirred, ice cold suspension of 15 g (66.6 mmol) of N-iodosuccinimide in 150 mL of $CH_2Cl_2$ was added a mixture of dihydrofuran (66.6 mmol, 4.67 g, 5.1 mL) and propargyl alcohol (100 mmol, 5.0 g, 5.2 mL) in 50 mL of $CH_2Cl_2$ over 20 min. After warming to 24° C. with stirring over 2 hours, 200 mL of water was added and the stirring was continued for 1 hour. The layers were separated and the aqueous layer extracted with 2×100 mL of $CH_2Cl_2$. The combined organic extracts were washed with a brine solution containing a small amount of sodium thiosulfate ($Na_2S_2O_3$) (70 mg), dried over anhydrous $Na_2SO_4$, filtered, and concentrated. Chromatography over silica gel using 30% EtOAc in hexane yielded (15.4 g, 92%) of iodoether 10 as an oil. $^1$H-NMR ($CDCl_3$): δ 5.4 (br s, 1H), 4.0–4.3 (m, 5H), 2.7 (m, 1H), 2.48 (br s, 1H), 2.25 (m, 1H); IR (neat), 2956, 2180, 1621, 1440 $cm^{-1}$.

(3aR,6aS) and (3aS,6aR)-3-methylene-4H-hexahydro-furo[2,3-b]furan (11) (Tributyltin Hydride Procedure)

To a refluxing solution of tributyltin hydride (20.7 mL, 77 mmol) containing AIBN (100 mg) in toluene (200 mL) was added a solution of 15.4 g (61 mmol) of iodotetrahydrofuran 10 in toluene (50 mL) dropwise over a one-hour period. The resulting mixture was stirred at reflux for an additional 4 hours (monitored by TLC). The mixture then was cooled to 23° C. and concentrated under reduced pressure. The residue was partitioned between petroleum ether and acetonitrile (200 mL of each), and the acetonitrile (lower) layer was concentrated. The residue was purified by chromatography on silica gel, using 10% EtOAc in hexane as the eluent to provide the product 11 (5.84 g, 76%) as an oil. $^1$H-NMR ($CDCl_3$): δ 5.7 (d, 1H, J=4.9 Hz), 4.9–5.1 (m, 2H), 4.3–4.6 (m, 2H), 3.7–4.0 (m, 2H), 3.3 (m, 1H), 1.8–2.2 (m, 2H); IR (neat), 2970, 1645, 1430 $cm^{-1}$.

(3aR,6aS) and (3aS,6aR)-3-methylene-4H-hexahydro-furo[2,3-b]furan (11) (Catalytic Cobaloxime Procedure)

To a solution of iodoether 10 (6.4 g, 25.4 mmol) in 95% ethanol (80 mL) was added solid sodium borohydride ($NaBH_4$) (1.06 g, 28 mmol) and 10 N sodium hydroxide (NaOH) (2.6 ml, 26 mmol). The solution was flushed with $N_2$ and several portions of finely powered cobaloxime (611 mg, 1.5 mmol) were added over a one-hour period at 50° C. (bath temperature 65° C.). The resulting mixture was stirred for an additional hour, then the reaction mixture was concentrated under reduced pressure. The resulting residue was diluted with brine and the mixture was thoroughly extracted with ether (3×150 mL). The combined organic layers were washed with water, then brine, and dried over anhydrous $Na_2SO_4$. Evaporation of the solvent gave a residue which was chromatographed over silica gel to provide the product 11 (2.3 g, 73%) as an oil. $^1$H-NMR ($CDCl_3$): δ 5.7 (d, 1H, J=4.9 Hz), 4.9–5.1 (m, 2H), 4.3–4.6 (m, 2H), 3.7–4.0 (m, 2H), 3.3 (m, 1H), 1.8–2.2 (m, 2H); IR (neat): 2970, 1645, 1430 $cm^{-1}$; MS (70 eV) m/z 126 (m+).

(3S,3aR,6aS) and (3R,3aS,6aR)-3-hydroxy-4H-hexahydrofuro[2,3-b]furan (12)

A stream of ozone was dispersed into a solution of compound 11 (5.84 g, 46.4 mmol) in MeOH (150 mL) and $CH_2Cl_2$ (150 mL) at −78° C. for 30 min. The resulting blue solution was purged with nitrogen until colorless, then quenched with 20 mL of dimethyl sulfide. The resulting mixture was allowed to warm to 23° C. The mixture then was concentrated under reduced pressure to afford a crude ketone. The ketone was dissolved in ethanol (50 mL), cooled to 0° C., and sodium borohydride (2.1 g, 55.6 mmol) was added. The reaction mixture was stirred for an additional 2 hours at 0° C., and then quenched with 10% aqueous citric acid (10 mL). The resulting mixture was concentrated under reduced pressure, and the residue was partitioned between EtOAc and brine. The layers were separated and the aqueous layer was extracted with EtOAc (2×100 mL). The combined organic layers were dried over anhydrous $Na_2SO_4$ and concentrated carefully under reduced pressure. The resulting residue was chromatographed over silica gel using 30% EtOAc in hexane as the eluent to furnish (4.52 g, 75%) the racemic alcohol 12 as an oil. $^1$H-NMR ($CDCl_3$): δ 5.7 (d, J=5.13, 1H), 4.45 (dd, J=6.8, 14.6, 1H), 3.9–4.0 (m, 3H), 3.65 (dd, 1H, J=7, 9.1), 2.9 (m, 1H), 2.3 (m, 1H), 1.85 (m, 2H); IR (neat): 2951, 1640, 1346, 1210 $cm^{-1}$; MS (70 eV) m/z 131 (m++ H).

Preparation of Immobilized Amano Lipase 30

Commercially available celite 521 (4 g, Aldrich) was loaded on a Buchner funnel and washed successively with 50 mL of deionized water and 50 mL of 0.05 N phosphate buffer (pH=7.0; Fisher Scientific). The washed celite then was added to a suspension of 1 g of Amano lipase 30 in 20 mL of 0.05 N phosphate buffer. The resulting slurry was spread on a glass dish and allowed to air dry at 23° C. for 48 hours (weight 5.4 g; water content about 2% by Fisher method).

(3R,3aS,6aR)-3-hydroxyhexahydrofuro[2,3-b]furan (13) by Immobilized Lipase Catalyzed Acylation To a stirred solution of racemic alcohol 12 (2 g, 15.4 mmol) and $Ac_2O$ (4 g, 42.4 mmol) in 100 mL of DME (ethylene glycol dimethyl ether) was added 2.7 g (about 25% by weight of lipase, PS30) of immobilized Amano lipase and the resulting suspension was stirred at 23° C. The reaction was monitored by TLC and $^1$H NMR analysis until 50% conversion was attained. The reaction mixture was filtered, and the filter cake was washed repeatedly with EtOAc. The combined filtrate was carefully concentrated in a rotary evaporator, maintaining the bath temperature below 15° C. The residue was chromatographed over silica gel to provide 843 mg (42%) of compound 13 (95% ee; $[α]^{25}_D$: −11.9°, c 1.24, MeOH); $^1$H-NMR ($CDCl_3$): δ 5.7 (d, 1H, J=5.1 Hz), 4.45 (dd, 1H, J=6.8, 14.6 Hz), 3.85–4.0 (m, 3H), 3.65 (dd, 1H, J=7.0, 9.1 Hz), 2.9 (m, 1H), 2.3 (m, 1H), 1.85 (m, 2H); also, 1.21 g of compound 14 after washing with 5% aqueous sodium carbonate (45%, $[α]^{25}_D$: +31.8°, c 1.86, MeOH); 1H-NMR ($CDCl_3$): δ 5.7 (d, 1 H, J=5.2 Hz), 5.2 (dd, 1H, J=6.4, 14.5 Hz), 3.8–4.1 (m, 3H), 3.75 (dd, 1H, J=6.6, 9.2 Hz), 3.1 (m, 1H), 2.1 (s, 3H), 1.85–2.1 (m, 2H); IR (neat): 2947, 1750, 1630, 1338, 1220 $cm^{-1}$.

(3S,3aS,6aR)-Carbonic acid 2,5-dioxo-pyrrolidin-1-yl ester hexahydrofuro[2,3-b]furan-3-yl ester (15)

Compound 13 (2 g, 15.3 mmol), N,N'-disuccinimidyl carbonate (4.76 g, 18.5 mmol), and triethylamine ($Et_3N$) (4.12 g, 40.8 mmol) in acetonitrile ($CH_3CN$) (50 mL) were stirred for 24 hours. The reaction mixture then was diluted with EtOAc (100 ml), washed several times with brine, then dried over anhydrous $Na_2SO_4$ and concentrated under reduced pressure to provide crude compound 15, which was purified by column chromatography to obtain the active carbonate 15. Yield (3.1 g, 75%), m.p 128–130° C. $^1$H NMR ($CDCl_3$, 200 MHz): δ 5.74 (d, 1H, J=5.1 Hz), 5.26 (m, 1H), 4 (m, 4H), 3.1 (m, 1H), 2.84 (s, 4H), 1.88–2.2 (m, 2H).

(3S,3aS,6aR)-Carbonic acid 2,5-dioxo-pyrrolidin-1-yl ester hexahydrofuro[2,3-b]furan-3-yl ester (16)

Compound 14 (500 mg, 2.9 mmol) and $K_2CO_3$ (802 mg, 5.8 mmol) in MeOH (25 mL) were stirred for 1 hour. The reaction mixture then was diluted with EtOAc (60 mL) and washed several times with brine (50 mL). The aqueous layer was extracted with EtOAc (40 mL), and the combined extracts were dried over anhydrous $Na_2SO_4$ and concentrated under reduced pressure. The residue was purified by a silica gel column to obtain a bicyclic alcohol.

The bicyclic alcohol, N,N'-disuccinimidyl carbonate (890 mg, 3.48 mmol), and $Et_3N$ (585 mg, 5.8 mmol) were subjected to same conditions as in the preparation of compound 15 to provide compound 16 (573 mg, 73%, two steps). $[α]^{25}_D$: +22.5°, c, 1.6, MeOH. $^1$H NMR ($CDCl_3$, 200 MHz): δ 5.76 (d, 1H, J=5.2 Hz) 5.25 (m, 1H), 3.9–4.3 (m, 4H), 3.14 (m, 1H), 2.85 (s, 4H), 1.9–2.2 (m, 2H).

Synthesis of Pyridyl Mixed Carbonates (18) and (20)

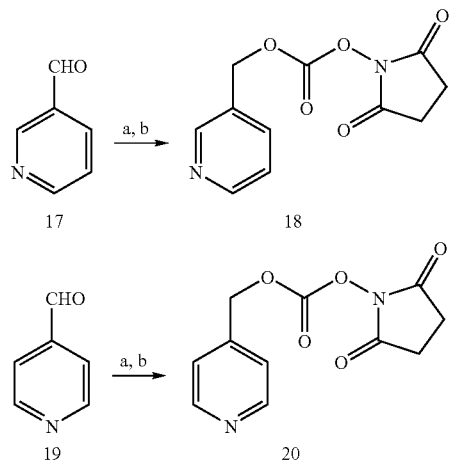

Key: (a) $NaBH_4$, MeOH, 0° C., 15 min.; (b) DSC, $Et_3N$, $CH_3CN$, 1 hour, 90% for two steps.

Carbonic acid 2,5-dioxo-pyrrolidin-1-yl ester pyridin-3-yl methyl ester (18)

To compound 17 (430 mg, 4 mmol) in MeOH (10 mL) at 0° C. was added $NaBH_4$ (279 mg, 8 mmol) in one portion. After 15 min., the reaction mixture was diluted with EtOAc (20 mL) and washed with brine (20 mL). The organic layer was dried over anhydrous $Na_2SO_4$, then concentrated under reduced pressure to obtain an alcohol, which was filtered through silica gel column, then concentrated.

The above alcohol, N,N'-disuccinimidyl carbonate (1.47 g, 5.76 mmol), and $Et_3N$ (606 mg, 6 mmol) in $CH_3CN$ (10 mL) were stirred for 1 hour. The reaction mixture then was diluted with EtOAc (20 mL) and washed several times with water, and dried over anhydrous $Na_2SO_4$. The crude product was purified by silica gel column to obtain compound 18 (900 mg, 90%, two steps). This carbonate was unstable and was used immediately.

Carbonic acid 2,5-dioxo-pyrrolidin-1-yl ester pyridin-4-yl methyl ester (20)

To compound 19 (400 mg, 3.7 mmol) in MeOH (10 mL) at 0° C. was added NaBH$_4$ (236 mg, 7.4 mmol) in one portion following the conditions used in the preparation of compound 18 to obtain an alcohol that was filtered through a silica gel column, then concentrated.

The alcohol, N,N'-disuccinimidyl carbonate (1.4 g, 5.5 mmol), and Et$_3$N (606 mg, 6 mmol) in CH$_3$CN (10 mL) were allowed to react under the same conditions used in the preparation of compound 18 to obtain compound 20 (824 mg, 88%, two steps). This carbonate also was unstable and was used immediately.

(3S)-Carbonic acid 2,5-dioxo-pyrrolidin-1-yl ester tetrahydrofuran-3-yl ester (22)

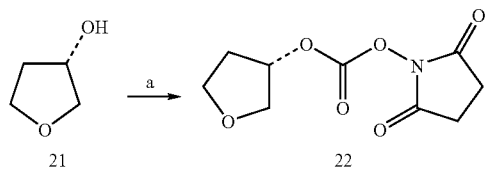

Key: (b) DSC, Et$_3$N, CH$_3$CN, 12 hours, 92%

Compound 21 (250 mg, 2.84 mmol), N,N'-disuccinimidyl carbonate (799 mg, 3.12 mmol), and Et$_3$N (431 mg, 4.27 mmol) in CH$_3$CN (5 mL) were stirred for 12 hours at room temperature. Then the reaction mixture was diluted with EtOAc (20 mL), washed with brine, then concentrated under reduced pressure to obtain compound 22 (595 mg, 92%) as a solid. M.P.: 97–99° C.

1-(3-Hydroxypropyl)-2-(tetrahydropyran-2-yloxy)-cyclopentanol (25)

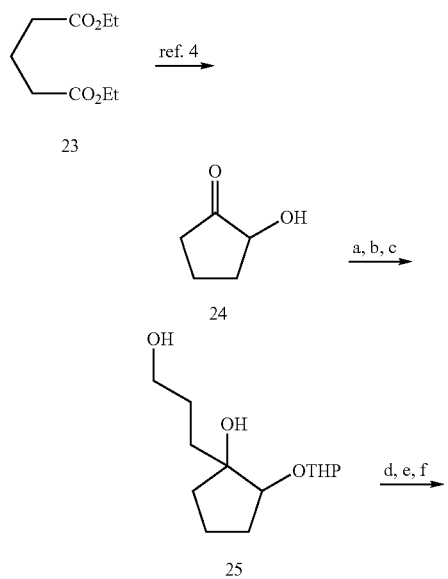

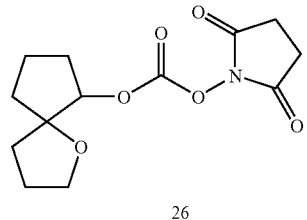

Key: (a) DHP, CH$_2$Cl$_2$, 1.5 hours 63%; (b) allyl magnesium bromide, THF, 0° C., 73%; (c) 9-BBN, THF, 12 hours, then MeOH, H$_2$O$_2$, NaOH, 650° C., 1 h 68%; (d) MsCl, Py, 12 hours; (e) TsOH, MeOH, 30 min. 60%; (f) DSC, Et$_3$N, CH$_3$CN, 12 hours, 40%.

Compound 24 (1.13 g, 13 mmol) and dihydropyran (DHP) (1.42 g, 16.9 mmol) in CH$_2$Cl$_2$ (25 mL) were stirred for 1.5 hours. Aq. NaHCO$_3$ (10 mL) was added, and the reaction mixture was extracted with CH$_2$Cl$_2$ (10 mL). The combined extracts were dried over anhydrous Na$_2$SO$_4$ and concentrated under reduced pressure. Purification of the crude product by silica gel column provided the THP-protected hydroxyketone (540 mg, 63%) as an oil. $^1$H NMR (CDCl$_3$, 200 MHz): δ 5.9 (m, 1H), 5.1 (m, 2H), 4.7 (m, 1H), 3.9 (m, 2H), 3.5 (m, 1H), 2.1–2.5 (m, 2H), 1.3–2.0 (m, 12H).

The ketone (500 mg, 2.7 mmol) in THF (10 mL) was cooled to 0° C., and allyl magnesium bromide (5.4 mL, 5.4 mmol) was added dropwise. After 3 hours at room temperature, the reaction mixture was treated with aq. NH$_4$Cl (10 mL), then diluted with EtOAc (20 mL). The organic layer was washed with brine and dried over anhydrous Na$_2$SO$_4$. Solvents were evaporated under reduced pressure and the crude product was purified by silica gel column to obtain mixture of diastereomers (443 mg, 73%) as an oil.

The mixture (260 mg, 1.15 mmol) and 9-BBN (9-borabicyclo[3.3.1]nonane) (9.2 mL, 4.6 mmol, 0.5M solution) in THF at 0° C. were stirred for 12 hours at room temperature. MeOH (0.3 mL), hydrogen peroxide (H$_2$O$_2$) (2.5 mL, 30%), NaOH (7 mL, 30%) were heated at 65° C. for 1 hour. After cooling to room temperature, the solvents were evaporated under reduced pressure and the crude product was purified by silica gel column to obtain compound 25 (191 mg, 68%) as an oil. $^1$H NMR (CDCl$_3$, 400 MHz): δ 4.7 (m, 1H), 3.8, 3.7, and 3.5 (three m, 5H), 2.5 (br s, 2H), 1.4–2 (m, 16H).

Carbonic acid 2,5-dioxo-pyrrolidin-1-yl ester 1-oxa-spiro[4.4]non-6-yl ester (26)

To the diol 25 (170 mg, 0.69 mmol) and pyridine (1 mL) was added methanesulfonyl chloride (MsCl) (103 mg, 0.9 mmol). The resulting mixture was stirred for 12 hours. Then the mixture was diluted with EtOAc (10 mL) and the organic layer was washed with brine, dried over anhydrous Na$_2$SO$_4$ and concentrated under reduced pressure. The crude cyclic ether was purified by silica gel column to obtain (111 mg, 71%) of the cyclic product. $^1$H NMR (CDCl$_3$, 400 MHz): 5.71 (m, 1H), 3.95 (m, 4H), 3.87 (m, 1H), 1.6–2 (m, 16H).

To the above ether (110 mg, 0.48 mmol) in MeOH (5 mL) was added p-toluenesulfonic acid (TsOH) (16 mg). After stirring for 30 min, the solvent was evaporated and the crude product was extracted with EtOAc (2×10 mL) and the organic layers were washed with brine (10 mL) and concentrated. Purification by silica gel column provided the spiro alcohol (41 mg, 60%) as an oil. $^1$H NMR (CDCl$_3$, 400 MHz): δ 4.1 (m, 1H), 3.7 (m, 2H), 1.5–2 (m, 10H).

The above spiro alcohol (27 mg, 0.19 mmol), N,N'-disuccinimidyl carbonate (52 mg, 0.204 mmol), Et$_3$N (25 mg, 0.25 mmol) in CH$_3$CN (5 mL) were stirred for 12 hours, following the same conditions as described for compound 22 to obtain compound 26 (22 mg, 40%). $^1$H NMR (CDCl$_3$, 200 MHz): δ 4.7 (m, 1H), 3.8 (m, 2H), 2.8 (s, 4H), 1.5–2.1 (m, 10H).

(2S)-Carbonic acid 2,5-dioxo-pyrrolidin-1-yl ester 2-oxo-thiazolidin-4-ylmethyl ester (29)

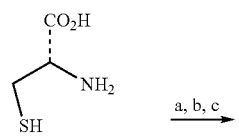

L-Cystine

27

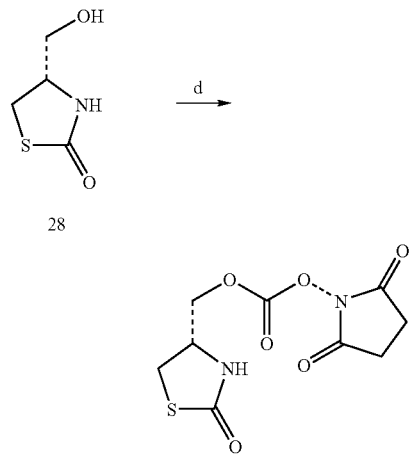

Key: (a) (COCl)$_2$, KOH, water, 2 hours; (b) EtOH, conc. HCl, 12 hours, 20%, two steps (c) NaBH$_4$, MeOH 3 hours (a) DSC, Et$_3$N, CH$_3$CN, 12 hours.

To compound 27 (2.42 g, 20 mmol) and potassium hydroxide (KOH) (40%, 5 mL) in water (30 mL), at 0° C., was added oxalyl chloride ((COCl)$_2$) (13 mL, 20%). After stirring for 2 hours, the biphasic layer was placed in separating funnel. The organic layer was discarded and the aqueous layer was washed with ether (10 mL), then acidified to pH 1 with 10% HCl (20 mL). The water then was evaporated under reduced pressure. The solid residue was extracted with hot ethanol (EtOH) (4×25 mL). The EtOH layer was concentrated to 20 mL and 0.2 mL of conc. HCl was added, followed by stirring for 12 hours. Ethanol then was evaporated and the crude product was extracted with EtOAc (2×25 mL). Concentration and purification by silica gel column provided the ethyl ester (668 mg, 20%, two steps) as an oil.

The ethyl ester was subjected to NaBH$_4$ (2–3 equiv.) reduction in MeOH for 2–3 hours at room temperature to obtain alcohol 28. Treatment of alcohol 28 with N,N-disuccinimidyl carbonate (2 equiv.) and Et$_3$N (4 equiv) in CH$_3$CN for 12–24 hours provided the mixed carbonate 29 in excellent yield.

Carbonic acid 2,5-dioxo-pyrrolidin-1-yl ester quinolin-4-ylmethyl ester (31)

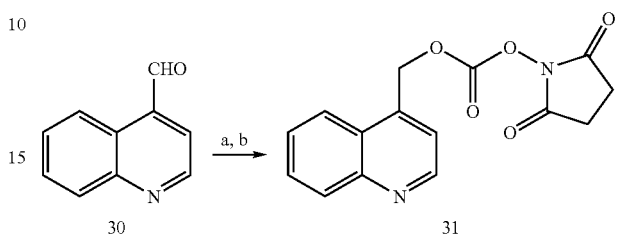

Key. (a) NaBH$_4$, MeOH, 0° C., 12 hours quantitative; (b) DSC, Et$_3$N, CH$_3$CN, 1 hour, 58% for two steps.

To compound 30 (300 mg, 2 mmol) in MeOH (5 mL) at 0° C. was added NaBH$_4$ (145 mg, 3.8 mmol). The resulting mixture was stirred for 12 hours. Standard workup and purification afforded the corresponding alcohol in quantitative yield.

The alcohol (50 mg, 0.31 mmol), N,N'-disuccinimidyl carbonate (1128 mg, 0.5 mmol), and Et$_3$N (63 mg, 0.63 mmol) in CH$_3$CN (2 mL) were stirred for 12 hours. After dilution with EtOAc (10 mL) and washing several times with brine (3×10 mL), the organic layer was dried over anhydrous Na$_2$SO$_4$ and concentrated under reduced pressure. The crude product was purified by silica gel chromatography to obtain compound 31 (52 mg, 58%) as solid. M.P.: 94° C. $^1$H NMR (CDCl$_3$, 400 MHz): δ 8.9 (d, 1H, J=4.4 Hz), 8.1 (d, 1H, J=8.5 Hz), 7.9 (d, 1H, J=8.3 Hz), 7.74 (m, 1H) 7.63 (m, 1H), 7.49 (d, 1H, J=4.3 Hz), 2.84 (s, 4H).

3-(Tetrahydropyran-2-yloxy)benzenesulfonyl chloride (33)

Key: (a) NaNO$_2$, H$_2$SO$_4$, H$_2$O, 0° C., 30 min.; (b) SOCl$_2$, DMF, reflux, 4 hours; (c) DHP, PPTS, CH$_2$Cl$_2$, 1 hour.

To a solution of compound 32 (5 g, 29 mmol) and sulfuric acid (H$_2$SO$_4$) (8.6 g, 88 mmol) in water (100 mL) at 0° C. was added sodium nitrite (NaNO$_2$) (2.2 g, 32 mmol) in portions. Then the reaction mixture was stirred for 30 minutes at room temperature, followed by boiling for 20 minutes. The red solution was concentrated under reduced pressure. The resulting crude product was extracted with hot EtOH (2×100 mL). All extractions were concentrated and treated with aq. NaOH solution until basic, and again concentrated to provided the sodium salt of the crude 3-hydroxybenzenesulfonic acid.

The salt (5.6 g, 29 mmol) and thionyl chloride (SOCl$_2$) (15 mL) were refluxed, and dimethylformamide (DMF) (0.1 mL) was added. Refluxing was continued for 4 hours. The reaction mixture then was cooled to room temperature, diluted with EtOAc (100 mL), and the organic layer washed with brine (2×50 mL). The combined organic layer was dried over anhydrous Na$_2$SO$_4$ and evaporated under reduced pressure. Purification of the resulting crude product by flash silica gel chromatography provided the hydroxybenzenesulfonyl chloride.

To the sulfonyl chloride (1 g, 5.2 mmol) and DHP (0.87 g, 10 mmol) in CH$_2$Cl$_2$ (25 mL) was added PPTS (pyridinium p-toluenesulfonate) (100 mg). The reaction mixture was stirred for 1 hour at room temperature. Then the reaction mixture was diluted with CH$_2$Cl$_2$ (20 mL) and the organic layer washed with aq. NaHCO$_3$ solution (20 mL) and brine (2×20 mL). The combined organic layer was dried over anhydrous Na$_2$SO$_4$ and evaporated under reduced pressure. Purification of the resulting crude product by flash silica gel chromatography provided compound 33 (670 mg, 56%). $^1$H NMR (CDCl$_3$, 200 MHz): δ 7.67 (m, 1H), 7.55 (m, 1H), 7.4 (m, 1H), 5.5 (m, 1H), 3.9 and 3.6 (two m, 2H), 1.5–2 (m, 6H).

Bisacetoxy Toluenesulfonyl Chlorides (35), (37), and (37b)

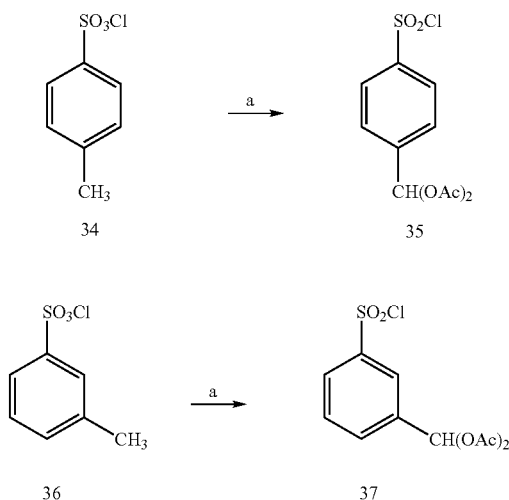

Key: (a) H$_2$SO$_4$, Ac$_2$O, AcOH, CrO$_3$, 0° C.-5° C., 33%.

Acetic acid acetoxy-(4-chlorosulfonylphenyl)methyl ester (35)

To compound 34 (2 g, 10.5 mmol), H$_2$SO$_4$ (2 g, 21 mmol), Ac$_2$O (8 mL), AcOH (8 mL) at 0° C.-5° C. was added CrO$_3$ (2.1 g, 21 mmol) in portions. The resulting reaction mixture was monitored by TLC. When the reaction was 50% complete, ice cold water (50 mL) was added, and the reaction mixture extracted with EtOAc. The organic layer was washed with brine (2×20 mL) and then aq. NaHCO$_3$ solution. The combined organic layer was dried over anhydrous Na$_2$SO$_4$ and evaporated under reduced pressure. Purification of the resulting crude product by flash silica gel chromatography provided compound 35 (1.09 g, 33%). $^1$H NMR (CDCl$_3$, 200 MHz): δ 8.0 (d, 2H, J=6.7 Hz), 7.78 (m, 3H), 2.15 (s, 6H).

Acetic acid acetoxy-(3-chlorosulfonylphenyl)methyl ester (37)

The same procedure was followed as for the preparation of compound 35 starting with m-toluenesulfonyl chloride (36). $^1$H NMR (CDCl$_3$, 200 MHz): δ 8.19 (m, 1H), 8.1 (m, 1H), 7.9 (m, 1H), 7.65 (m, 1H), 2.16 (s, 6H)

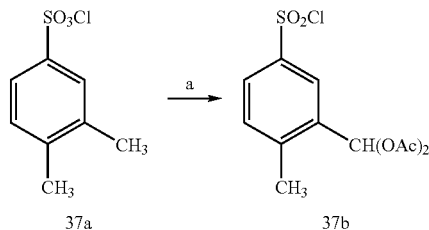

Acetic acid acetoxy-(3-chlorosulfonyl-2-methyl-phenyl)methyl ester (37b)

Following the same reaction under controlled conditions as described for compound 35, a mixture of isomers of compound 37b was obtained.

3,5-Bis-(tetrahydropyran-2-yloxy)benzenesulfonyl chloride (39)

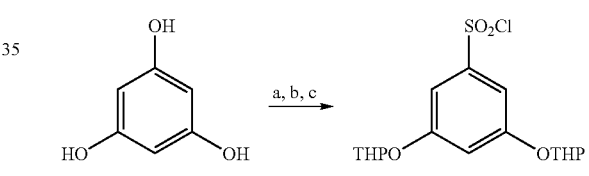

Key: (a) SO$_2$, NaHCO$_3$, 6 hours then compound 38, reflux, four days; (b) SO$_2$Cl, reflux, DMF, 50% for two steps; (c) DHP, PPTS, CH$_2$Cl$_2$, 1 hour, 67%.

To a suspension of NaHCO$_3$ (10 g, 119 mmol) in water (30 mL) was bubbled SO$_2$ gas. Bubbling continued until the NaHCO$_3$ was solubilized (6 hours). To this yellow solution (exit gases have a pH 1–2) was added phloroglucinol 38 (5 g, 30.8 mmol). The reaction mixture was refluxed for four days, then cooled to room temperature, the solvent evaporated, and the resulting solid was dried to obtain 3,5-dihydroxybenzenesulfonic acid.

The crude acid (500 mg, 2.35 mmol) and SO$_2$Cl (7 mL) were refluxed in the presence of DMF (0.1 mL) for 40 minutes. The resulting reaction mixture was extracted with EtOAc (50 mL) and the organic layer washed with brine (2×20 mL) and aq. NaHCO$_3$ solution. The combined organic layers were dried over anhydrous Na$_2$SO$_4$ then evaporated under reduced pressure. Purification of the resulting crude product by flash silica gel chromatography provided the dihydroxybenzene sulfonyl chloride (246 mg, 50%) as an oil. $^1$H NMR (CDCl$_3$, 200 MHz): δ 7.1 (m, 2H), 6.8 (m, 1H).

The dihydroxy compound (222 mg, 1.06 mmol), DHP (224 mg, 2.66 mmol) in CH$_2$Cl$_2$ (10 mL), and PPTS (50 mg) were stirred for 30 minutes at room temperature. Then the reaction mixture was diluted with CH$_2$Cl$_2$ (20 mL), and the organic layer washed with brine (2×20 mL). The combined organic layer was dried over anhydrous Na$_2$SO$_4$ and evaporated under reduced pressure. Purification of the resulting crude product by flash silica gel chromatography provided the compound 39 (237 mg, 67%) as an oil. $^1$H NMR (CDCl$_3$, 300 MHz): δ 7.3 (m, 2H), 7 (m, 1H), 5.4 (m, 2H), 3.8 and 3.6 (two m, 4H), 1.4–2 (m, 12 H).

5-Nitropyridine-3-sulfonyl chloride (42)

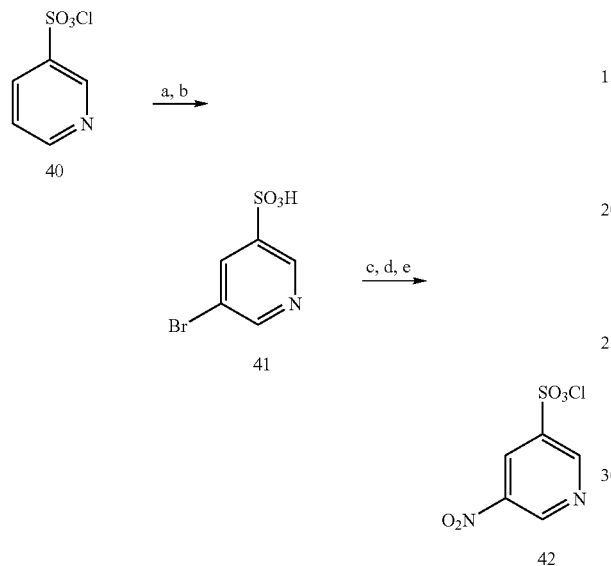

Key: (a) Br$_2$, 130° C., 8 hours; (b) H$_2$O, 100° C., 2 hours; (c) NH$_4$OH, CuSO$_4$.5H$_2$O, 170° C., 20 hours; (d) fuming H$_2$SO$_4$, H$_2$O$_2$, 0° C.-23° C., 40 hours; (e) PCl$_5$, POCl$_3$, reflux, 6 hours, 45% for five steps.

5-Bromopyridine-3-sulfonic acid (41)

Compound 40 (7 g, 35 mmol) and bromine (6.7 g, 42 mmol) in a sealed tube were heated at 130° C. for 8 hours on oil bath. After cooling to room temperature, water (70 mL) was added, and the reaction mixture heated again at 100° C. for 2 hours. After cooling, acetone (60 mL) was added and resulting solid was filtered, and dried to obtain compound 41 as crude product white solid. $^1$H NMR (dMSO-d$_6$, 300 MHz): δ 9.3 (br s, 1H), 8.8 (m, 2H), 8.2 (m, 1H).

5-Nitropyridine-3-sulfonyl chloride (42)

The acid 41 (4.5 g, 19 mmol), ammonium hydroxide (NH$_4$OH) (15 mL, 28%), and copper sulfate (CuSO$_4$.5H$_2$O) (470 mg, 1.9 mmol) were heated at 170° C. in a sealed tube for 20 hours. After cooling, water (5 mL) was added followed by sodium sulfide (Na$_2$S.9H$_2$O) (450 mg). Evaporation of water gave the crude aminopyridinesulfonic acid.

Fuming H$_2$SO$_4$ (30 mL) was placed in a flask cooled to 0° C. Hydrogen peroxide (H$_2$O$_2$) (14 mL, 30%) was carefully added. Then, the above crude sulfonic acid (2.8 g, 16 mmol) in H$_2$SO$_4$ (8 mL) was added to the above mixture. The resulting solution was stirred at room temperature, for 40 hours, and then poured into ice water-containing sodium carbonate (Na$_2$CO$_3$). Sufficient Na$_2$CO$_3$ was added to make the solution basic, which was acidified again to pH 1–2. The resulting solution was concentrated to minimum volume (20 mL). The precipitated NaCl was filtered, and the filtrate was concentrated. The resulting solid was extracted with MeOH (3×50 mL). The combined MeOH extractions were concentrated to 20 mL, and acetone (80 mL) was added. The solid obtained was filtered and dried to obtain nitropyridine sulfonic acid.

This acid (1.7 g, 7 mmol) and phosphorus pentachloride (PCl$_5$) (1.7 g, 8 mmol) in POCl$_3$ (50 mL) were refluxed for 6 hours. After cooling to room temperature, the solids were filtered, and the filtrate concentrated. The oily residue was diluted with EtOAc (100 mL) and the organic layer washed with brine (2×20 mL). The combined organic layer was dried over anhydrous Na$_2$SO$_4$ and evaporated to obtain compound 42 (730 mg, 45%) as an oil. $^1$H NMR (CDCl$_3$, 400 MHz): δ 9.15 (m, 1H), 9.02 (m, 1H), 8.43 (m, 1H).

4-Fluoro-3-nitrobenzenesulfonyl chloride (44)

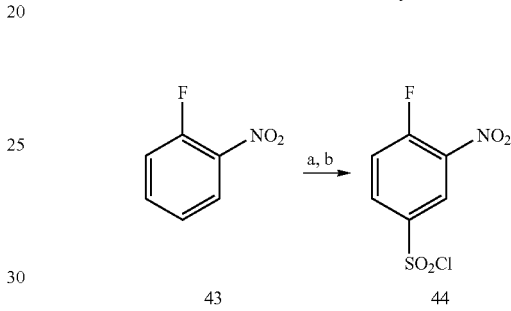

Key: (a) fuming H$_2$SO$_4$, 60° C., 30 min, quantitative; (b) PCl$_5$, POCl$_3$, reflux, 6 hours, quantitative.

To compound 43 (7 g, 5 mmol) was carefully added fuming H$_2$SO$_4$ (60 mL). The resulting mixture was heated to 60° C. for 30 minutes. Then, the hot mixture was slowly and very carefully poured into beaker containing potassium chloride (KCl) (30 g) and ice. The resulting white solid obtained was recrystallized from hot water to give 4-fluoro-3-nitrobenzenesulfonic acid in quantitative yield.

The acid (2 g, 7.7 mmol) and phosphorus pentachloride (PCl$_5$) (1.8 g, 7.5 mmol) in phosphorus oxytrichloride (POCl$_3$) (60 mL) were refluxed for 6 hours. The resulting mixture was cooled to room temperature, and concentrated. Crushed ice was added to the oily residue. The solid was filtered and washed with water (2×50 mL), dried to obtain compound 44 (quantitative). $^1$H NMR (CDCl$_3$, 500 MHz): δ 8.8 (m, 1H), 8.36 (m, 1H), 7.6 (m, 1H).

Synthesis of Pyrrolidine Amines (46) and (50)

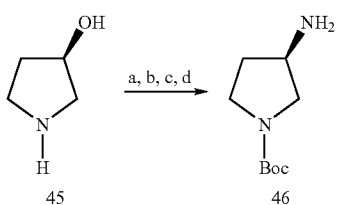

Key: (a) Boc$_2$O, CH$_2$Cl$_2$, 2 hours; (b) p-TsCl, Et$_3$N, DMAP, CH$_2$Cl$_2$, 8 hours, quantitative; (c) NaN$_3$, DMF, 80° C., 4 hours; (d) H$_2$, Pd—C (10%); MeOH, 5–6 hours, 92%.

(3R)-3-Amino-pyrrolidine-1-carboxylic acid tert-butyl ester (46)

Compound 45 (775 mg, 9 mmol) and Boc₂O (2:33 g, 10.6 mmol) in CH₂Cl₂ (40 mL) were stirred for 2 hours at room temperature. Then the reaction mixture was diluted with CH₂Cl₂ (20 mL), and the organic layer washed with brine (2×20 mL). The combined organic layer was dried over anhydrous Na₂SO₄ and concentrated. Purification of the resulting crude product by flash silica gel chromatography provided N-Boc pyrrolidnol as an oil.

This alcohol (7.3 g, 39 mmol), p-TsCl (8.2 g, 43 mmol), Et₃N (9.8 g, 97 mmol), DMAP (240 mg) in CH₂Cl₂ (100 mL) were stirred for 8 hours at room temperature. Then the reaction mixture was washed with brine (100 mL). The organic layer was dried over anhydrous Na₂SO₄ and concentrated. Purification of the resulting crude product by flash silica gel chromatography provided the ester in quantitative yield.

This sulfonate ester (12.5 g, 38 mmol) and NaN₃ (3.7 g, 57 mmol) in DMF (70 mL) were heated at 80° C. for 4 hours. After cooling to room temperature, the reaction mixture was diluted with EtOAc (200 mL). The organic layer washed with brine (2×100 mL). The combined organic layer was dried over anhydrous Na₂SO₄ and concentrated. Purification of the resulting crude product by flash silica gel chromatography provided the azido compound, which was hydrogenated in presence of Pd—C (10%) in MeOH for 5–6 hours to obtain compound 46 (7.43 g, 92%) as an oil. ¹H NMR (CDCl₃, 300 MHz): δ 4.12 (m, 1H), 3.5 (m, 4H), 2 (m, 2H), 1.45 (s, 9H).

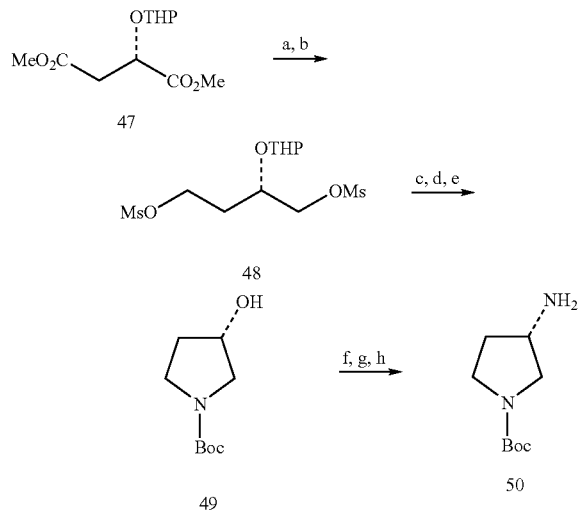

Key: (a) LiAlH₄, THF, 55° C., 24 hours, 55%; (b) MsCl, Et₃N, CH₂Cl₂, 0° C., 45 min, 90%; (c) BnNH₂, reflux, 36 hours; (d) Pd(OH)₂, Boc₂O, Et₃N, THF, 8 hours, 85%; (e) TsOH, MeOH, 1 hour 96%; (f) MsCl, Et₃N, 0° C., CH₂Cl₂, 10 min.; (g) NaN₃, DMF, 80° C., 6 hours; (h) H₂, Pd—C (10%), MeOH, 5–6 hours, 81% for two steps.

Methanesulfonic acid 4-methanesulfonyloxy-3-(tetrahydropyran-2-yloxy)butyl ester (48)

To compound 47 (8.4 g, 34 mmol) in THF (130 mL) was added lithium aluminum hydride (LiAlH₄) (7.6 g, 206 mmol) in portions. The resulting mixture was heated at 55° C. for 24 hours. After cooling to room temperature, H₂O (7.2 ml), NaOH (7.2 mL, 20%), and H₂O (14.4 mL) were added sequentially and the mixture was stirred for 12 hours. The solid was filtered and the filtrate concentrated. Purification of the resulting crude product by flash silica gel chromatography provided the diol (3.66, 55%) as an oil. ¹H NMR (CDCl₃, 400 MHz): δ 4.6 (m, 1H), 4 (m, 1H), 3.5–3.9 (m, 6H), 2.92 (s, 2H), 1.4–1.82 (m, 8H), (s, 9H).

To that diol (3.66 g, 19 mmol) and Et₃N (5.23 g, 51 mmol) in CH₂Cl₂ (80 mL) at 0° C. was added MsCl (5.48 g, 48 mmol). The resulting reaction mixture was stirred for 45 minutes at room temperature, then the reaction mixture was diluted with CH₂Cl₂ (50 mL) and the organic layer washed with brine (2×20 mL). The combined organic layer was dried over anhydrous Na₂SO₄ and concentrated. Purification of the resulting crude product by flash silica gel chromatography provided the compound 48 (6 g, 90%) as an oil. ¹H NMR (CDCl₃, 300 MHz): δ 4.6 (m, 1H), 4.2–4.4 (m, 4H), 3.8–4.1 (m, 2H), 3 (m, 6H.), 2 (m, 2H), 1.75 (m, 2H), 1.45 (m, 4H).

3-Hydroxypyrrolidine-1-carboxylic acid tert-butyl ester (49)

Compound 48 (6 g, 17 mmol) and BnNH₂ (6.5 g, 60 mmol) in THF (150 mL) were refluxed for 12 hours. Then, benzylamine (BnNH₂) (6.5 g, 60 mmol) again was added and refluxing was continued for 24 hours, followed by cooling to room temperature. The reaction mixture was diluted with EtOAc (100 mL) and the organic layer washed with brine (2×20 mL). The combined organic layer was dried over anhydrous Na₂SO₄ and concentrated. Purification of the resulting crude product by flash silica gel chromatography provided the pyrrolidine compound (4.4 g) as an oil. ¹H NMR (CDCl₃, 300 MHz): δ 7.2 (m, 5H), 4.55 (m, 1H), 4.38 (m, 1H), 3.8 (m, 1H), 3.6 (m, 2H), 3.41 (m, 1H), 2.4–2.7 (m, 4H), 2.1 (m, 1H), 1.4–1.9 (m, 7H).

This amino compound (4.4 g, 17 mmol) in MeOH (50 mL) was hydrogenated over Pd(OH)₂ (1 g, 20%) for 18 hours. Boc₂O (4.4 g, 20 mmol) and Et₃N (3 g, 21 mmol) were added and stirred for 8 hours at room temperature. The reaction mixture was diluted with EtOAc (100 mL) and the organic layer washed with brine (2×20 mL). The combined organic layer was dried over anhydrous Na₂SO₄ and concentrated. Purification of the resulting crude product by flash silica gel chromatography provided the Boc compound (3.9 g, 85%).

To this THP ether (3.9 g, 14.3 mmol) in MeOH (60 mL) was added TsOH (140 mg), followed by stirring for 1 hour at room temperature Then the reaction mixture was diluted with EtOAc (100 mL) and the organic layer washed with brine (2×20 mL). The combined organic layer was dried over anhydrous Na₂SO₄ and concentrated. Purification of the resulting crude product by flash silica gel chromatography provided compound 49 (2.56, 96%). [α]$_D^{25}$: +24.2°, c, 2.1; CHCl₃. ¹H NMR (CDCl₃, 300 MHz): δ 4.4 (m, 1H), 3.4 (m, 3H), 3.3 (m, 1H), 1.89 (m, 2H), 1.4 (m, 9H).

(3S)-3-Aminopyrrolidine-1-carboxylic acid tert-butyl ester (50)

To compound 49 (g, 10.7 mmol) and Et₃N (2.15 g, 21 mmol) in CH₂Cl₂ (50 mL) at 0° C. was added MsCl (1.46 g, 12.8 mmol), followed by stirring for 10 minutes room temperature. Then the reaction mixture was diluted with CH₂Cl₂ (50 mL) and the organic layer washed with brine (2×50 mL). The combined organic layer was dried over anhydrous Na$_2$SO$_4$ and concentrated. Purification of the resulting crude product by flash silica gel chromatography provided the dimesolate compound (2.9 g) as an oil.

This mesolate (2.9 g, 11 mmol) and NaN$_3$ (4 g, 16 mmol) in DMF (20 mL) were stirred for 6 hours at 60° C. Then the reaction mixture was diluted with EtOAc (50 mL) and the organic layer washed with brine (2×20 mL). The combined organic layer was dried over anhydrous Na$_2$SO$_4$ and concentrated. Purification of the resulting crude product by flash silica gel chromatography provided an azido compound, which was hydrogenated as described above to provide compound 50 (1.87 g, 81%) as an oil. $^1$H NMR (CDCl$_3$, 400 MHz): δ 4.12 (m, 1H), 3.4 (m, 4H), 2 (m, 2H), 1.45 (s, 9H).

3-Aminoazetidine-1-carboxylic acid tert-butyl ester (53)

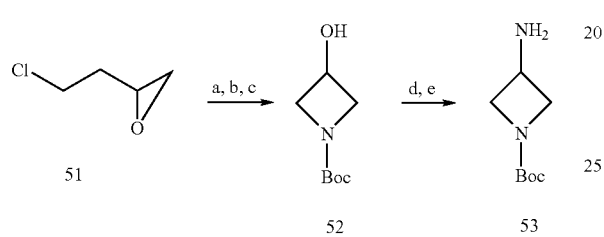

Key: (a) benzhydrylamine, MeOH, 72 hours, 23° C., then reflux 72 hours; (b) MeOH, EtOH (1:1), Pd(OH)$_2$ (20%), 12 hours; (c) Boc$_2$O, sat. NaHCO$_3$, 24 hours; (d) MsCl, Et$_3$N, CH$_2$Cl$_2$, 1 hour, 83%; (e) NaN$_3$, DMF, 70° C., 72 hours, then H$_2$, Pd—C (10%), MeOH, 5–6 hours, quantitative.

3-Hydroxyazetidine-1-carboxylic acid tert-butyl ester (52)

2-(2-Chloroethyl)oxirane (51) (5 g, 54 mmol) and benzhydrylamine (10 g, 53 mmol) in MeOH (25 mL) were allowed to stand for 72 hours, then refluxed for 72 hours. The reaction mixture was cooled to room temperature, then concentrated to obtain a crude product solid.

The crude product (1.7 g, 7 mmol), in MeOH and EtOH (10+10 mL), was hydrogenated in presence of Pd(OH)$_2$ (500 mg, 20%) for 12 hours. The reaction mixture then was filtered, and Boc$_2$O (2.3 g, 10 mmol) and sat. NaHCO$_3$ solution (10 mL) were added, followed by stirring for 24 hours at room temperature. Then the reaction mixture was diluted with EtOAc (50 mL) and the organic layer washed with brine (2×20 mL). The combined organic layer was dried over anhydrous Na$_2$SO$_4$ and concentrated. Purification of the resulting crude product by flash silica gel chromatography provided compound 52 (1.35 g). $^1$H NMR (CDCl$_3$, 300 MHz): δ 4.5 (m, 1H), 4.04 (m, 2H), 3.7 (dd, 2H), 1.45 (s, 9H).

3-Aminoazetidine-1-carboxylic acid tert-butyl ester (53)

To compound 52 (928 mg, 5.3 mmol) and Et$_3$N (1 g, 10.7 mmol) in CH$_2$Cl$_2$ (20 mL) was added MsCl (733 mg, 6.4 mmol), followed by stirring for 1 hour at room temperature. Then the reaction mixture was diluted with CH$_2$Cl$_2$ (20 mL) and the organic layer washed with brine (20 mL). The combined organic layer was dried over anhydrous Na$_2$SO$_4$ and concentrated. Purification of the resulting crude product by flash silica gel chromatography provided the mesolate compound (1.11 g, 83%) as an oil.

The mesolate (1.11 g, 4.4 mmol) and NaN$_3$ (574 mg, 8.8 mmol) in DMF (10 mL) were stirred for 72 hours at 72° C. Then the reaction mixture was diluted with EtOAc (20 mL), and the organic layer was washed with brine (2×20 mL). The combined organic layer was dried over anhydrous Na$_2$SO$_4$ and concentrated. Purification of the resulting crude product by flash silica gel chromatography provided the azido compound, which was subsequently converted to compound 53 in quantitative yield by hydrogenation. $^1$H NMR (CDCl$_3$, 300 MHz): δ 4.15 (m, 3H), 3.82 (m, 2H), 1.4 (s, 9H).

3-Aminotetrahydrofuran (55)

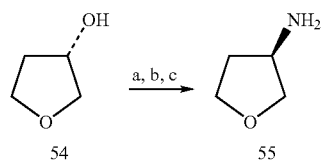

Key: (a) MsCl, Et$_3$N, CH$_2$Cl$_2$, 1 hour; (b) NaN$_3$, DMF, 70° C., 72 hours; (c) H$_2$, Pd—C (10%), MeOH, 5–6 hours, quantitative.

The same reaction conditions used to prepare compound 53 were used to obtain compound 55 in quantitative yield. A satisfactory NMR was obtained for this compound.

3,5-Bis-(tetrahydropyran-2-yloxy)benzenesulfonyl chloride (57)

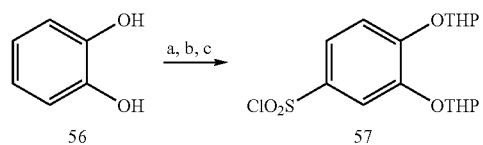

Key: (a) aminosulfonic acid, 180–200° C., 1.5 hours, 40%; (b) SO$_2$Cl, reflux, DMF, 1 hour, 44%; (c) DHP, PPTS, CH$_2$Cl$_2$, 2 hours, 56%.

Compound 56 (25 g, 220 mmol) was heated at 180–200° C., then aminosulfonic acid (9.7 g, 100 mmol) was added portion wise. The resulting slurry was stirred and heated for 1.5 hours, then cooled, and dissolved in minimum amount of water. The clear solution was treated with decolorizing charcoal and filtered. The filtrate was washed with ether (2×50 mL), and the aqueous layer concentrated to minimum volume (20 mL). Upon standing crystals separated which were dried to obtain 3,4-dihydroxybenzene sulfonic acid (7.56 g, 40%). M.P.: 254–255° C., lit. 260° C.

To the above sulfonic acid (7 g, 38 mmol), was added SOCl$_2$ (15 mL) and DMF (0.1 mL) following the same conditions described above for compound 39 to obtain the sulfonyl chloride (3.6 g, 44%) as an oil.

This chloride (3.5 g, 16.8 mmol), DHP (3.1 g, 37 mmol) and PPTS (200 mg) in CH$_2$Cl$_2$ (50 mL) were stirred for 2 hours at room temperature. Then the reaction mixture was diluted with CH$_2$Cl$_2$ (20 mL) and the organic layer washed with NaHCO$_3$ (20 mL), then brine (2×20 mL). The combined organic layer was dried over anhydrous Na$_2$SO$_4$ and concentrated. Purification of the resulting crude product by flash silica gel chromatography provided compound 57 (3.2 g, 56%) as an oil. $^1$H NMR (CDCl$_3$, 200 MHz): δ 8 (d, 1H, J=2 Hz), 7.63 (m, 1H), 7.25 (d, 1H, J=8.4 Hz), 5.58 (m, 2H,), 3.4–4.2 (m, 4H), 1.4–2.2 (m, 12H).

Synthesis of Mixed Carbonates of Spirocycles

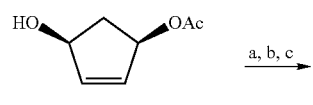

1

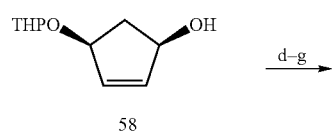

58

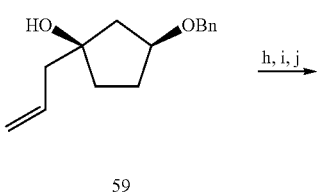

59

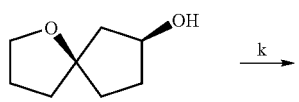

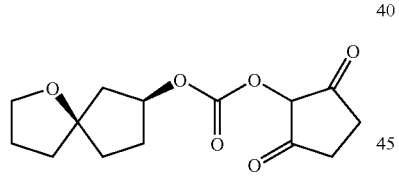

61

Key: (a) DHP, PPTS, CH$_2$Cl$_2$, 4–5 hours; (b) K$_2$CO$_3$, MeOH, 30 min.; (c) Rh/Al$_2$O$_3$, H$_2$, EtOAc, 8–12 hours; (d) BnBr, NaH, TBAI, THF, 12–14 hours; (e) p-TsOH, MeOH, 20–30 min.; (f) PCC, CH$_2$Cl$_2$, MS (4 Å), 12 hours; (g) allylmagnesium bromide, THF, 0° C., 30 min.; (h) 9BBN, THF, room temperature 24 hours; (i) MsCl, Py, 24 hours; (j) H$_2$, Pd(OH)$_2$, EtOAc, 12 hours; (k) N,N-disuccinimidyl carbonate, Et$_3$N, acetonitrile, 12–24 hours.

Same conditions were followed for the synthesis of mixed carbonate 63.

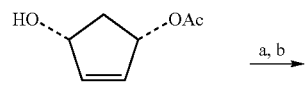

-continued

TBSO OAc

62

63

Variation of p2 Ligands of the 3-hydroxybenzene Sulfonamide Isostere

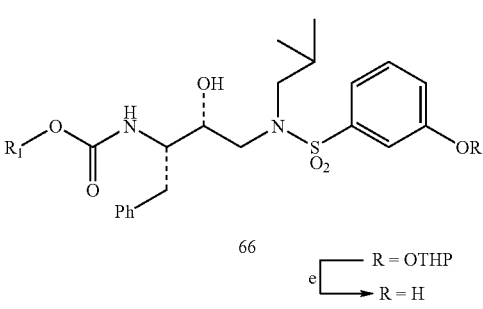

Key: (a) Isobutylamine, isopropanol, reflux, 6 hours; (b) sulfonyl chloride 33, CH$_2$Cl$_2$, aq. NaHCO$_3$ sol., 12 hours; (c) Pd—C (10%), H$_2$, MeOH, 6–8 hours; (d) various mixed carbonates, Et$_3$N, CH$_2$Cl$_2$, 4–6 hours.

| No. | | Activity | |
|---|---|---|---|
| | | IC$_{50}$ (nM) | Ki (nM) |
| 75 | | 6.7 | 2.1 |
| 78 | | 1.6 | 53 |
| 79 | | 5.5 | 1.7 |

Compound 75: Compound 66 (0.12 mmol), compound 26 (0.14 mmol), and Et$_3$N (2 equiv.) in CH$_2$Cl$_2$ (1 mL) were stirred for 6 hours at room temperature. Then the reaction mixture was diluted with CH$_2$Cl$_2$ (10 mL) and the organic layer washed with brine (2×20 mL). The combined organic layer was dried over anhydrous Na$_2$SO$_4$ and concentrated. Purification of the resulting crude product by flash silica gel chromatography provided the THP ether.

The THP ether (0.011 mmol) and p-TsOH (2 mg) in MeOH (0.5 mL) were stirred for 10 minutes at room temperature. Then the reaction mixture was diluted with EtOAc (10 mL) and the organic layer washed with brine (2×20 mL). The combined organic layer was dried over anhydrous Na$_2$SO$_4$ and concentrated. Purification of the resulting crude product by flash silica gel chromatography provided compound 75 (5 mg) as a solid. $^1$H NMR (CDCl$_3$, 400 MHz): δ 8.3 (s, 1H), 7–7.4 (m, 9H), 5.05 (m, 1H), 4.68 (d, 1H, 4Hz), 3.8–4 (m, 3H), 3.6 (m, 1H), 2.6–3.1 (m, 6H), 1.5–2.1 (m, 1H), 0.93 (m, 6H).

Compound 78: Compound 66 (22 mg, 0.055 mmol), compound 4 (18 mg, 0.066 mmol), and Et$_3$N (2 equiv.) in CH$_2$Cl$_2$ (1 mL) were subjected to same conditions as described above for compound 75 to obtain compound 78 (23 mg) as a solid. $^1$H NMR (CDCl$_3$, 400 MHz): δ 7.2–7.5 (m, 9H), 5.5 (m, 1H), 4.86 (m, 2H), 4.4 (m, 1H), 3.6–3.8 (m, 6H), 2.8–3.2 (m, 6H), 2.6 (m, 1H), 1.4–2.1 (m, 13H), 0.96 (ABq, 6H, J=6.5 Hz).

Compound 79: Compound 78 (19 mg, 0.03 mmol) and TsOH (6 mg) in MeOH (1 mL) were subjected to same conditions as described above for compound 75 to obtain compound 79 (12 mg) as a solid. $^1$H NMR (CDCl$_3$, 400 MHz): δ 8.9 (s, 1H), 7.1–7.4 (m, 8H), 7.03 (d, 1H, J=6.9 Hz), 5.29 (m, 1H), 5 (d, 1H, J=8.8 Hz), 4.6 (t, 1H, J=6.1 Hz), 4.1 (m, 1H), 3.85–4 (m, 2H), 3.75 (q, 1H, J=7.9 Hz), 3.53 (dd, 1H, J=3 Hz, 15 Hz), 3.1 (m, 1H), 2.91 (dd, 1H, J=5.2 Hz, 14 Hz), 2.82 (m, 1H), 2.65 (dd, 1H, J=7.6 Hz, 14.9 Hz), 2.59 (dd, 1H, J=4.6 Hz, 13.1 Hz), 1.7–2.2 (m, 7H), 0.98 and 0.88 (ABq, 6H, J=6.4 Hz).

Variation of p2 Ligands of 2,4-dihydroxybenzene Sulfonamide Isostere

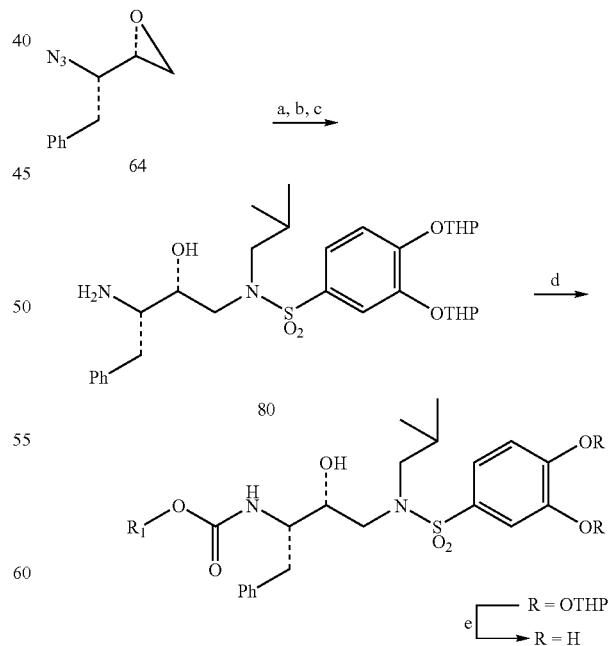

Key: a) Isobutylamine, isopropanol, reflux, 6 hours; b) sulfonyl chloride 39, CH$_2$Cl$_2$, aq. NaHCO$_3$ sol., 12 hours; c) Pd—C (10%), H$_2$, MeOH, 6 hours; d) mixed carbonate, Et$_3$N, CH$_2$Cl$_2$, 2–3 hours; e) p-TsOH, MeOH, 5–15 minutes.

| No. | | Activity | |
|---|---|---|---|
| | | IC$_{50}$ (nM) | Ki (nM) |
| 87 | *(structure)* | 30 | 9.3 |
| 88 | *(structure)* | 3.9 | 1.2 |

Compound 87: Compound 80 (55 mg, 0.9 mmol), compound 4 (25 mg, 0.9 mmol), and Et$_3$N (2.0 equiv.) in CH$_2$Cl$_2$ (2 mL) were subjected to same conditions as described above for compound 75 to obtain compound 87 (26 mg) as a solid. $^1$H NMR (CDCl$_3$, 400 MHz): δ 7.2–7.5 (m, 8H), 5.56 (m, 2H), 4.86 (m, 2H), 4.3 (m, 1H), 3.5–4 (m, 8H), 2.8–3.2 (m, 6H), 2.6 (m, 1H), 1.6–2.1 (m, 19H), 0.86 (ABq, 6H, J=6.3 Hz).

Compound 88: Compound 87 (21 mg, 0.028 mmol) and p-TsOH (10 mg) in MeOH (1 mL) were subjected to same conditions as described above for compound 75 to obtain compound 88 (8 mg) as a solid. M.P.: 80–82° C. [α]$_D^{25}$: +9.7°, c, 0.82, MeOH. $^1$H NMR (CDCl$_3$, 400 MHz): δ 9.5 (s, 1H), 7.2 (m, 7H), 7 (d, 1H, J=8.3 Hz), 6 (s, 1H), 5.03 (t, 1H, J=5.2 Hz), 4.91 (d, 1H, J=8.9 Hz), 4.58 (t, 1H, J=6.2 Hz), 4.18 (dd, 1H, J=6.5 Hz, 7.7 Hz), 3.9 (m, 2H), 3.82 (m, 1H), 3.51 (dd, 1H, J=3.5 Hz, 15 Hz), 3.25 (m, 1H), 3.1 (m, 2H), 2.95 (dd, 1H, J=8.2 Hz, 14 Hz), 2.87 (m, 1H), 2.58 (m, 1H), 2.49 (dd, 1H, J=4.3 Hz, 13 Hz), 1.9–2.2 (m, 4H), 1.75 (d, 1H, J=14.2 Hz), 1.02 and 0.87 (ABq, 6H, 6.4 Hz).

Variation of p2 Ligands of 3,5-dihydroxybenzene Sulfonamide Isostere

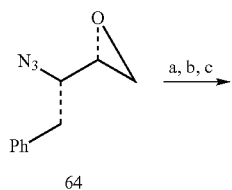

64

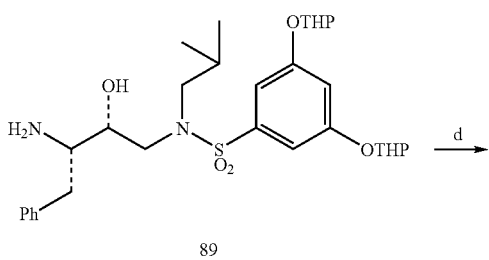

89

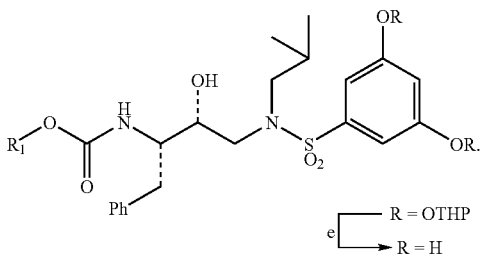

Key: a) Isobutylamine, isopropanol, reflux, 6 hours; b) sulfonyl chloride 39. aqueous NaHCO$_3$, CH$_2$Cl$_2$, 12 hours; c) Pd—C (10%), H$_2$, MeOH, 6 hours; d) various mixed carbonates, Et$_3$N, CH$_2$Cl$_2$, 6 hours; e) p-TsOH, MeOH, 5–15 min.

| No. | Structure | Activity IC$_{50}$ (nM) | Ki (nM) |
|---|---|---|---|
| 99 | (compound with OTHP groups) | 3.9 | 1.2 |
| 100 | (compound with OH groups) | 247 | 77 |

Compound 99: Compound 89 (102 mg, 0.178 mmol), compound 4 (48 mg, 0.178 mmol), and Et$_3$N (2.0 equiv.) in CH$_2$Cl$_2$ (5 mL) were subjected to same conditions as described above for compound 75 to obtain compound 99 (110 mg) as a solid. $^1$H NMR (CDCl$_3$, 400 MHz): δ 7.25 (m, 5H), 7.09 (s, 2H), 6.96 (s, 1H), 5.43 (m, 2H), 4.78 (m, 2H), 4.39 (m, 1H), 3.9 (m, 5H), 3.65 (m, 3H), 3.15 (m, 2H), 3.05 (m, 1H), 2.87 (m, 2H), 2.6 (m, 1H), 2.02, 1.85 and 1.7 (three m, 18H), 0.92 and 0.87 (ABq, 6H, J=6.4 Hz).

Compound 100: Compound 99 (88 mg, 0.12 mmol) and TsOH (20 mg) in MeOH (5 mL) were subjected to same conditions as described above for compound 75 to obtain compound 100 as a solid. $^1$H NMR (CDCl$_3$, 200 MHz): δ 8.08 (s, 2H), 7.23 (m, 5H), 6.78 (s, 2H), 6.54 (s, 1H), 5.21 (d, 1H, J=8 Hz), 4.93 (m, 1H), 4.52 (m, 1H), 3.8–4.1 (m, 3H), 3.68 (dd, 1H, J=7 Hz, 14.5 Hz), 3.5 (m, 2H), 2.5–3.1 (m, 7H), 1.5–2.2 (m, 7H), 0.92 and 0.89 (ABq, 6H, J=6.4 Hz).

Incorporation of High Affinity p2 Ligands to New Class of Hydroxyethylamine Isostere

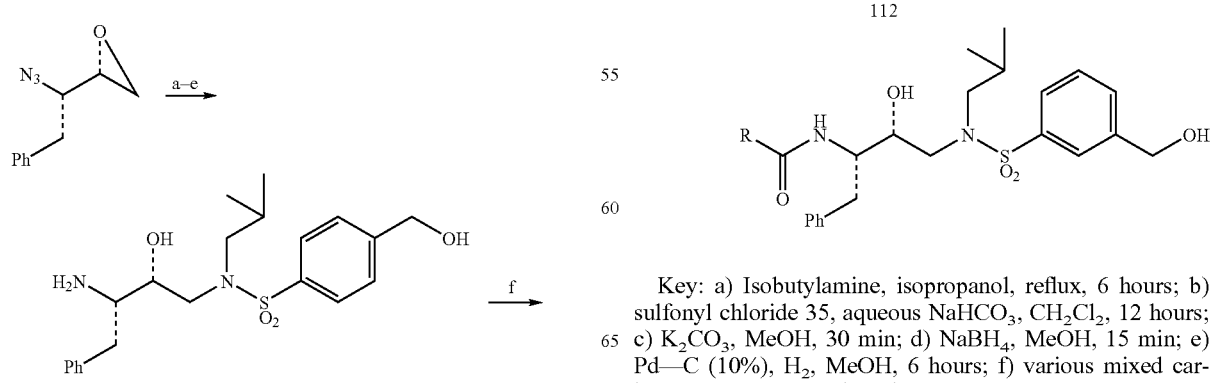

Key: a) Isobutylamine, isopropanol, reflux, 6 hours; b) sulfonyl chloride 35, aqueous NaHCO$_3$, CH$_2$Cl$_2$, 12 hours; c) K$_2$CO$_3$, MeOH, 30 min; d) NaBH$_4$, MeOH, 15 min; e) Pd—C (10%), H$_2$, MeOH, 6 hours; f) various mixed carbonates, Et$_3$N, CH$_2$Cl$_2$, 6 hours.

| No. | | Activity IC$_{50}$ (nM) |
|---|---|---|
| 110 | (structure) | 1.3 |
| 111 | (structure) | 2.9 |
| 113 | (structure) | 4.0 |
| 114 | (structure) | 1.1 |

Compound 110: Compound 101 (70 mg, 0.17 mmol), compound 4 (46 mg, 0.17 mmol), and Et$_3$N (2.0 equiv.) in CH$_2$Cl$_2$ (10 mL) were subjected to same conditions as described above for compound 75 to obtain compound 110 (75 mg) as a solid. M.P.: 110–112° C. $[\alpha]_D^{25}$: +10°, c, 0.72, CHCl$_3$. $^1$H NMR (CDCl$_3$, 400 MHz): δ 7.75 (d, 2H), 7.5 (d, 2H), 4.85 (s, 1H), 4.76 (m, 3H), 4.37 (m, 1H), 3.6–3.9 (m, 4H), 2.8–3.15 (m, 6H), 2.6 (m, 1H), 2 (m, 2H), 1.8 (m, 2H), 1.69, 1.55, and 1.44 (three m, 3H), 0.89 (ABq, 6H, J=6.4 Hz).

Compound 111: Compound 101 and compound 6 were subjected to conditions previously described above for compound 75 to obtain 111 as a solid: $^1$H NMR (CDCl$_3$, 300 MHz): δ 7.76 (d, 2H, J=8 Hz), 7.42 (d, 2H, J=8.1 Hz), 7.2 (m, 5H), 4.8 (m, 1H), 4.77 (s, 2H), 4.66 (m, 1H), 4.35 (m, 1H), 3.6–3.82 (m, 4H), 2.71–3.05 (m, 6H), 2.6 (m, 1H), 1.4–2.1 (m, 6H), 0.82 (ABq, 6H, J=6.4 Hz).

Compound 113: Compound 112 and compound 4 were subjected to conditions described above for compound 75 to obtain 113 as a solid. $[\alpha]_D^{25}$: +4.4° C., c, 0.67, CHCl$_3$. $^1$H NMR (CDCl$_3$, 300 MHz): δ 7.8 (s, 1H), 7.61 (d, 1H, J=10 Hz), 7.44 (m, 2H) 7.21 (m, 5H), 4.92 (d, 1H, J=10.8 Hz), 4.81 (m, 1H), 4.71 (s, 2H), 4.38 (m, 1H), 3.6–3.91 (m, 3H), 3.39 (m, 1H), 3.01 (m, 3H), 2.92 (d, 2H, J=10 Hz), 2.5–2.8 (m, 2H), 1.78–2.02 (m, 5H), 1.4–1.65 (m, 2H), 0.91 (ABq, 6H, J=6.3 Hz).

Compound 114: Compound 112 and compound 15 were subjected to conditions as described above for compound 75 to obtain 114 as a solid. $^1$H NMR (CDCl$_3$, 400 MHz): δ 7.15–7.65 (m, 9H), 5.6 (d, 1H, J=5.1 Hz), 5.54 (d, 1H, J=9.2 Hz), 4.96 (m, 1H), 4.69 (s, 2H), 3.57–3.83 (m, 6H), 2.72–3.2 (m, 7H), 1.9, 1.32 and 1.26 (three m, 3H), 0.88 (ABq, 6H, J=6.4 Hz).

Bis-THF as p2 Ligand in Hydroxyethylsulfonamide Isostere with Variation at p1$^1$ Region

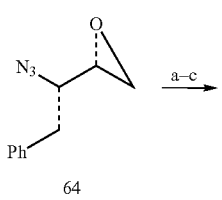

64

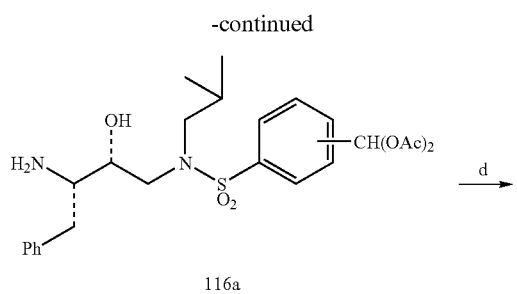

116a

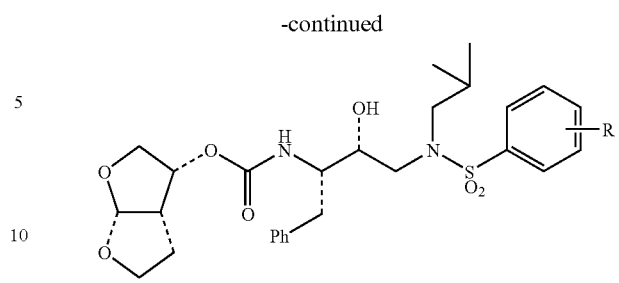

↓ e, f, g

116b

Key: a) iBuNH$_2$, iPrOH, reflux, 6 hours; b) sulfonyl chloride 35 or 36, aq. NaHCO$_3$, CH$_2$Cl$_2$, 12 hours; c) Pd—C (10%), MeOH, 6–8 hours; d) K$_2$CO$_3$, MeOH, 30 min; c) H$_2$, Pd—C (10%), mixed carbonate 15; Et$_3$N, THF, 12 hours; d) (i) NaBH$_4$, EtOH, (ii) TsCl, Et$_3$N, DMAP for compound 117; e) reductive amination (NaCNBH$_4$, AcOH, MeOH); with NH$_4$OAc for compound 118, with MeNH$_2$ for compound 119; f) NH$_2$OH; HCl, Et$_3$N, MeOH, for compound 120; g) (i) triphenylphosphono-acetate, NaH, THF, 0° C., 30 min (ii) DIBAL-H, CH$_2$Cl$_2$, −78° C., 1 h for compound 121.

| | | Activity | |
|---|---|---|---|
| No. | Compound | IC$_{50}$ (nM) | Ki (nM) |
| 117 | | 2.4 | 0.74 |
| 118 | | 2.7 | 0.9 |
| 119 | | 3.5 | 1.1 |

-continued

| No. | Compound | Activity | |
|---|---|---|---|
| | | IC$_{50}$ (nM) | Ki (nM) |
| 120 | [structure] | 2.4 | 0.74 |
| 121 | [structure] | 3.0 | |

Compound 117: Compound 116 was subjected to NaBH$_4$ reduction and the resulting alcohol was treated with pTsCl in pyridine to obtain compound 117 as an oil. $^1$H NMR (CDCl$_3$, 400 MHz): δ 7.79 (d, 2H, J=8 Hz), 7.74 (d, 2H, J=8.4 Hz), 7.43 (d, 2H, J=8 Hz), 7.36 (d, 2H, J=8.4 Hz), 7.23 (m, 5H), 5.64 (d, 1H, J=5.2 Hz), 5.1 (s, 2H), 5.02 (m, 2H), 3.8–4 (m, 3H), 3.7 (m, 2H), 3.61 (m, 1H), 2.75–3.2 (m, 7H), 2.45 (s, 3H), 1.45, 1.6, and 1.83 (three m, 3H), 0.89 (ABq, 6H, J=6.4 Hz).

Compound 118: Compound 117 (26 mg, 0.036 mmol) and NaN$_3$ (5 mg, 0.073 mmol) in DMF (2 mL) were stirred for 30 min at 65–70° C. Then the reaction mixture was diluted with EtOAc (20 mL) and the organic layer washed with brine (2×20 mL). The combined organic layer was dried over anhydrous Na$_2$SO$_4$ and concentrated. Purification of the resulting crude product by flash silica gel chromatography provided an azido intermediate.

The azido intermediate (21 mg, 0.036 mmol) and triphenylphospine (Ph$_3$P) (14 mg, 0.054 mmol) in THF.H$_2$O (9:1, 2 mL) were stirred for 12 hours at room temperature. Then the reaction mixture was diluted with EtOAc (20 mL) and the organic layer washed with brine (2×20 mL). The combined organic layer was dried over anhydrous Na$_2$SO$_4$ and concentrated. Purification of the resulting crude product by flash silica gel chromatography provided compound 118 as a solid. $^1$H NMR (CDCl$_3$, 200 MHz): δ 7.75 (d, 2H, J=8.2 Hz), 7.51 (d, 2H, J=8 Hz), 7.23 (m, 5H), 5.65 (d, 1H, J=5.2 Hz), 4.99 (m, 2H), 3.62–4.1 (m, 6H), 2.73–3.2 (m, 7H), 1.85 (m, 1H), 1.6 (m, 2H), 0.91 (ABq, 6H, J=6.4 Hz).

Compound 119: To compound 116 (75 mg, 0.133 mmol), methylamine (MeNH$_2$) (8.3 mg, 0.026 mmol), and acetic acid (ACOH) (9.5 mg, 0.015 mmol) in MeOH (5 mL) was added sodium cyanoborohydride (NaCNBH$_4$) (10 mg, 0.159 mmol) at room temperature. The resulting reaction mixture was stirred for 12 hours at room temperature. Then the reaction mixture was diluted with EtOAc (20 mL) and NaHCO$_3$ solution (5 mL). The organic layer washed with brine. (2×20 mL). The combined organic layer was dried over anhydrous Na$_2$SO$_4$ and concentrated. Purification of the resulting crude product by flash silica gel chromatography provided compound 119 as a solid. M.P.: 57–62° C. $^1$H NMR (CDCl$_3$, 400 MHz): δ 7.75 (d, 2H, J=7.6 Hz), 7.75 (d, 2H, J=8 Hz), 5.64 (d, 1H, J=5.2 Hz), 5.03 (m, 2H), 3.8–4 (m, 5H), 3.88 (s, 2H), 3.67 (m, 1H), 2.75–3.2 (m, 7H), 1.44, 1.63, and 1.93 (three m, 3H), 0.89 (ABq, 6H, J=6.4 Hz).

Compound 120: The above azido epoxide was converted into the corresponding aldehyde using the following sequence: i) terminal epoxide opening with isobutylamine in isopropyl alcohol for 3 hours; ii) treatment of resulting amine with compound 37 in NaHCO$_3$/H$_2$O; and iii) hydrolysis of the resulting bis-acetoxy compound using K$_2$CO$_3$ in MeOH to obtain the aldehyde. The resulting aldehyde (35 mg, 0.062 mmol), hydroxylamine hydrochloride (NH$_2$OH.HCl) (86 mg, 0.12 mmol), and Et$_3$N (2 eq) in MeOH (5 mL) were stirred for 24 hours at room temperature. Then the reaction mixture was diluted with EtOAc (20 mL) and the organic layer washed with brine (2×20 mL). The combined organic layer was dried over anhydrous Na$_2$SO$_4$ and concentrated. Purification of the resulting crude product by flash silica gel chromatography provided the azido oxime as an oil.

The azido function of the oxime was hydrogenated over Pd/C (10%) in MeOH for 6 hours, and the resulting amine was treated with compound 15 (1 eq.) and Et₃N (2 eq.) in CH₂Cl₂ for 3 hours to obtain compound 120 as a solid. ¹H NMR (CDCl₃, 400 MHz): δ 8.15 and 8.05 (two s, 2H), 7.77 (d, 1H, J=7.6 Hz), 7.72 (d, 1H, J=7.6 Hz), 7.54 (dd, 1H, J=7.6 Hz, 8.0 Hz), 5.67 (d, 1H, J=5.2 Hz), 5.05 (m, 2H), 3.7–4 (m, 6H), 3.19 (m, 1H), 3.1 (m, 2H), 2.95 (d, 2H, J=7.6 Hz), 2.8 (dd, 1H, J=7.6 Hz, 12.4 Hz), 1.6, 1.7, and 1.85 (three m, 3H), 0.89 (d, 6H, J=6.4 Hz).

Compound 121: To (EtO)₂P(O)CH₂CO₂Et (1.1 equiv.) in THF was added NaH (37 mg, 0.93 mmol), followed by stirring for 10 hours at room temperature. Then aldehyde 116 (222 mg, 0.54 mmol) in THF (2 mL) was added and stirring was continued for 10 minutes at room temperature. The reaction mixture was diluted with EtOAc (20 mL) and the organic layer washed with brine (2×20 mL). The combined organic layer was dried over anhydrous Na₂SO₄ and concentrated. Purification of the resulting crude product by flash silica gel chromatography provided an ester. To the ester (50 g, 0.1 mmol) in CH₂Cl₂ (5 mL) was added DIBAL-H (diisobutylaluminum hydride) (1M, 0.5 mL) at −78° C. After 30 min, the reaction mixture was warmed to room temperature, then treated with MeOH (1 mL) to destroy excess DIBAL-H. Cold dil. hydrochloric acid (HCl) (10%, 15 mL) was added cautiously and the resulting mixture was stirred until a clear organic layer was obtained which was extracted with EtOAc (2×10 mL). The organic layer washed with brine (2×20 mL). The combined organic layer was dried over anhydrous Na₂SO₄ and concentrated to obtain a crude product amino allylic alcohol.

The amino alcohol (1 equiv.), compound 15 (1 equiv.), and Et₃N (2 equiv.) in CH₂Cl₂ were stirred for 3 hours at room temperature. Then the reaction mixture was diluted with EtOAc and the organic layer washed with brine. The combined organic layer was dried over anhydrous Na₂SO₄ and concentrated. Purification of the resulting crude product by flash silica gel chromatography provided compound 121 as a solid. ¹H NMR (CDCl₃, 400 MHz): δ 7.72 (d, 2H, J=8 Hz), 7.5 (d, 2H, J=8 Hz), 7.29 (m, 5H), 6.69 (d, 1H, J=16 Hz), 6.51 (m, 1H), 5.6 (d, 1H, J=5.2 Hz), 5 (m, 1H), 4.95 (d, 1H, J=8.4 Hz), 4.37 (d, 2H, J=4.4 Hz), 3.86 (m, 4H), 3.65 (m, 2H), 3.15 (m, 1H), 3.1 (dd, 1H, J=4 Hz, 14.4 Hz), 3 (m, 2H), 2.81 (m, 2H), 1.45, 1.61, and 1.8 (three m, 3H), 0.91 (ABq, 6H, J=6.4 Hz).

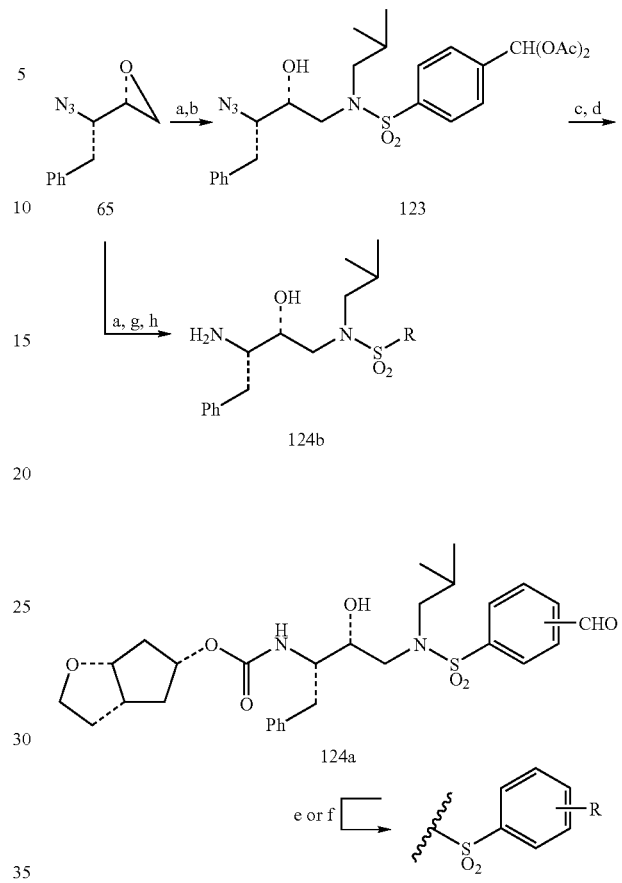

Key: a) iBuNH₂, iPrOH, reflux, 6 hours; b) sulfonyl chloride 35, aq. NaHCO₃, CH₂Cl₂, 12 hours; c) H₂, Pd—C (10%), mixed carbonate 4, Et₃N, THF, 12 hours; d) K₂CO₃, MeOH, 30 min; e) reductive amination (NaCNBH₄, AcOH, MeOH); with NH₄OAc for compound 125, with MeNH₂ for compound 126, with dimethylamine (Me₂NH) for compound 127; f) NH₂OH.HCl, Et₃N, MeOH, for compound 128; g) RSO₂Cl, where R is 4-hydroxymethylsulfonyl chloride, or TsCl, or 8-quinoline sulfonyl chloride, or benzylsulfonyl chloride, aq. NaHCO₃, CH₂Cl₂, 12 hours; h) Ph₃P, THF water, 12 hours.

| No. | Compound | IC₅₀ (nM) | Ki (nM) |
|---|---|---|---|
| 125 | | 3.5 | 1.1 |

| No. | Compound | IC$_{50}$ (nM) | Ki (nM) |
|---|---|---|---|
| 126 | | 15 | |
| 127 | | 50 | |
| 128 | | 1.7 | 0.53 |
| 129 | | 2.9 | 0.9 |
| 130 | | 0.8 | |
| 131 | | 1.4 | |

-continued

| No. | Compound | IC$_{50}$ (nM) | Ki (nM) |
|---|---|---|---|
| 132 | (structure) | 12 | 3.7 |
| 133 | (structure) | 48 | 15 |
| 134 | (structure) | 3000 | 931 |

Compound 125: Compound 124 was converted into compound 125 using the following reaction sequence: i) NaBH$_4$ reduction of aldehyde 124 to primary alcohol; ii) tosylation of primary alcohol; iii) nucleophilic displacement of sulfonate ester with NaN$_3$/DMF/heat (65° C.); iv) conversion of the azido function to amine using Ph$_3$P/THF.H$_2$O (9:1)/12 hours, to obtain compound 125. $^1$H NMR (CDCl$_3$, 400 MHz): δ 7.74 (d, 2H, J=8.4 Hz), 7.48 (d, 2H, J=8.4 Hz), 7.3 (m, 5H), 4.9 (m, 2H), 4.41 (m, 1H), 4 (s, 2H), 3.78 (m, 3H), 3.68 (m, 1H), 2.72–3.2 (m, 6H), 2.65 (m, 1H), 2.46 (br s, 2H), 1.8–2.1 (m, 5H), 1.4 (m, 2H), 0.88 (ABq, 6H, J=6.4 Hz).

Compound 126: Aldehyde 124 (50 mg, 0.89 mmol) and MeNH$_2$ (120 mg, 40% in water) in MeOH (5 mL) were stirred in presence of hydrogen for 12 hours at room temperature. Then the reaction mixture was filtered and concentrated. Purification of the resulting crude product by flash silica gel chromatography provided compound 126 (39 mg) as a solid. $^1$H NMR (CDCl$_3$, 400 MHz): δ 7.73 (d, 2H, J=6.8 Hz), 7.47 (d, 2H, J=7.6 Hz), 7.25 (m, 5H), 4.86 (m, 1H), 4.79 (d, 1H, J=7.6 Hz), 4.39 (t, 1H, J=6.4 Hz), 3.82 (s, 2H), 3.82 (m, 3H), 3.7 (m, 1H), 3 (m, 4H), 2.8 (m, 2H), 2.62 (m, 1H), 2.5 (s, 3H), 2 (m, 4H), 1.85 (m, 2H), 1.4 and 1.6 (two m, 2H), 0.89 (ABq, 6H, J=6.4 Hz).

Compound 127: Aldehyde 124 (32 mg, 0.076 mmol) and HNMe$_2$ (0.09 mL, 0.019 mmol) in MeOH (5 mL) was hydrogenated in presence of Pd—C (10%, 10 mg) for 12 hours. Filtration, followed by concentration, provided a crude product. Purification of the resulting crude product by flash silica gel chromatography provided compound 127 (27 mg) as a solid. [α]$_D^{25}$: +19.29, c 0.57, CHCl$_3$. $^1$H NMR (CDCl$_3$, 200 MHz): δ 7.78 (d, 2H, J=8.2 Hz), 7.58 (d, 2H, J=8.2 Hz), 7.25 (m, 5H), 4.84 (m, 2H), 4.39 (dt, 1H, J=6.4 Hz, 4.4 Hz), 3.6–3.85 (m, 6H), 2.75–3.2 (m, 6H), 2.6 (m, 1H), 2.38 (s, 6H), 2 (m, 3H), 1.9 and 1.5 (two m, 4H), 0.88 (ABq, 6H, J=6.4 Hz).

Compound 128: Aldehyde 124 (137 mg, 0.339 mmol), NH$_2$OH.HCl (46 mg, 0.67 mmol), and Et$_3$N (68 mg, 0.67 mmol) in MeOH (5 mL) were stirred for 12 hours at room temperature. Then the reaction mixture was diluted with EtOAc (30 mL) and the organic layer washed with brine (2×20 mL). The combined organic layer was dried over anhydrous Na$_2$SO$_4$ and concentrated. Purification of the resulting crude product by flash silica gel chromatography provided compound 128 (84 mg) as a solid. $^1$H NMR (CDCl$_3$, 300 MHz): δ 8.53 and 8.1 (two s, 2H), 7.73 (d, 2H, J=8.4 Hz), 7.65 (d, 2H, J=8.7 Hz), 7.2 (m, 5H), 4.83 (m, 1H), 4.79 (d, 1H, J=8.7 Hz), 4.35 (m, 1H), 3.78 (m, 3H), 3.61 (m, 1H), 2.75–3.12 (m, 6H), 2.6 (m, 1H), 1.4, 1.8, and 2 (three m, total 7H), 0.83 (ABq, 6H, J=6.4 Hz).

Compound 129: Compound 37 was used in place of compound 35 in the reaction sequence as described for compound 124 to obtain corresponding meta-substituted aldehyde in quantitative yield. The aldehyde was subjected to similar conditions as described for compound 128 to obtain compound 129 as a solid in quantitative yield. $^1$H NMR (CDCl$_3$, 400 MHz): δ 9.5 (s, 1H), 8.1 (s, 2H), 7.77 (d, 1H, J=8 Hz), 7.62 (d, 1H, J=7.6 Hz), 7.55 (t, 1H, J=4 Hz), 7.23 (m, 5H), 5.02 (d, 1H, J=8.8 Hz), 4.94 (m, 1H), 4.44 (m, 1H), 3.6–4 (m, 4H), 3.4, 3, and 2.83 (three m, 6H), 2.65 (m, 1H), 2.05 (m, 4H), 1.5, 1.63, and 1.9 (three m, 3H), 0.89 (ABq, 6H, J=6.4 Hz).

Compound 130: To 4-bromobenzyl alcohol (1 equiv.) in THF was added sodium hydride (NaH) (2 equiv.) at 0° C. To the resulting sodium alkoxide, after 20 min, was added methyl iodide (MeI) (4 equiv.), and the reaction mixture was allowed to stir for 24 hours at room temperature. After workup and purification, n-BuLi (2.1 equiv.) was used to the resulting methyl ether derivative in THF at −78° C., followed by stirring for 1 hour. In another flask, SO$_2$Cl$_2$ (5 equiv.) in THF was charged and cooled to −78° C. To this solution was added to the above solution. After one hour, workup with sat. NH$_4$Cl solution and flash chromatography, was provided p-methoxymethyl benzene sulfonyl chloride in 33% yield. After step (a) in the above scheme, the resulting amine (1 equiv.), the above p-methoxymethyl benzene sulfonyl chloride (1.1 equiv.) and Et$_3$N (2 equiv.) in CH$_2$Cl$_2$ were stirred for 12 hours at room temperature. Washing the reaction mixture with brine and sat. NH$_4$Cl, and purification of crude residue, provided the corresponding sulfonamide. The azido function of the sulfonamide was converted to amine using Ph$_3$P/TH.H$_2$O (9:1)/12 hours. After purification, the resulting amine (1 equiv.), active carbonate 4 (1.1 equiv.), and Et$_3$N (2 equiv.) in CH$_2$Cl$_2$ were stirred for 2 hours at room temperature. Then the reaction mixture was diluted with EtOAc and the organic layer washed with brine. The combined organic layer was dried over anhydrous Na$_2$SO$_4$ and concentrated. Purification of the resulting crude product by flash silica gel chromatography provided compound 130 as liquid. $^1$H NMR (CDCl$_3$, 400 MHz): δ 7.76 (d, 2H, J=8.4 Hz), 7.48 (d, 2H, J=8.4 Hz), 7.27 (m, 5H), 3.8 (m, 3H), 3.63 (m, 1H), 3.43 (s, 3H), 3–3.15 (m, 3H), 2.95 (dd, 1H, J=13.6 Hz, 8.4 Hz), 2.83 (m, 2H), 2.63 (m, 1H), 2.05 (m, 3H), 1.81 (m, 2H), 1.49 and 1.55 (two m, 2H), 0.87 (ABq, 6H, J=6.4 Hz).

Compound 131: After step (a) in above scheme, the resulting amine (1 equiv.) and TsCl (1.1 equiv.), in a mixture of sat. NaHCO$_3$ solution and CH$_2$Cl$_2$, were stirred for 12 hours at room temperature. Then the reaction mixture was extracted with EtOAc and the organic layer washed with brine. The combined organic layer was dried over anhydrous Na$_2$SO$_4$ and concentrated. Purification of the resulting crude product by flash silica gel chromatography provided the p-toluene sulfonamide derivative. The azido function of the above sulfonamide was hydrogenated in presence Pd—C (10%) for 6 hours and the resulting amine (1 equiv.), active carbonate 4 (1.1 equiv.), Et$_3$N (2 equiv.) in CH$_2$Cl$_2$ were stirred for 4 hours at room temperature. Then the reaction mixture was diluted with EtOAc and the organic layer washed with brine. The combined organic layer was dried over anhydrous Na$_2$SO$_4$ and concentrated. Purification of the resulting crude product by flash silica gel chromatography provided compound 131 as solid. $^1$H NMR (CDCl$_3$, 400 MHz): δ 7.6 (d, 2H, J=8.4 Hz), 7.31 (d, 2H, J=8 Hz), 7.25 (m, 5H), 4.87 (m, 1H), 4.75 (m, 1H), 4.4 (m, 1H), 3.8 (m, 3H), 3.7 (m, 1H), 2.7–3.2 (m, 6H), 2.62 (m, 1H), 2.42 (s, 3H), 2.03 (m, 3H), 1.82 (m, 2H), 1.4 and 1.53 (two m, 2H), 0.87 (ABq, 6H, J=6.4 Hz).

Compound 132: After step (a) in the scheme above, the resulting amine (1 equiv.) and commercially available 8-quinoline sulfonyl chloride (1.1 equiv.) in a mixture of sat. NaHCO$_3$ solution and CH$_2$Cl$_2$ were stirred for 12 hours at room temperature. Then the reaction mixture was diluted with EtOAc and the organic layer washed with brine. The combined organic layer was dried over anhydrous Na$_2$SO$_4$ and concentrated. Purification of the resulting crude product by flash silica gel chromatography provided corresponding 8-quinoline sulfoanmide derivative. The azido function of the above quinoline derivative (7 mg, 0.016 mmol) was hydrogenated in presence of Pd—C (10%) in THF for 6 hours, and the resulting amine was treated in situ with active carbonate 4 (4 mg, 0.016 mmol) and Et$_3$N (2 equiv.) in CH$_2$Cl$_2$ (2 mL). The resulting mixture was stirred for 2 hours at room temperature. Then the reaction mixture was diluted with EtOAc and the organic layer washed with brine. The combined organic layer was dried over anhydrous Na2SO$_4$ and concentrated. Purification of the resulting crude product by flash silica gel chromatography provided compound 132 (6.6 mg) as solid. $^1$H NMR (CDCl$_3$, 300 MHz): δ 9.02 (dd, 1H, J=1.8 Hz, 3.9 Hz), 8.51 (dd, 1H, J=0.92 Hz, 7.2 Hz), 8.23 (dd, 1H, J=1.8 Hz, 8.7 Hz), 8.03 (dd, 1H, J=0.9 Hz, 8.1 Hz), 7.6 (dd, 1H, J=7.5 Hz, 7.8 Hz), 7.53 (dd, 1H, J=4.5 Hz, 8.4 Hz), 7.2 (m, 5H), 4.8 (m, 1H), 4.73 (d, 1H, J=7.8 Hz), 4.34 (dd, 1H, J=5.4 Hz, 6.3 Hz), 3.76–3.92 (m, 3H), 3.6 (m, 1H), 3.29 (d, 1H, 14 Hz), 3.02 (m, 3H), 2.91 (m, 2H), 2.62 (m, 1H), 1.97 (m, 3H), 1.7 (m, 2H), 1.52 and 1.4 (two m, 2H), 0.65 (ABq, 6H, J=6.4 Hz).

Compound 133: After reaction step (a), the resulting amine (41 mg, 0.157 mmol), commercially available benzyl sulfonyl chloride (1.1 equiv.), and Et$_3$N (2 equiv.) in CH$_2$Cl$_2$ (3 mL) were stirred for 12 hours at room temperature. Then the reaction mixture was diluted with EtOAc (20 mL) and the organic layer washed with brine (20 mL). The combined organic layer was dried over anhydrous Na$_2$SO$_4$ and concentrated. Purification of the resulting crude product by flash silica gel chromatography provided the corresponding sulfonamide. The above sulfonamide (38 mg, 0.091 mmol) and Ph$_3$P (47 mg, 0.18 mmol) in THF.H$_2$O (9:1) were stirred for 12 hours at room temperature. Then the reaction mixture was diluted with EtOAc (20 mL) and the organic layer washed with brine (20 mL). The combined organic layer was dried over anhydrous Na$_2$SO$_4$ and concentrated. The resulting crude product amine, active carbonate 4 (25 mg, 0.93 mmol), and Et$_3$N (2 equiv.) in CH$_2$Cl$_2$ (5 mL) were stirred for 4 hours at room temperature. Then the reaction mixture was diluted with EtOAc (20 mL) and the organic layer washed with brine (20 mL). The combined organic layer was dried over anhydrous Na$_2$SO$_4$ and concentrated. Purification of the resulting crude product by flash silica gel chromatography provided compound 133 as solid. $^1$H NMR (CDCl$_3$, 400 MHz): δ 7.18–7.36 (m, 10H), 4.9, 4.73, and 4.4 (three m, 3H), 4.27 (s, 2H), 3.72 (m, 4H), 3.05 and 3.16 (two m, 2H), 2.81 (m, 5H), 1.5–2.1 (m, 7H), 0.84 ABq, 6, H, J=6.4 Hz).

Compound 134: After reaction step (a), the resulting amine (1 equiv.), 3,5-dihydroxybenzoic acid (1 equiv.), EDCI (1-(3-dimethylaminopropyl)-3-ethylcarbodiimide hydrochloride) (1.2 equiv.), HOBt (1-hydroxybenzotriazole hydrate) (1.2 equiv.), and Et$_3$N (4 equiv.) in CH$_2$Cl$_2$.DMF (9:1) were stirred for 12 hours at room temperature. Then the reaction mixture was diluted with EtOAc and the organic layer washed with brine. The combined organic layer was dried over anhydrous Na$_2$SO$_4$ and concentrated. Purification of the resulting crude product by flash silica gel chromatography provided corresponding 3,5-dihydroxybenzamide derivative. The above derivative (1 equiv.) and active carbonate 4 (1.1 equiv.) in THF were stirred under hydrogen atmosphere in presence of Pd—C (10%) for 12 hours at room temperature. Then the reaction mixture was filtered and the organic layer washed with brine. The combined organic layer was dried over anhydrous Na$_2$SO$_4$ and concentrated. Purification of the resulting crude product by flash silica gel chromatography provided compound 134 as a solid.

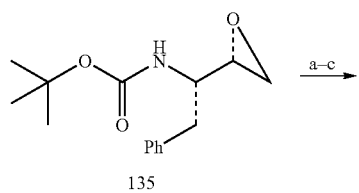

135

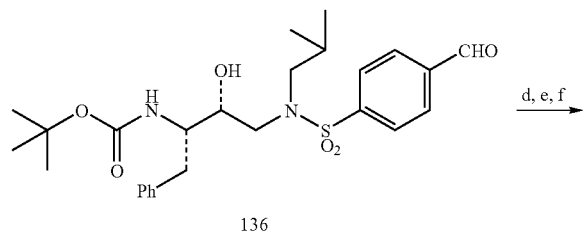

136

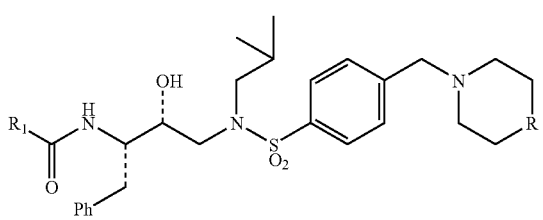

Key: a) Isobutylamine, isopropanol, reflux, 6 hours; b) sulfonyl chloride 35, aq. NaHCO$_3$, CH$_2$Cl$_2$; c) K$_2$CO$_3$, MeOH, 30 min; d) N-methylpyrazine or morpholine, NaCNBH$_4$, AcOH, MeOH, 12 hours; e) TFA, CH$_2$Cl$_2$; f) mixed carbonate 22, Et$_3$N, CH$_2$Cl$_2$.

| No. | R$_1$ | R$_2$ | IC$_{50}$ (nM) |
|---|---|---|---|
| 137 | 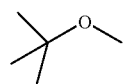 | NMe | 2100 |
| 138 | 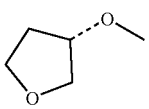 | NMe | 270 |

-continued

| No. | R$_1$ | R$_2$ | IC$_{50}$ (nM) |
|---|---|---|---|
| 139 | (structure) | O | 968 |

Compound 137: $^1$H NMR (CDCl$_3$, 400 MHz): δ 7.71 (d, 2H, J=8 Hz), 7.47 (d, 2H, 8.4 Hz), 7.27 (m, 5H), 4.65 (d, 1H, J=8.4 Hz), 3.79 (m, 2H), 3.55 (s, 2H), 2.8–3.12 (m, 6H), 2.5 (br m, 8H), 2.31 (s, 3H), 1.84 (m, 1H), 1.33 (s, 9H), 0.9 (ABq, 6H, J=6.4 Hz).

Compound 138: Compound 125 was subjected to TFA.CH$_2$Cl$_2$ (20%) for 20 min at room temperature that provided a crude amine salt after concentration. The amine salt (8.7 mg), active carbonate 22 (5 mg), and Et$_3$N (2 equiv.) in CH$_2$Cl$_2$ (2 mL) were stirred for 4 hours at room temperature. Then the reaction mixture was diluted with EtOAc (20 mL) and the organic layer washed with brine (20 mL). The combined organic layer was dried over anhydrous Na$_2$SO$_4$ and concentrated. Purification of the resulting crude product by flash silica gel chromatography provided compound 138. $^1$H NMR (CDCl$_3$, 400 MHz): δ 7.74 (d, 2H, J=8 Hz), 7.51 (d, 2H, J=8.4 Hz), 7.29 (m, 5H), 5.11 (m, 1H), 4.88 (d, 1H, J=8.4 Hz), 3.79 (m, 5H), 3.61 (m, 1H), 3.56 (s, 2H), 3.12 (m, 1H), 2.95 (d, 2H, J=13.6), 2.92 and 2.87 (two m, 2H), 2.82 (dd, 1H, J=6.8 Hz, 13.6 Hz), 2.5 (m, 8H), 2.37 (s, 3H), 2.1, 1.92, and 1.81 (three m, 3H), 0.88 (ABq, 6H, J=6.4 Hz).

Compound 139: To compound 135 (17 mg), AcOH (3 mg), and morpholine (9 mg) in MeOH was added NaCNBH$_4$ (4 mg). The resulting reaction mixture was stirred for 12 hours at room temperature. Then the reaction mixture was diluted with EtOAc (20 mL) and the organic layer washed with brine (2×20 mL). The combined organic layer was dried over anhydrous Na$_2$SO$_4$ and concentrated. Purification of the resulting crude product by flash silica gel chromatography provided morpholine derivative.

The morpholine derivative (10 mg) was treated with 20% TFA (trifluoroacetic acid).CH$_2$Cl$_2$ (3 mL) for 30 min. After evaporation of solvent and drying the resulting amine salt, active carbonate 22 (6 mg) and Et$_3$N (2 equiv.) in CH$_2$Cl$_2$ (3 mL) were stirred for 3 hours at room temperature. Then the reaction mixture was diluted with EtOAc (20 mL) and the organic layer washed with brine (20 mL). The combined organic layer was dried over anhydrous Na$_2$SO$_4$ and concentrated. Purification of the resulting crude product by flash silica gel chromatography provided compound 139. $^1$H NMR (CDCl$_3$, 400 MHz): δ 7.75 (d, 2H, J=8 Hz), 7.5 (d, 2H, J=8 Hz), 5.1 (m, 1H), 4.88 (d, 1H, J=8.4 Hz), 3.8 (m, 9H), 3.6 (m, 1H), 3.55 (s, 2H), 3.14 (dd, 1H, J=7.6 Hz, 15.2 Hz), 3.05 (m, 3H), 2.91 (m, 1H), 2.88 (dd, 1H, J=6.4 Hz, 13.2 Hz), 2.5 (s, 4H), 2.1, 1.9, and 1.87 (three m, 3H), 0.89 (ABq, 6H, J=6.4 Hz).

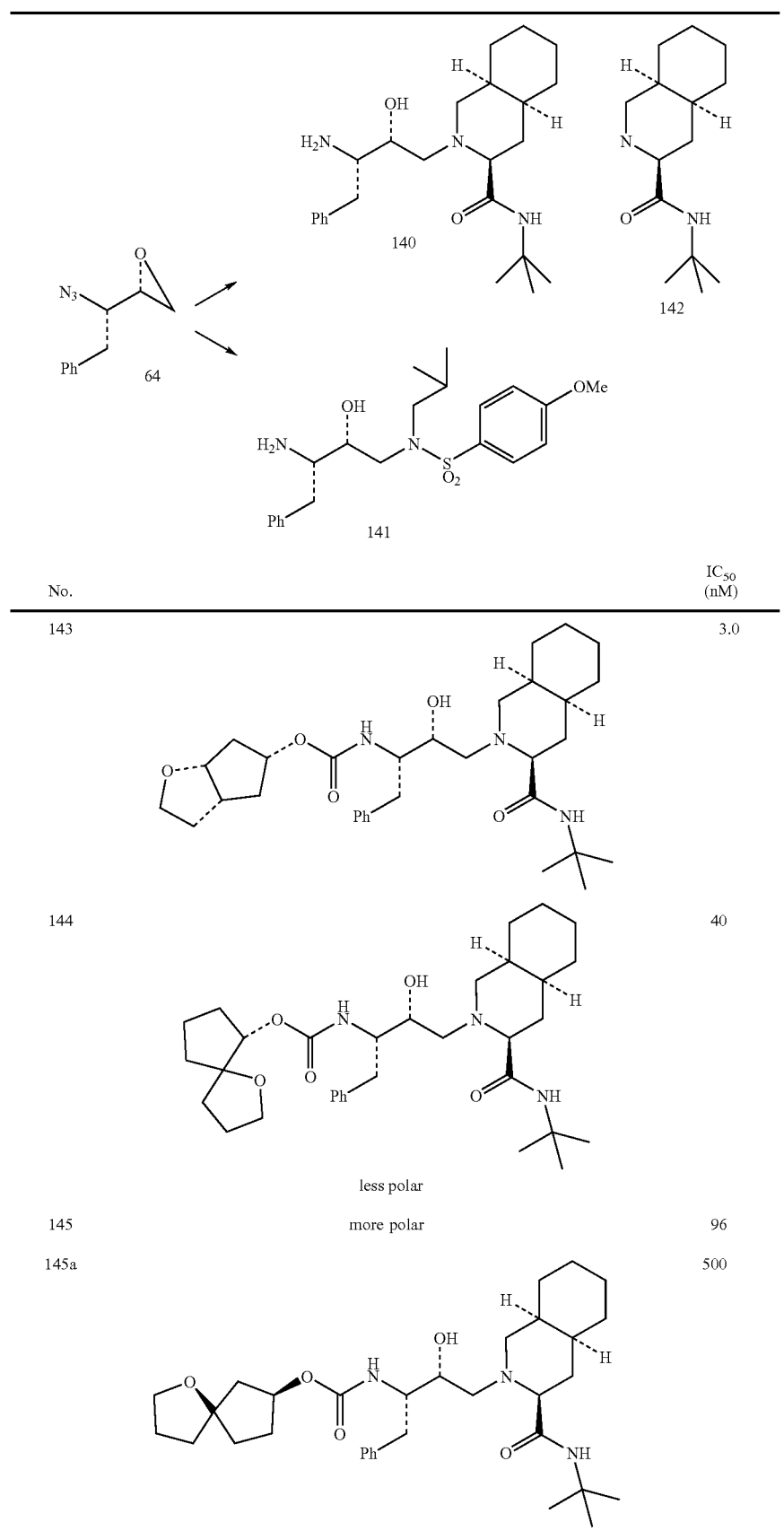

-continued
| | | |
|---|---|---|
| 145b | 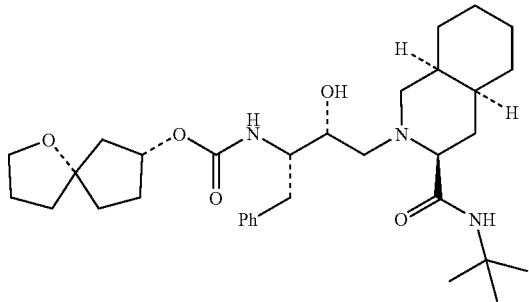 | >2000 |
| 145c | 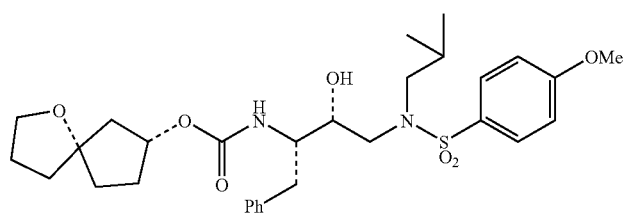 | 15 |
| 145d | 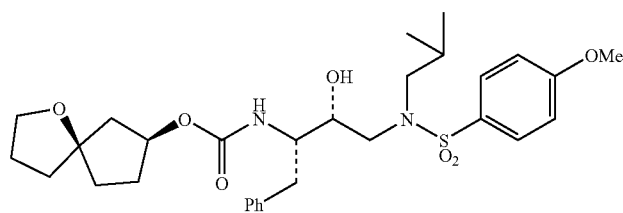 | 4.6 |
| 146 | 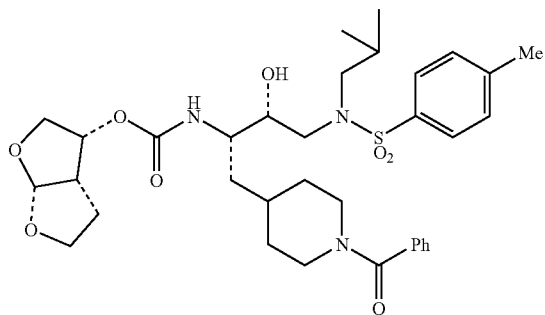 | 1.8 |
| 147 | 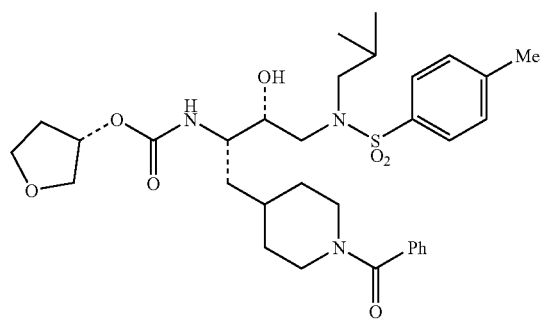 | 60 |

-continued
| No. | | IC$_{50}$ (nM) | Ki (nM) |
|---|---|---|---|
| 148 | 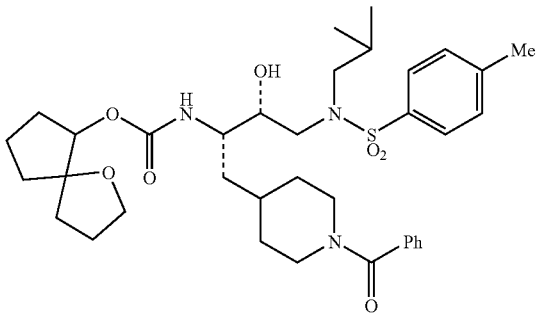 | 185 | |
| 149 | 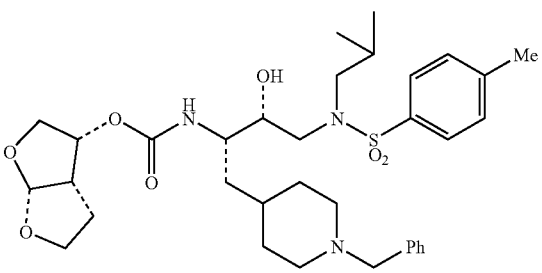 | 20 | |
| 150 | 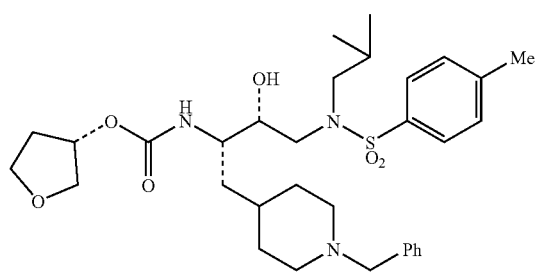 | 540 | |
| 151 | 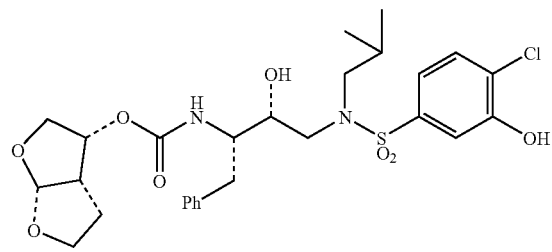 | 3.1 | 1.0 |
| 152 | 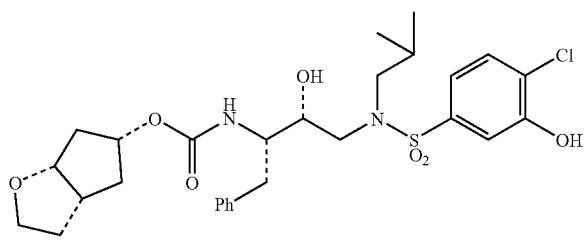 | 5.2 | 1.8 |

-continued
| | | | |
|---|---|---|---|
| 153 | 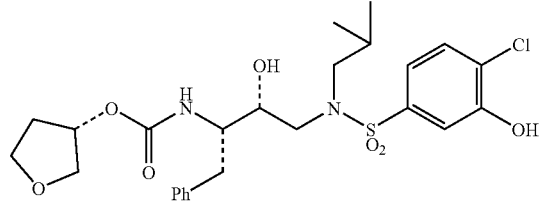 | 3.6 | 1.1 |
| 154 | 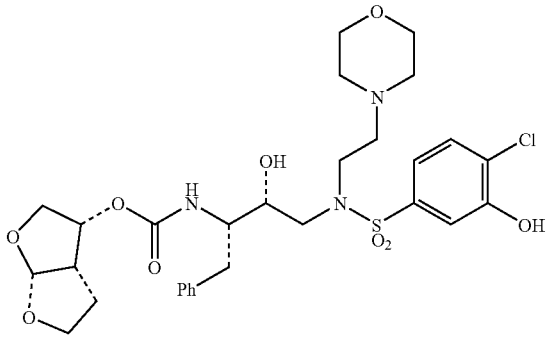 | 25 | 7.8 |
| 155 | 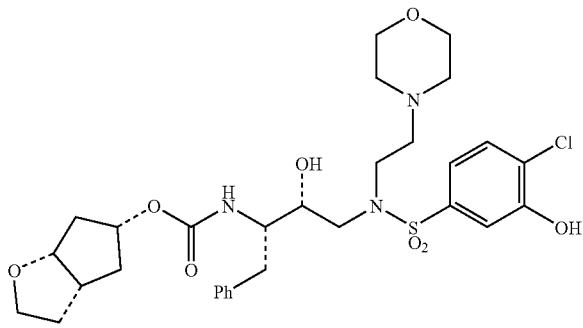 | 16 | 4.9 |
| 156 | 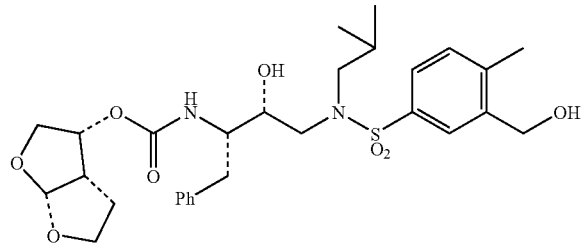 | 3.1 | 0.97 |
| 157 | 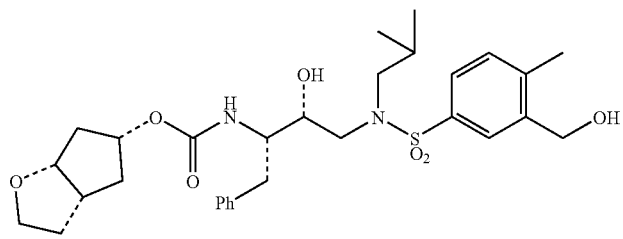 | 2.8 | 0.87 |

-continued

| # | Structure | Col A | Col B |
|---|---|---|---|
| 158 | 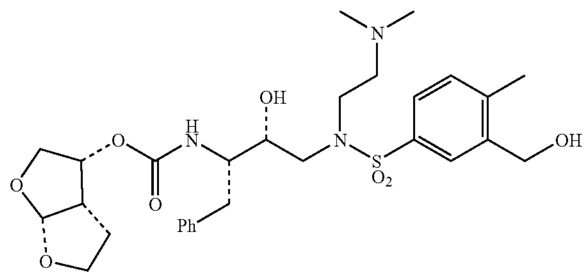 | 105 | 32 |
| 159 | 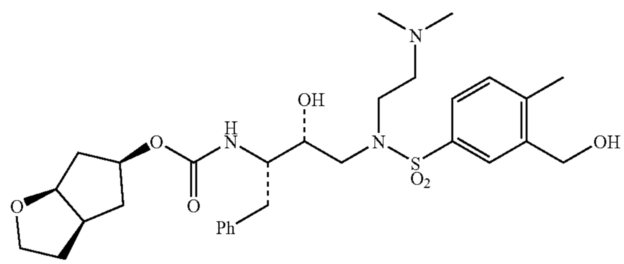 | 204 | 63 |
| 160 | 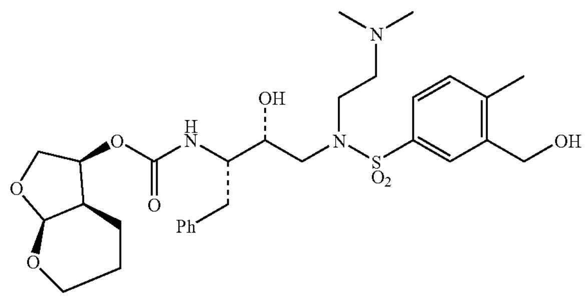 | 231 | 72 |
| 161 | 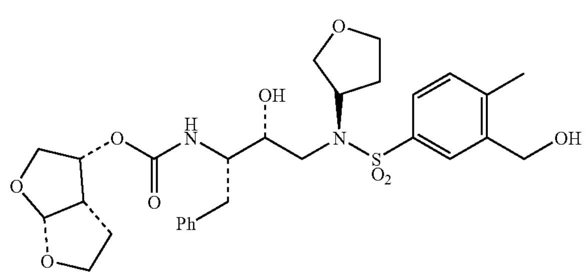 | 2.0 | 1.6 |
| 162 | 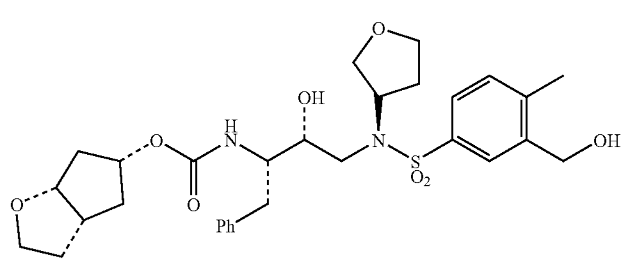 | 4.1 | 1.3 |
| 163 | 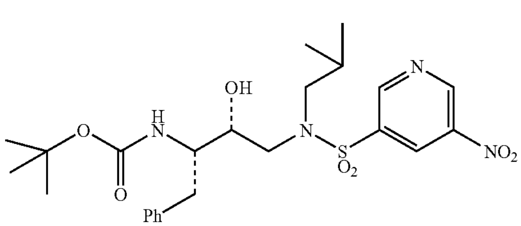 | 115 | 36 |

-continued
| | | | |
|---|---|---|---|
| 164 | 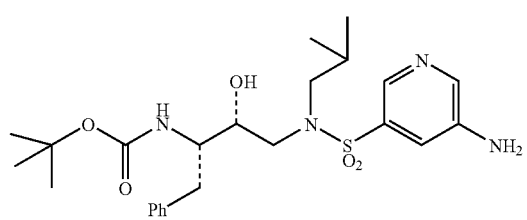 | 33 | 10 |
| 165 | 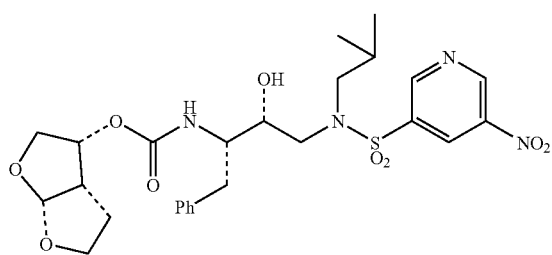 | 3.5 | 1.0 |
| 166 | 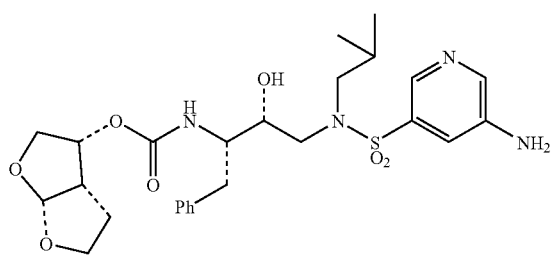 | 0.91 | 0.28 |
| 167 | 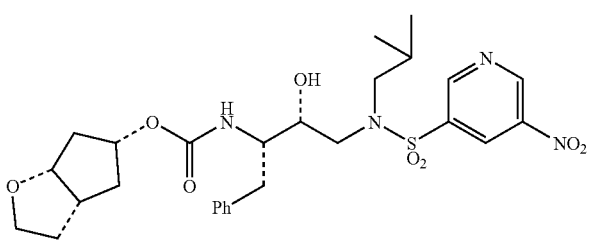 | 4.5 | 1.4 |
| 168 | 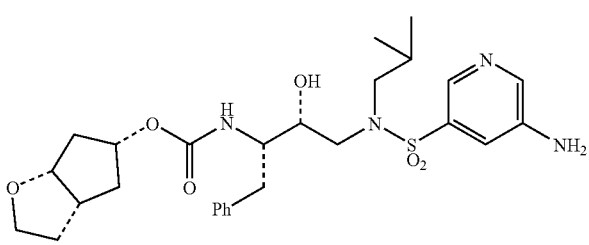 | 2.5 | 0.8 |
| 169 | 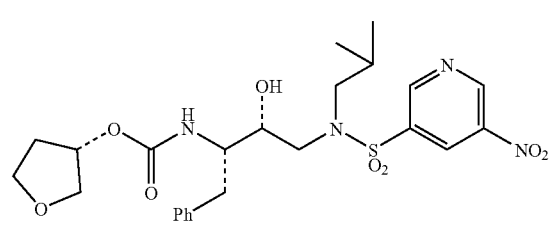 | 7.1 | 22 |

-continued
| | | | |
|---|---|---|---|
| 170 | 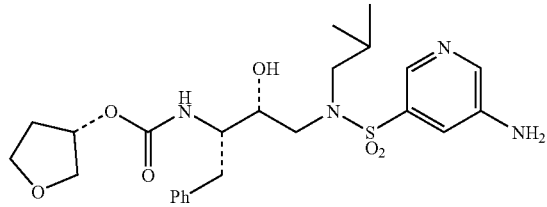 | 2.4 | 0.74 |
| 171 | 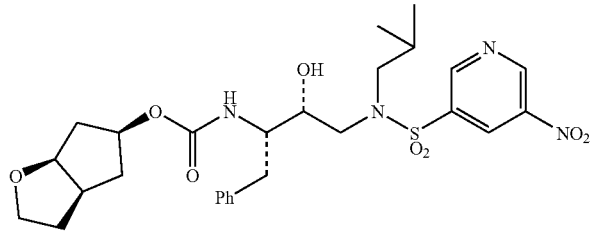 | 14 | 4.3 |
| 172 | 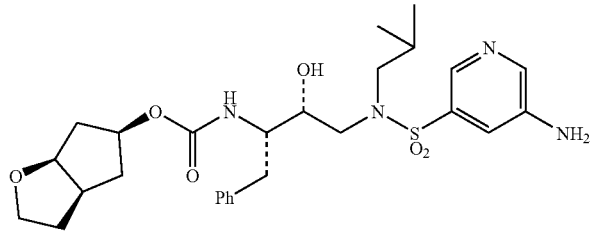 | 5.1 | 1.6 |
| 179 | 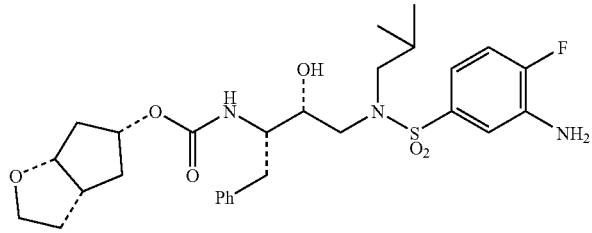 | 6.4 | 2.0 |
| 180 | 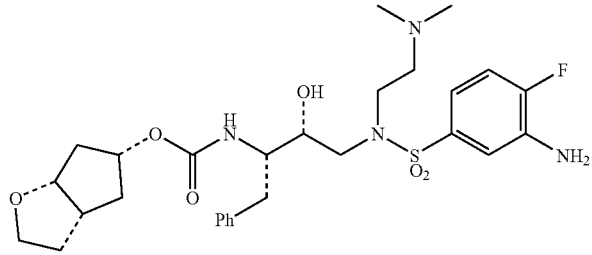 | 1500 | 472 |
| 181 | 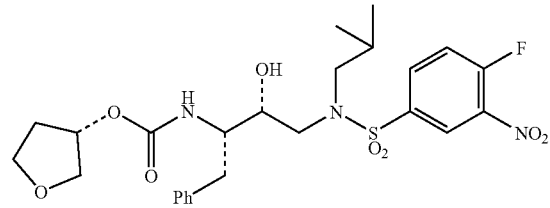 | 145 | 45 |

-continued
| | | | |
|---|---|---|---|
| 182 | 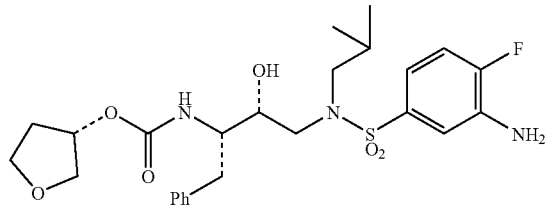 | 4.6 | 1.4 |
| 183 | 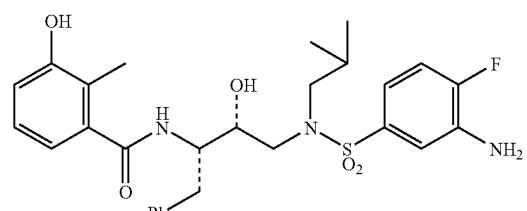 | 179 | 56 |
| 184 | 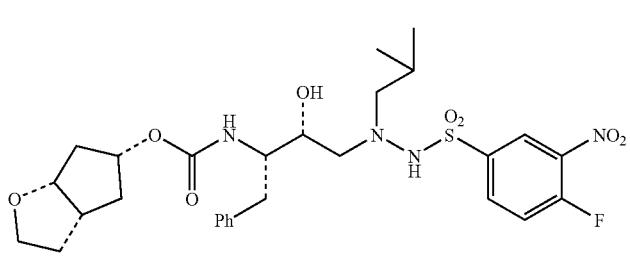 | 1200 | 351 |
| 185 | 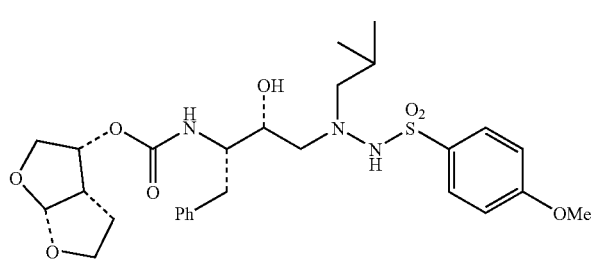 | 312 | 97 |
| 186 | 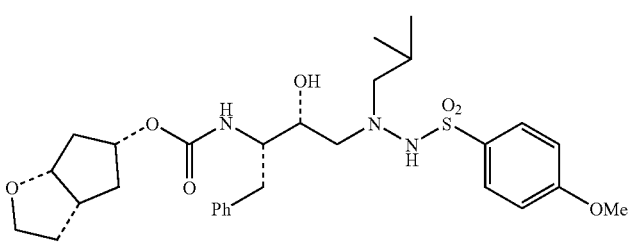 | 10 | 3.2 |
| 187 | 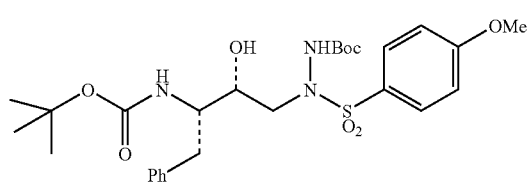 | 534 | 166 |
| 188 | 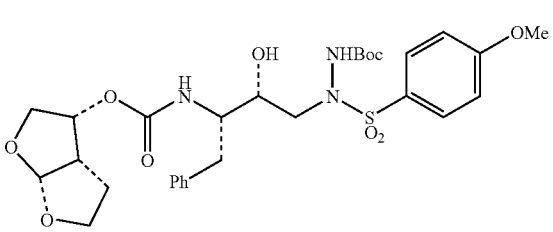 | 3.9 | 1.2 |

| | | | |
|---|---|---|---|
| 189 | 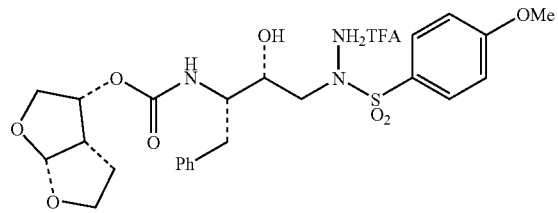 | 55 | 17 |
| 190 | 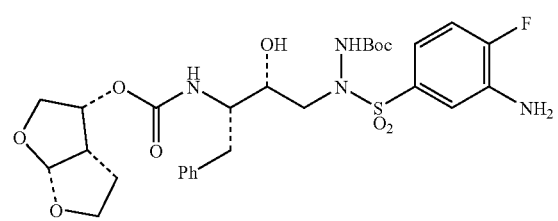 | 3.5 | 1.1 |
| 191 | 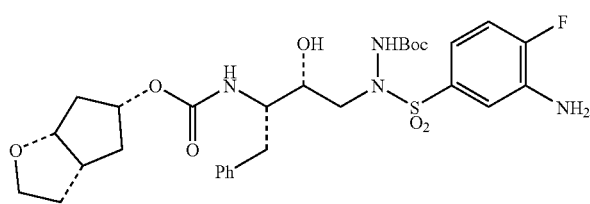 | 9.6 | 3.0 |
| 200 | 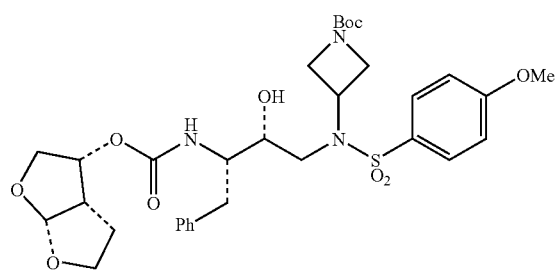 | 7.6 | 2.3 |
| 201 | 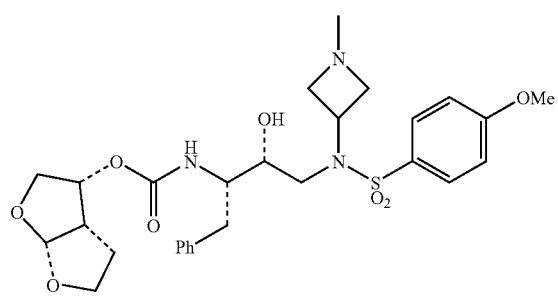 | 5.6 | 1.7 |
| 202 | 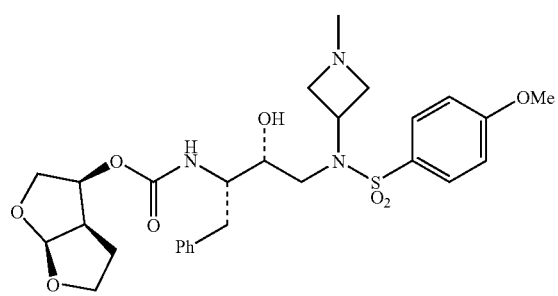 | 31 | 9.7 |

-continued

| | | |
|---|---|---|
| 203 | 15 | 4.7 |
| 204 | 5.6 | 1.7 |
| 205 | 87 | 27 |
| 206 | 109 | 34 |
| 207 | 96 | 30 |
| 208 | >2300 | |

-continued
| | | | |
|---|---|---|---|
| 209 | 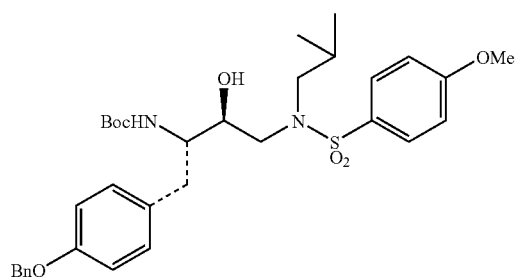 | 30 | 9.3 |
| 210 | 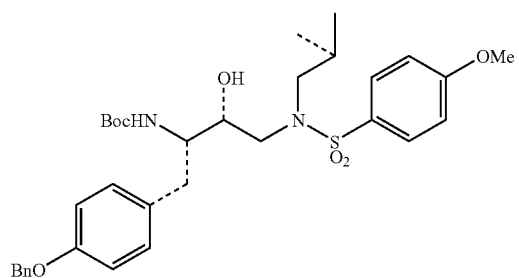 | 13 | 4.1 |
| 211 | 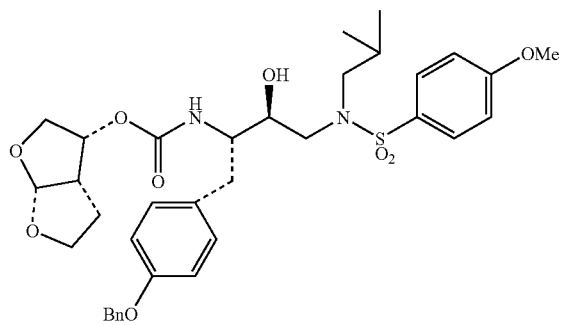 | 90 | 28 |
| 212 | 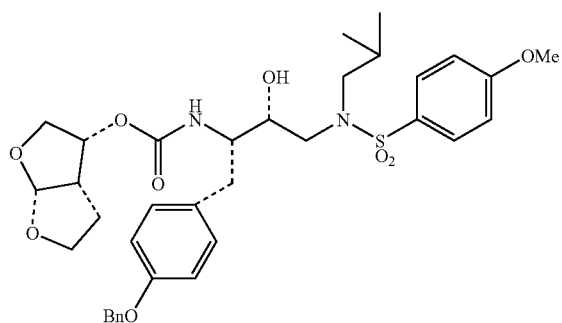 | 30 | 9.3 |
| 213 | 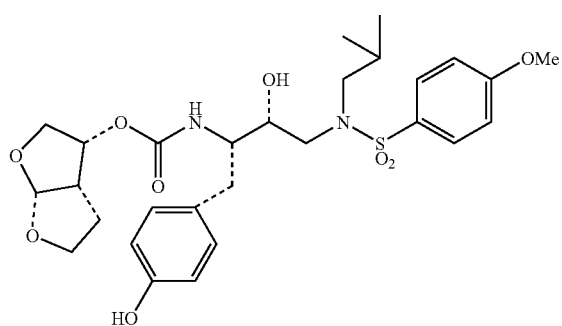 | 4.1 | 1.3 |

-continued
| | | | |
|---|---|---|---|
| 226 | 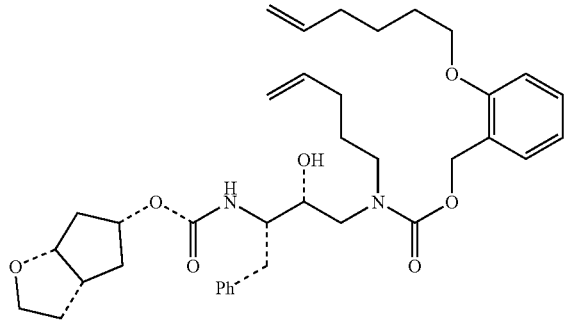 | >2000 | |
| 227 | 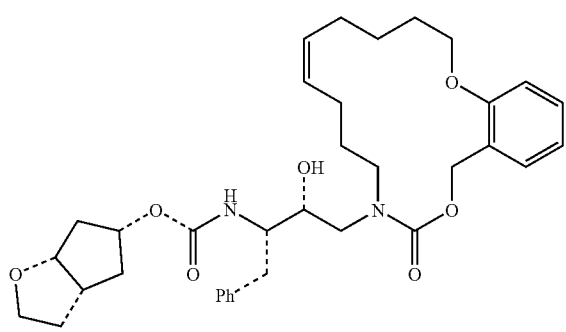 | 495 | 154 |
| 228 | 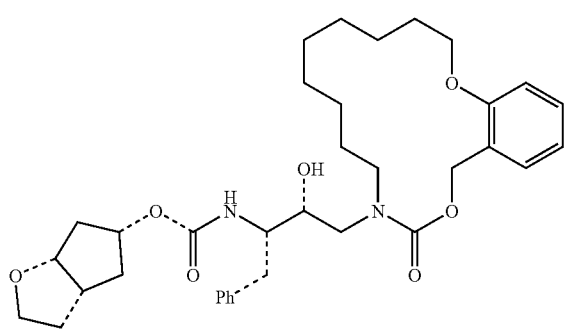 | 2200 | 638 |
| 229 | 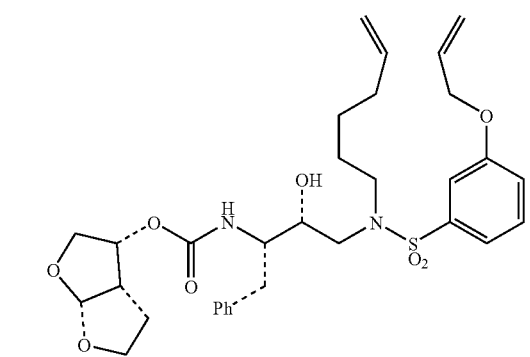 | 9.1 | 2.1 |

-continued
| 230 | 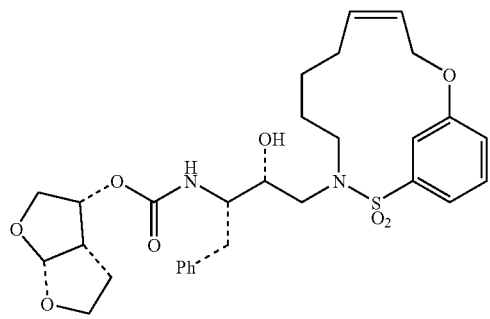 | 5.3 | 1.6 |
| 231 | 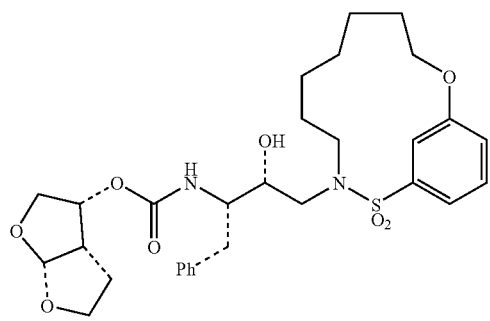 | 8.6 | 2.7 |
| 232 | 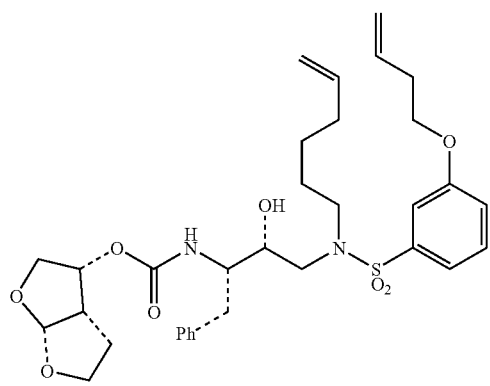 | 5.4 | 1.7 |
| 233 | 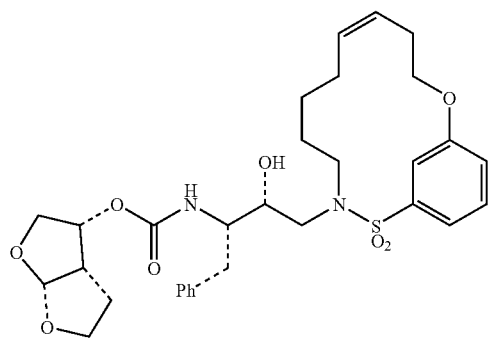 | 8.7 | 2.7 |

| | | | |
|---|---|---|---|
| 234 | 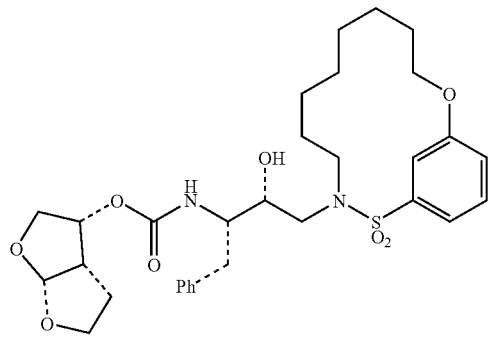 | 7.3 | 2.3 |
| 225 | 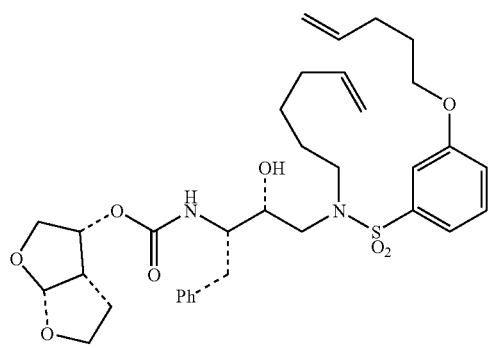 | 8.1 | 2.5 |
| 225a | 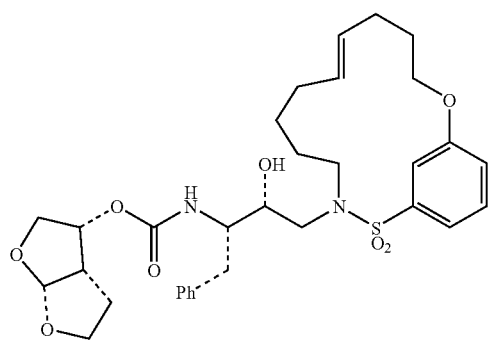 | 7.8 | 2.4 |
| 225b | 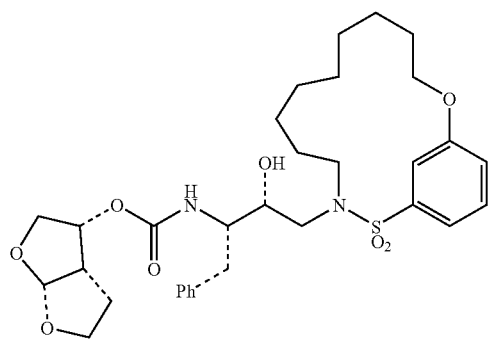 | 7.8 | 2.4 |

-continued
| | | | |
|---|---|---|---|
| 225c | 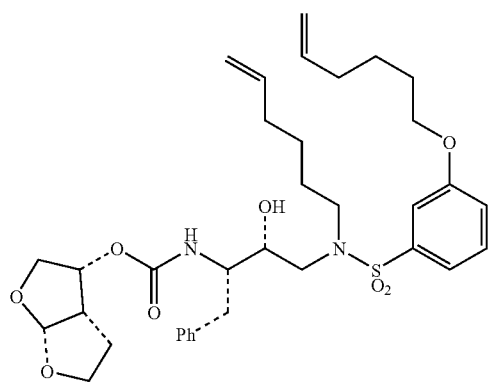 | 8.5 | 2.6 |
| 225d | 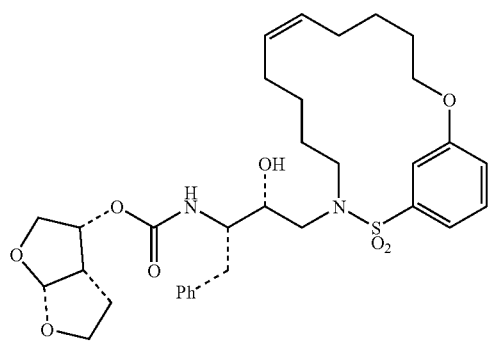 | 5.3 | 1.6 |
| 225e | 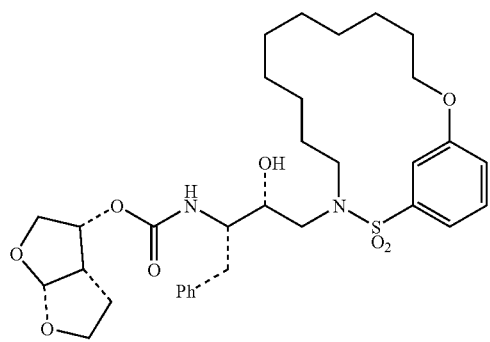 | 5.0 | 1.6 |
| 225f | 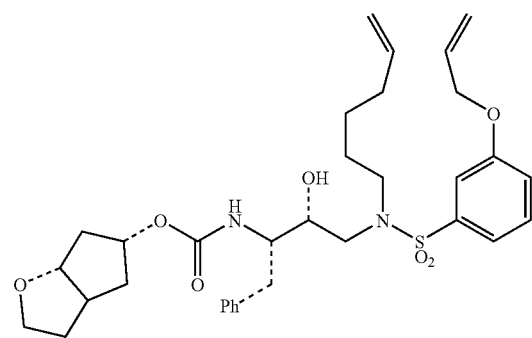 | 11 | 3.4 |

-continued
| | | | |
|---|---|---|---|
| 225g | 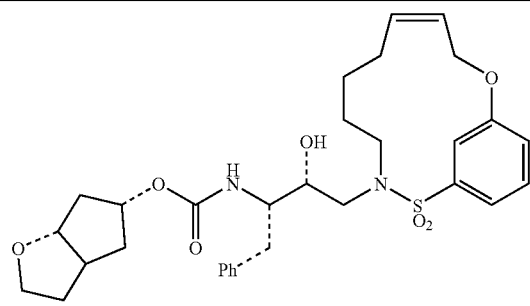 | 10 | 3.1 |
| 225h | 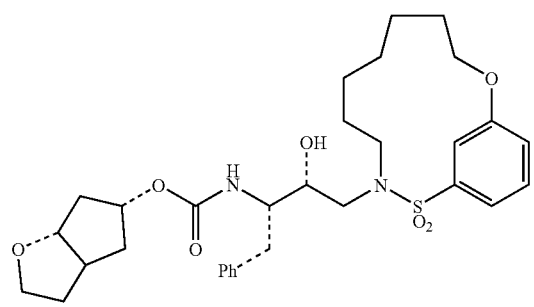 | 6.8 | 2.1 |
| 225i | 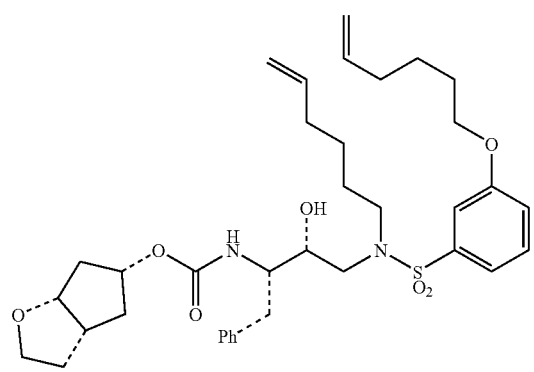 | 17 | 5.3 |
| 235 | 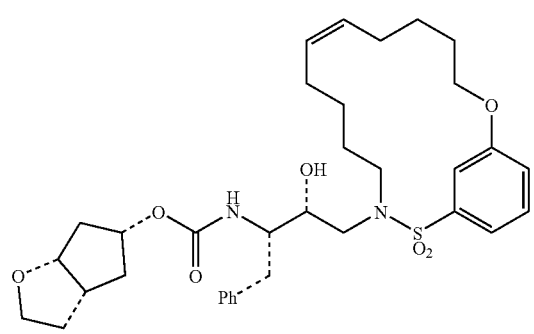 | 9.3 | 2.9 |
| 236 | 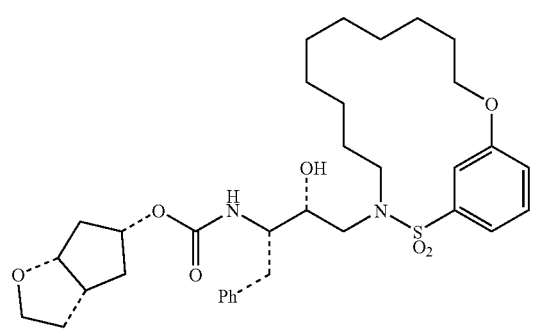 | 11 | 3.4 |

| | | | |
|---|---|---|---|
| 237 | 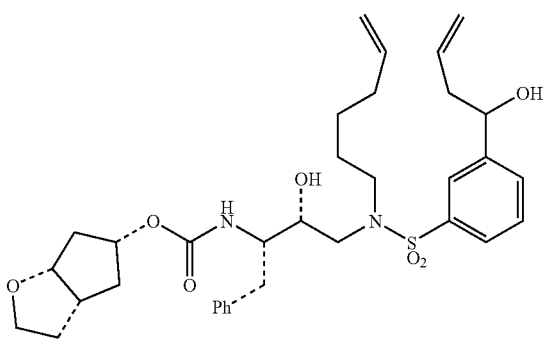 | 10 | 3.1 |
| 238 | 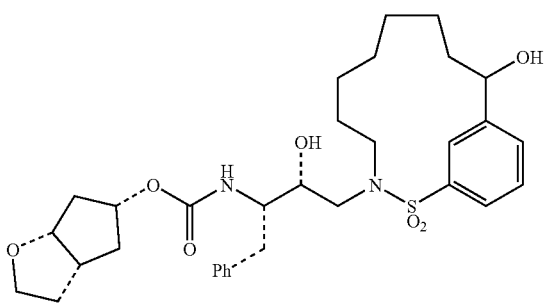 | 4 | 1.2 |
| 239 | 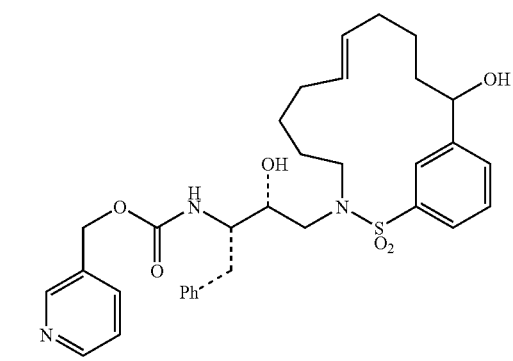 | 34 | 11 |
| 248 | 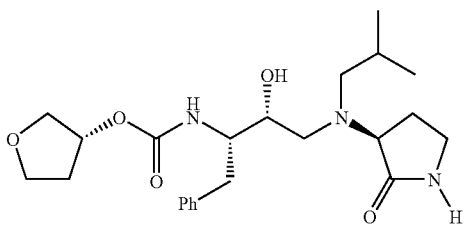 | 730 | |
| 249 | 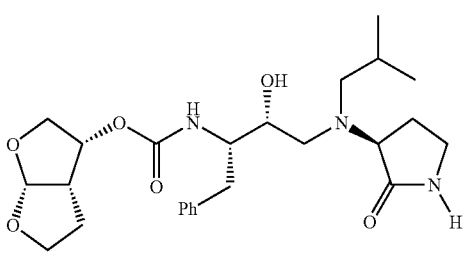 | 37 | |

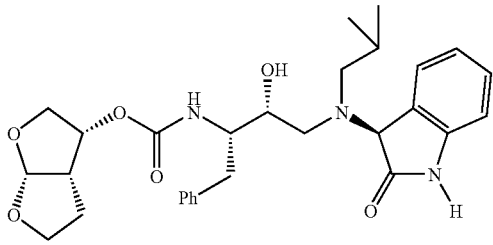

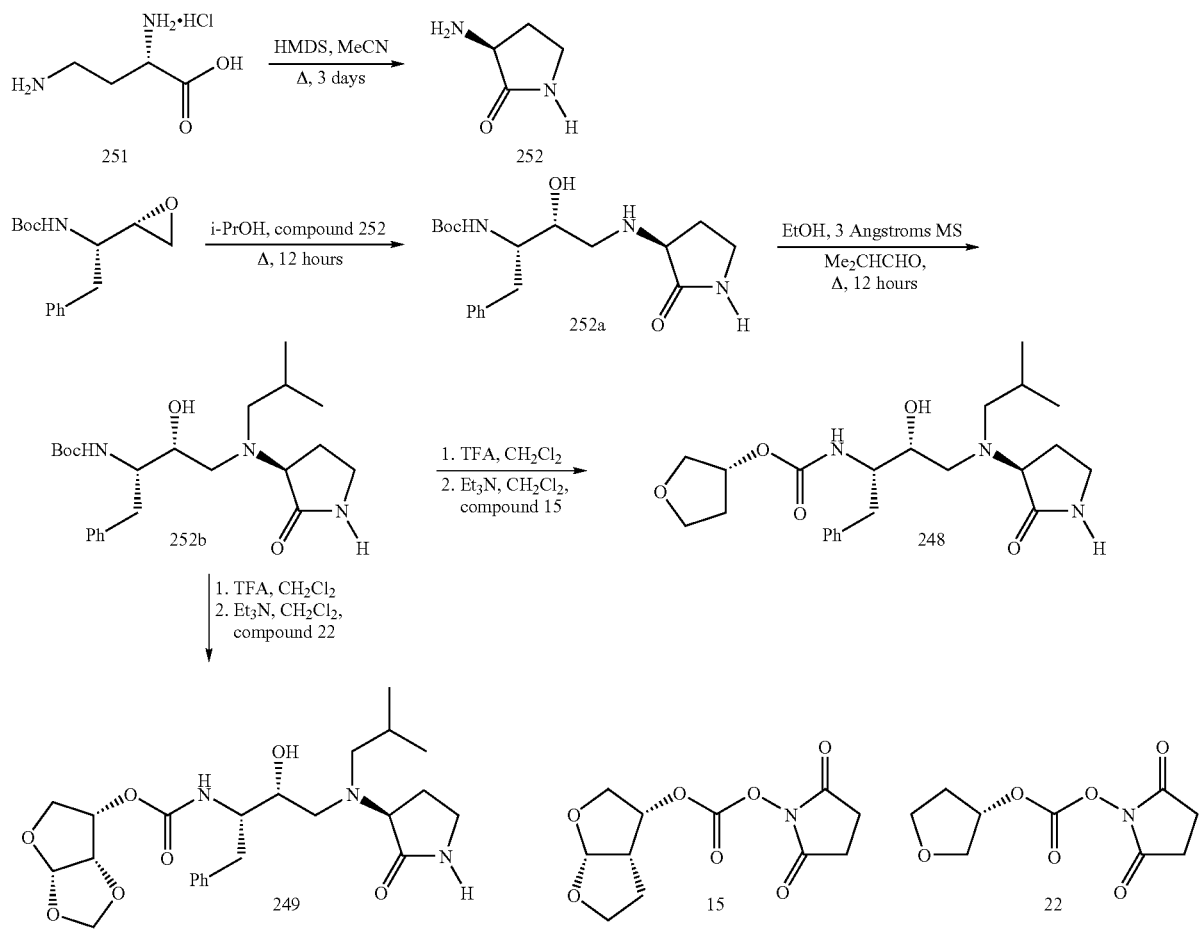

3S-Aminopyrrolidin-2-one (252)

A solution of (S)-4-amino-2-methylbutyric acid hydrochloride (251, 190 mg, 1.23 mmol) in acetonitrile (25 mL) and hexamethyldisilazane (HMDS) (1 mL) was heated under reflux for 72 hours. The solvent was evaporated under vacuum, and the residue was purified by silica gel column chromatography eluting with 15% MeOH in CHCl$_3$, yielding 36 mg of compound 252 (29%) as a colorless solid, R$_f$=0.20.

{1S-Benzyl-2R-hydroxy-3-[(3'S)-oxopyrrolidin-3-ylamino]propyl}carbamic acid tert-butyl ester (252a): A solution of tert-butyl[S-(R*,R*)]-(−)-(1-oxiranyl-2-phenylethyl)carbamate (26 mg, 0.10 mmol), 3S-aminopyrrolidin-2-one (2.52, 20 mg, 0.20 mmol), and isopropylethylamine (70 μL, 0.40 mmol) in isopropanol (3 mL) was heated under reflux for 12 hours. The solvent was evaporated under vacuum, and the residue was purified by silica gel column chromatography eluting with 15% MeOH in chloroform (CHCl$_3$), yielding 10 mg of compound 252a (28%) as a colorless solid, R$_f$=0.25.

{1S-Benzyl-2R-hydroxy-3-[(3'S)-isobutyl(2-oxopyrrolidin-3-yl)amino]propyl}carbamic acid tert-butyl ester (252b): A solution of {1S-benzyl-2R-hydroxy-3-[(3'S)-oxopyrrolidin-3-ylamino]propyl}carbamic acid tert-butyl ester (252a, 5.0 mg, 0.014 mmol), iso-butyraldehyde (0.10 mL, 1.1 mmol), and molecular sieve (3 Å, 100 mg) in EtOH (1 mL) under argon was heated at reflux for 12 hours. The solvent was evaporated under vacuum, and the residue was redissolved in EtOH (1 mL). Glacial acetic acid (0.10 mL) was added, followed by sodium cyanoborohydride (30 mg, 0.048 mmol). After 30 min, saturated aq. NaHCO$_3$ (5 mL) was added, and the mixture was extracted with CHCl$_3$ (3×10 mL). The organic layer was dried, evaporated under reduced pressure, and the residue was purified by silica gel column chromatography eluting with 5% MeOH in CHCl$_3$, yielding 4.9 mg of compound 252b (85%) as a colorless solid, R$_f$=0.22.

Compound 248: A solution of {1S-benzyl-2R-hydroxy-3-[(3'S)iso-butyl-(2-oxopyrrolidin-3-yl)-amino]propyl}carbamic acid tert-butyl ester (252b, 5.0 mg, 0.012 mmol) in 20% TFA in CH$_2$Cl$_2$ (5 mL) was stirred for 30 min. The reaction mixture then was concentrated and redissolved CH$_2$Cl$_2$ (5 mL). To this solution was added triethylamine (0.1 mL), and, after 5 min, carbamate 22 (3.0 mg, 0.013 mmol). After stirring for 20 min, the solvent was evaporated under vacuum, and the residue was purified by silica gel column chromatography eluting with 5% MeOH in CHCl$_3$, yielding 4.5 mg of compound 248 (86%) as a colorless solid, R$_f$=0.15. $^1$H-NMR (400 MHz, CDCl$_3$): δ 7.29–7.17 (m, 5H), 6.05 (bs, 1H), 5.10 (bs, 1H), 4.88 (d, 1H, J=9.3 Hz), 3.84–3.63 (m, 7H), 3.34–3.28 (m, 2H), 2.93–2.87 (m, 2H), 2.46–2.43 (m, 2H), 2.31–2.05 (m, 4H), 1.95–1.87 (m, 2H), 1.77–1.70 (m, 1H), 0.94 (d, 3H, J=6.4 Hz), 0.87 (d, 3H, J=6.4 Hz.

Compound 249: A solution of {1S-benzyl-2R-hydroxy-3-[(3'S)-isobutyl(2-oxopyrrolidin-3-yl)-amino]propyl}carbamic acid tert-butyl ester (252b, 5.0 mg, 0.012 mmol) in 20% TFA in CH$_2$Cl$_2$ (5 mL) was stirred for 30 min. The reaction mixture then was concentrated and redissolved CH$_2$Cl$_2$ (5 mL). To this solution was added triethylamine (0.1 mL), and, after 5 min, carbamate 15 (3.4 mg, 0.013 mmol). After stirring for 20 min, the solvent was evaporated under vacuum, and the residue was purified by silica gel column chromatography eluting with 5% MeOH in CHCl$_3$, yielding 3.8 mg of compound 249 (67%) as a colorless solid, R$_f$=0.25. $^1$H-NMR (400 MHz, CDCl$_3$): δ 7.26–7.16 (m, 5H), 5.63 (d, 1H, J=5.2 Hz), 5.10 (bs, 1H), 5.00–4.97 (m, 1H), 3.98–3.92 (m, 2H), 3.86–3.72 (m, 2H), 3.71–3.61 (m, 5H), 3.40–3.25 (m, 2H), 3.05–2.95 (m, 1H), 2.92–2.81 (m, 1H), 2.75–2.69 (m, 1H), 2.53–2.37 (m, 2H), 2.33–2.18 (m, 2H), 1.95–1.83 (m, 2H), 1.62–1.52 (m, 3H), 0.95 (d, 3H, J=6.2 Hz), 0.88 (d, 3H, J=5.4 Hz).

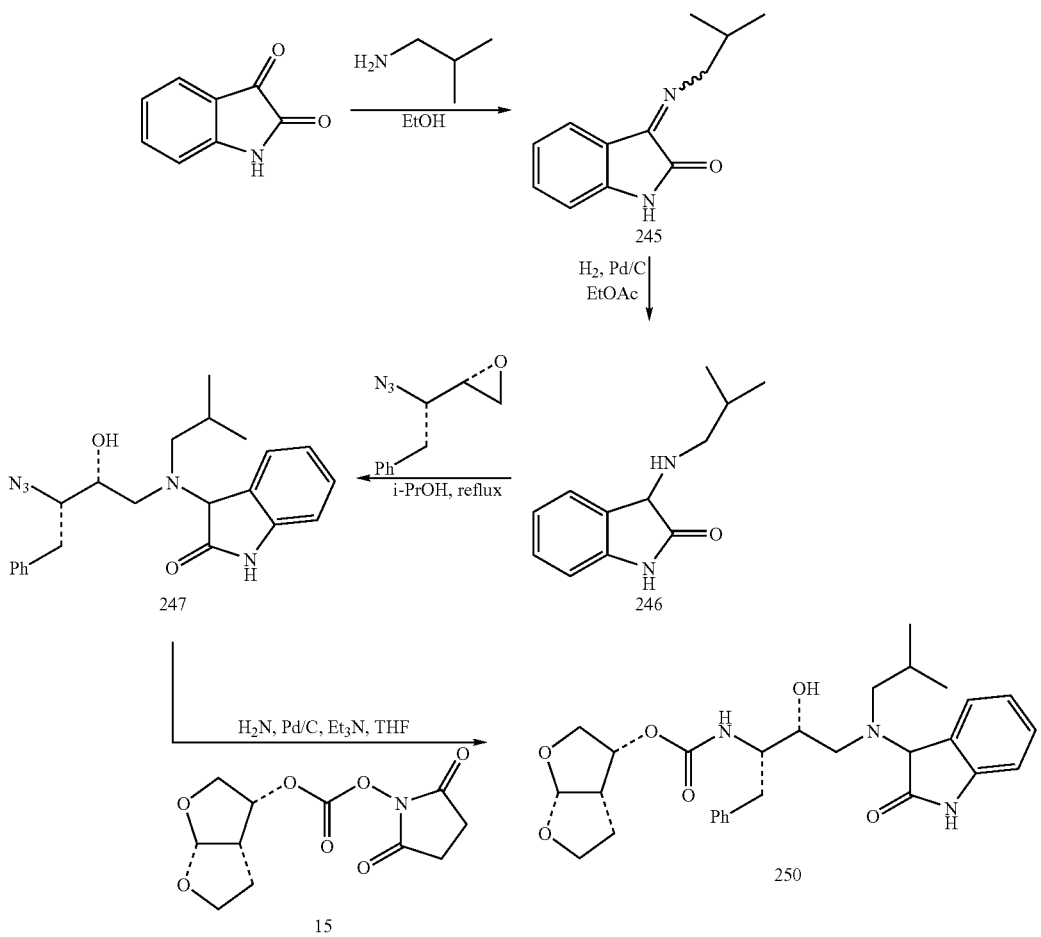

3-Isobutylimino-1,3-dihydro-indol-2-one (245). To a stirred suspension of isatin (5.00 g) in absolute EtOH (40 mL) was added isobutylamine (3.7 mL) at 23° C. and the mixture was stirred for 4 hours. The mixture then was filtered, and a bright yellow solid collected and recrystallized from EtOH to give 2.32 g, 34%, of bright yellow crystals. Imine formation resulted in an approximately 2:1 mixture of geometric isomers. $^1$H-NMR (300 MHz, CDCl$_3$): δ 10.05 (bs, major), 9.0 (bs, minor), 7.67 (d, J=7.2 Hz, major), 7.62 (d, J=7.2 Hz, minor), 7.34 (m, 2H), 7.04 (m, 3H), 7.86 (d, J=7.8 Hz, minor), 4.19 (d, J=6.9 Hz, minor), 3.82 (d, J=6.9 Hz, major), 2.31 (m, major), 2.12 (m, minor), 1.08 (d, J=6.3 Hz, major), 1.03 (d, J=6.9 Hz, minor); $^{13}$C-NMR (75 MHz, CDCl$_3$): δ 165.8, 154.6, 145.0, 133.3, 132.5, 127.1, 122.9, 122.2, 117.4, 111.9, 110.5, 62.3, 59.8, 30.5, 30.1, 21.0, 20.7.

3-Isobutylamino-1,3-dihydro-indol-2-one (246). To a solution of imine 255 (3.0 g) in EtOAc (50 mL) was added 10% Pd/C (0.10 g), and the mixture was hydrogenated under a balloon for 8 hours. The mixture was filtered through a pad of celite and concentrated in vacuo to afford an off-white solid. To this solid was added 100 mL of an anhydrous diethyl ether-HCl solution and the mixture was shaken for 10 minutes. The resulting light-pink colored salt was filtered and recrystallized from EtOH-ether to give 2.2 g (61%) of 3-isobutylamino-1,3-dihydro-indol-2-one hydrochloride. $^1$H-NMR (300 MHz, CD$_3$OD): δ 7.67 (d, J=8.1 Hz, 1H), 7.41 (t, J=7.8 Hz, 1H), 7.14 (t, J=7.8 Hz, 1H), 7.00 (d, J=7.8 Hz, 1H), 5.07 (s, 1H), 3.06 (dd, J=12.0, 7.2 Hz, 1H), 2.91 (dd, J=12.0, 6.9 Hz, 1H), 2.08 (m, 1H), 1.04 (d, J=1.8 Hz, 3H), 1.02 (d, J=1.5 Hz, 3H); $^{13}$C-NMR (75 MHz, CD$_3$OD): δ 172.9, 144.7, 132.5, 127.3, 124.2, 121.5, 11.2.1, 58.5, 53.4, 27.5, 20.4. The hydrochloride salt was converted to the free amine immediately prior to use in the next reaction by washing with NaHCO$_3$ and extracting with CH$_2$Cl$_2$. $^1$H-NMR (300 MHz, CDCl$_3$): δ 9.62 (s, 1H), 7.35 (d, J=7.5 Hz, 1H), 7.21 (t, J=7.5 Hz, 1H), 7.03 (t, J=7.2 Hz, 1H), 6.89 (d, J=7.8 Hz, 1H), 4.39 (s, 1H), 2.41 (dd, J=10.5, 6.6 Hz), 2.20 (dd, J=10.5, 6.9 Hz), 1.67 (m, 1H), 0.88 (d, J=2.4 Hz, 3H), 0.86 (d, J=2.4 Hz, 3H). Peaks at 2.41 and 2.20 combined for 3H due to overlap of the NH peak; $^{13}$C-NMR (75 MHz, CDCl$_3$): δ 180.4, 141.7, 128.8, 127.6, 125.0, 122.6, 110.2, 61.0, 52.7, 28.9, 20.6, 20.5.

(2R,3S)-3-[(3-Azido-2-hydroxy-4-phenyl-butyl)-isobutyl-amino]-1,3-dihydro-indol-2-one (247). To a solution of (2R,3S)-2-(1-azido-2-phenyl-ethyl)oxirane (64) (16.2 mg) in isopropanol (2 mL) was added freshly washed 3-isobutylamino-1,3-dihydro-indol-2-one (15.4 mg), and the solution was refluxed for 22 hours. The mixture was cooled and solvent removed under reduced pressure. Flash column chromatography (40, 70% EtOAc/hexane) afforded the azido alocohol (12.4 mg, 37%) as a 2:1 mixture of diastereomers. $^1$H-NMR (300 MHz, CDCl$_3$): δ 7.99 (s, minor), 7.77 (s, major), 7.37 (d, J=7.8 Hz), 7.32–7.20 (m), 7.12–7.05 (m), 6.89 (t, J=7.5 Hz, 2H), 4.46 (s, minor), 4.43 (s, major), 4.30 (bs, major), 4.04 (bs, minor), 3.82–3.76 (m), 3.65–3.59 (m), 3.56–3.53 (m), 3.30 (dd, J=12.9, 2.4 Hz), 3.00–2.91 (m), 2.76–2.69 (m), 2.60–2.47 (m), 2.07–1.99 (m), 1.84–1.80 (m), 1.59 (s, minor), 1.28–1.23 (m), 0.97–0.85 (m).

Compound 250. To a solution of azide 247 in dry THF (2 mL) was added mixed carbonate 15 (10.0 mg), triethylamine (10 μL), and 10% Pd/C (7.6 mg), and the mixture was hydrogenated under a balloon for 2 hours. The mixture was filtered through a pad of celite and the filtrate concentrated in vacuo. The residue was chromatographed over silica gel (60, 100% EtOAc/hexane) to afford compound 250 as a white solid (10.9 mg, 60%) as a mixture of diasteromers. $^1$H-NMR (500 MHz, CD$_3$OD): δ 7.43 (d, J=7.5 Hz, 1H), 7.39 (d, J=7.4 Hz), 7.25–7.13 (m), 7.04 (t, J=6.8 Hz, 1H), 6.99 (t, J=7.4 Hz, 1H), 6.86 (d, J=7.8 Hz), 5.57 (t, J=4.9 Hz), 4.56 (s), 4.54 (s), 3.92–3.88 (m), 3.78–3.63 (m), 3.24–3.22 (m), 3.15 (dd, J=14.0, 3.6 Hz), 2.96 (dd, J=13.9, 3.6 Hz), 2.86–2.84 (m), 2.81 (m), 2.77 (d, J=5.3 Hz), 2.69–2.65 (m), 2.60–2.53 (m), 2.32–2.28 (m), 2.06–2.01 (m), 1.83–1.78 (m), 1.57–1.48 (m), 1.40–1.34 (m), 1.29 (s), 0.93–0.84 (m).

| No. | | IC$_{50}$ (nM) |
|---|---|---|
| 253 | [structure] | 1.0 |
| 254 | [structure] | 1.0 |
| 255 | [structure] | |

| No. | | IC$_{50}$ (nM) |
|---|---|---|
| 256 | | 1.7 |
| 257 | | 2.9 |
| 258 | | 3.9 |
| 259 | | 2.8 |
| 260 | | |

-continued

| No. | | IC$_{50}$ (nM) |
|---|---|---|
| 261 | | 2.2 |
| 262 | | |
| 263 | | |
| 264 | | |
| 265 | | |

| No. | | IC$_{50}$ (nM) |
|---|---|---|
| 267 | | |
| 268 | | |
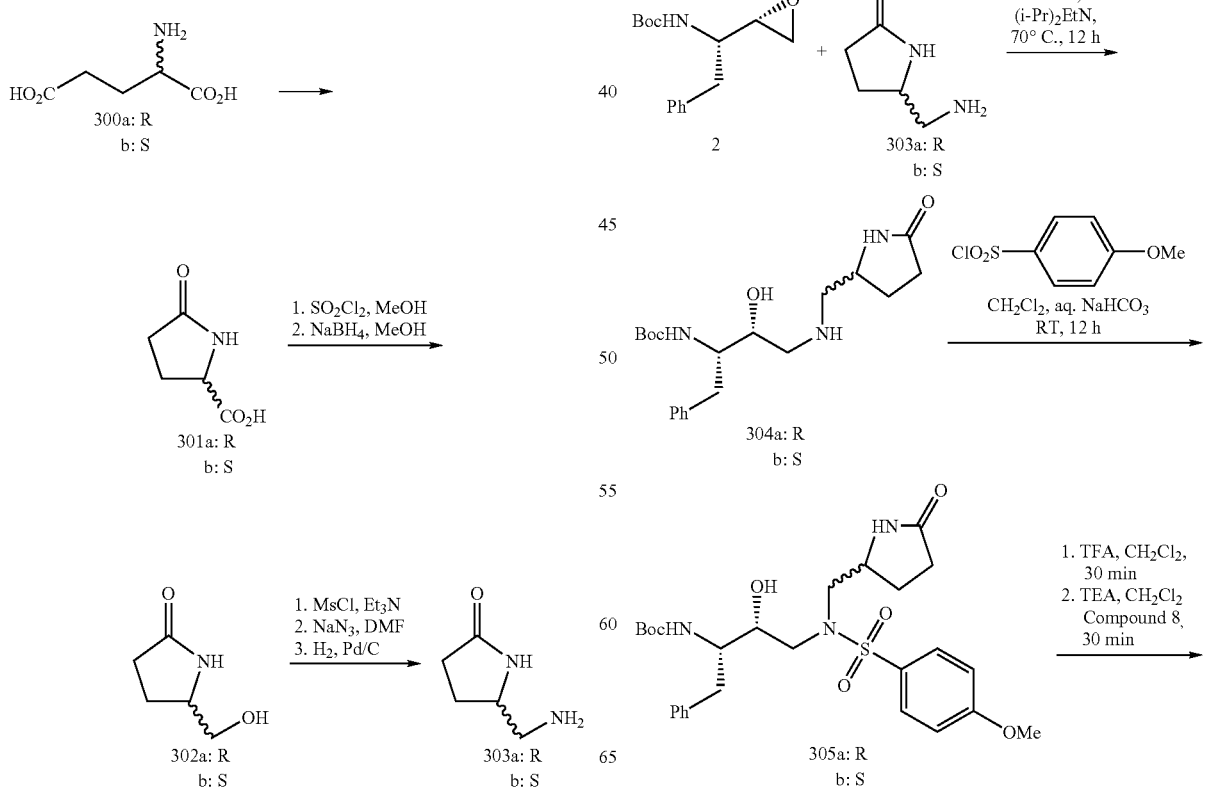
Scheme A.

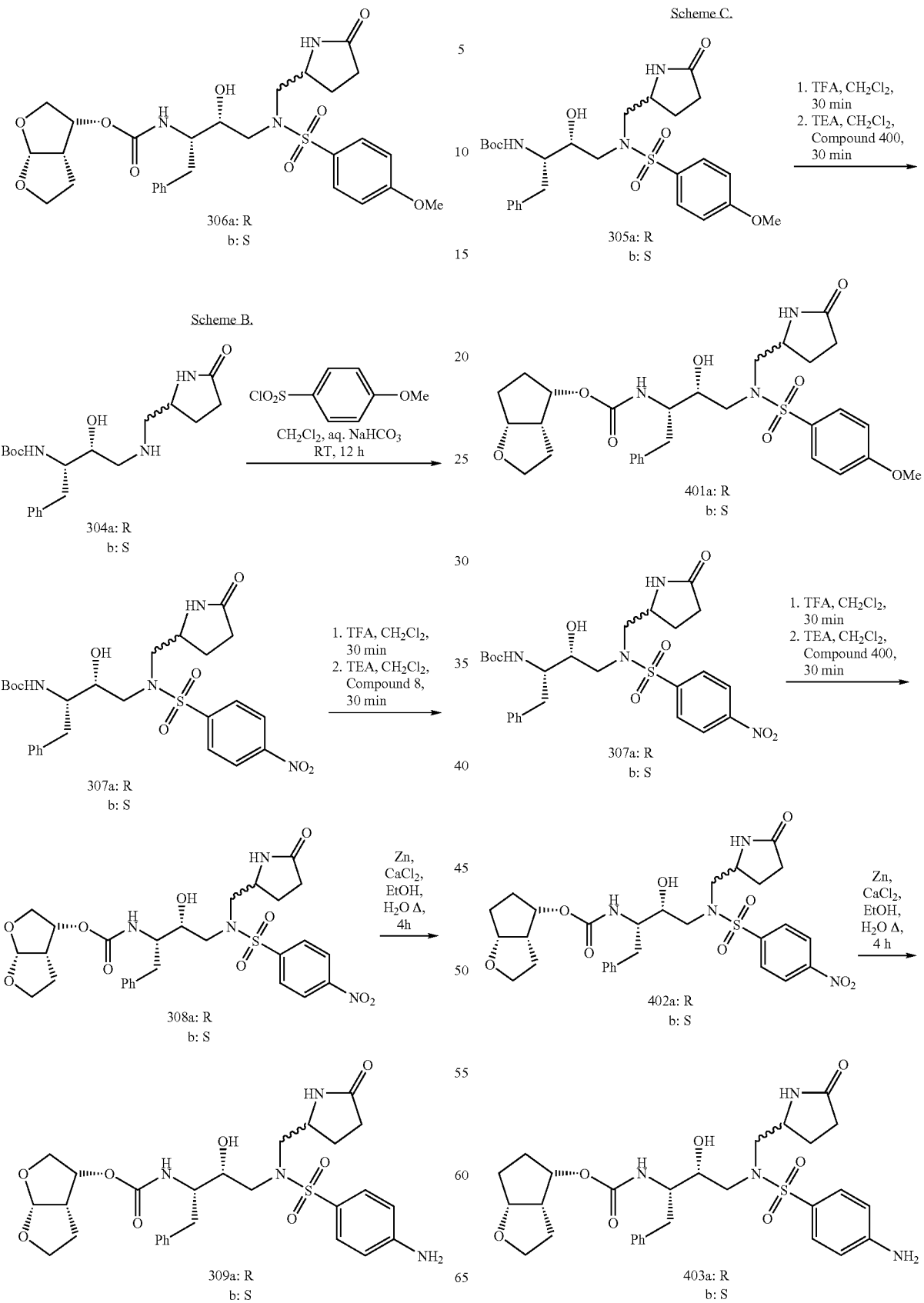

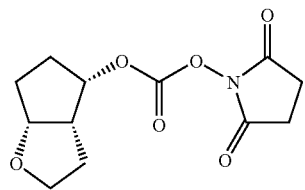
40
| No. | | Scheme No. | IC$_{50}$ (nM) |
|---|---|---|---|
| | | 528b | 386 |
| 269 | | 528a | 3.4 |
| 270 | | | 6.4 |
| 271 | | 305a | 3 |

-continued

| No. | | Scheme No. | IC$_{50}$ (nM) |
|---|---|---|---|
| | 40 | | |
| 272 | | 305b | 3.42 |
| 273 | | 306a | 17 (pM) |
| 276 | | 309a | 20 (pM) |
| 265 | | 309b | |

-continued
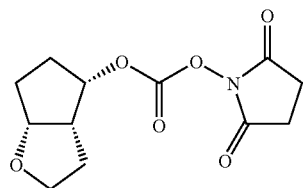
40
| No. | Scheme No. | IC$_{50}$ (nM) |
|---|---|---|
| 277 | 401a | 0.1 |
| 278 | 401b | 0.16 |
| 279 | 402a | 0.34 |
| 280 | 402b | |

-continued
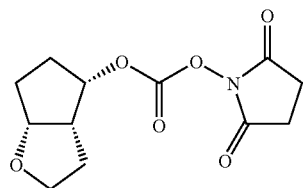
40
| No. | Scheme No. | IC$_{50}$ (nM) |
|---|---|---|
| 281 | 403a | 26 (pM) |
| 282 | | |
| 283 | 306b | 14 (pM) |
| | 307a | 7 |

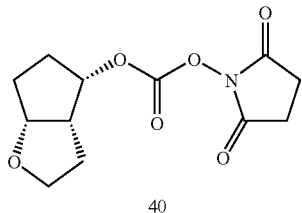

40

| No. | | Scheme No. | IC$_{50}$ (nM) |
|---|---|---|---|
| 274 | [structure with BocHN, OH, Ph, sulfonyl-NO$_2$, pyrrolidinone] | 307b | 12 |
| 275 | [structure with bis-tetrahydrofuran carbamate, OH, Ph, sulfonyl-NO$_2$, pyrrolidinone] | 308a | 0.1 |
|  | [structure with bis-tetrahydrofuran carbamate, OH, Ph, sulfonyl-NO$_2$, pyrrolidinone] | 308b | 0.37 |

{(1S)-Benzyl-(2R)-hydroxy-3-[(4-methoxybenzene-sulfonyl)-(5-oxopyrrolidin-(2R)-ylmethyl)amino]-propyl}carbamic acid tert-butyl ester (305a)

A solution of {(1S)-benzyl-(2R)-hydroxy-3-[(5-oxopyr-rolidin-(2R)-ylmethyl)amino]propyl}-carbamic acid tert-butyl ester (304a, 19.4 mg, 0.051 mmol) and 4-methoxy-benzenesulfonyl chloride (32.0 mg, 0.154) in CH$_2$Cl$_2$ (4 mL) and sat. aq. NaHCO$_3$ (4 mL) was stirred overnight at room temperature. The mixture then was extracted with CHCl$_3$ (3×5 mL). The organic layer was dried over NaSO$_4$, and the residue was purified by silica gel column chromatography eluting with 10% MeOH in CHCl$_3$, yielding 22 mg of compound 305a (78%) as a colorless solid, R$_f$=0.45. $^1$H NMR (300 MHz, CDCl$_3$): δ 1.33 (s, 9H), 1.58–1.76 (m, 1H), 2.10–2.26 (m, 1H), 2.27–2.42 (m, 2H), 2.73–2.83 (m, 1H), 2.84–3.07 (m, 3H), 3.19 (t, 2H, J=14.4 Hz), 3.70–3.84 (m, 1H), 3.85 (s, 3H), 3.92–4.05 (m, 2H), 4.90 (bs, 1H), 6.95 (d, 2H, J=9.0 Hz), 7.18–7.30 (m, 5H), 7.68 (d, 2H, J=9.0 Hz), 7.37 (bs, 1H).

{(1S)-Benzyl-(2R)-hydroxy-3-[(4-nitrobenzene-sulfonyl)-(5-oxopyrrolidin-(2R)-ylmethyl)amino]propyl}-carbamic acid tert-butyl ester (307a)

A solution of {(1S)-benzyl-(2R)-hydroxy-3-[(5-oxopyr-rolidin-(2R)-ylmethyl)amino]propyl}carbamic acid tert-butyl ester (304a, 29.0 mg. 0.0768 mmol) and 4-nitrobenze-nesulfonyl chloride (51.0 mg 0.230) in CH$_2$Cl$_2$ (1 mL) and sat. aq. NaHCO$_3$ (1 mL) was stirred overnight at room temperature. The mixture then was extracted with CHCl$_3$ (3×5 mL). The organic layer was dried over NaSO$_4$, and the residue was purified by silica gel column chromatography eluting with 6% MeOH in CHCl$_3$, yielding 38 mg of compound 307a (88%) as a colorless solid, R$_f$=0.20. $^1$H NMR (400 MHz, CDCl$_3$): δ 1.37 (s, 9H), 1.60–1.74 (m, 1H), 2.23–2.30 (m, 1H), 2.35–2.40 (m, 2H), 2.88–2.93 (m, 1H), 2.94–3.08 (m, 3H), 3.36–3.42 (m, 2H), 2.67–3.84 (m, 1H), 3.92–4.05 (m, 2H), 4.69 (bs, 1H), 7.20–7.33 (m, 6H), 7.96 (d, 2H, J=6.8 Hz), 8.36 (d, 2H, J=6.8 Hz).

Compound 273

A solution of {(1S)-benzyl-(2R)-hydroxy-3-[(4-methoxy-benzenesulfonyl)-(5-oxopyrrolidin-(2R)-ylmethyl)amino]propyl}carbamic acid tert-butyl ester (305a, 8.2 mg, 0.0150 mmol) in 20% TFA in CH$_2$Cl$_2$ (5 mL) was stirred for 30 minutes. The reaction mixture then was concentrated and redissolved CH$_2$Cl$_2$ (2 mL). Triethylamine (0.00104 mL) was added to this solution, and after 5 minutes carbamate 528b (5.7 mg. 0.0749 mmol) was added. After stirring for 20 minutes, the solvent was evaporated under vacuum, and the residue was purified by silica gel column chromatography eluting with 5% MeOH in CH$_2$Cl$_2$, yielding 7.7 mg of compound 306a (83%) as a colorless solid, R$_f$=0.20. $^1$H NMR (400 MHz, CDCl$_3$): δ 1.52–1.73 (m, 3H), 2.15–2.26 (m, 1H), 2.35–2.41 (m, 2H), 2.70–2.78 (m, 1H), 2.81–3.01 (m, 3H), 3.04–3.15 (m, 1H), 3.24–3.31 (m, 2H), 3.61–3.80 (m, 3H), 3.86 (s, 3H), 3.92–4.01 (m, 2H), 4.03–4.13 (m, 2H), 4.97–5.02 (m, 1H), 5.60 (bs, 1H), 5.61 (d, 1H, J=5.4 Hz), 6.97 (d, 2H, J=7.2 Hz), 7.19–7.26 (m, 5H), 7.70 (d, 2H, J=7.2 Hz), 7.91 (bs, 1H).

Compound 274

A solution of {(1S)-benzyl-(2R)-hydroxy-3-[(4-nitrobenzenesulfonyl)-(5-oxopyrrolidin-(2R)-yl-methyl)amino]propyl}carbamic acid tert-butyl ester (307a, 15.0 mg. 0.0267 mmol) in 20% TFA in CH$_2$Cl$_2$ (5 mL) was stirred for 30 minutes. The reaction mixture then was concentrated and redissolved CH$_2$Cl$_2$ (2 mL). Triethylamine (0.00185 mL) was added to this solution, and after 5 minutes carbamate 28b (10.1 mg, 0.0373 mmol) was added. After stirring for 20 minutes, the solvent was evaporated under vacuum, and the residue was purified by silica gel column chromatography eluting with 6% CH$_2$Cl$_2$ in CHCl$_3$, yielding 13.3 mg of compound 308a (81%) as a colorless solid, R$_f$=0.19. $^1$H NMR (500 MHz, CDCl$_3$): δ 1.59–1.69 (m, 2H), 1.70–1.80 (m, 1H), 2.18–2.28 (m, 1H), 2.34–2.41 (m, 2H), 2.70–2.77 (m, 1H), 2.88–2.93 (m, 1H), 3.03–3.16 (m, 3H), 3.22–3.28 (m, 2H), 3.60–3.69 (m, 1H), 3.71–3.76 (m, 1H), 3.78–3.83 (m, 1H), 3.91–3.99 (m, 2H), 4.00–4.12 (m, 2H), 4.99–5.04 (m, 1H), 5.57 (bs, 1H), 5.63 (d, 1H, J=5.2 Hz), 7.19–7.28 (m, 5H), 7.95 (d, 2H, J=8.8 Hz), 8.14 (bs, 1H), 8.36 (d, 2H, J=8.8 Hz).

Compound 276

A solution of compound 308a (20 mg, 0.032 mmol), zinc (65 mg, 0.99 mmol), calcium chloride (CaCl$_2$) (2.5 mg, 0.023) in ethanol (EtOH) (4 mL), and water (1 mL) were refluxed for 5.5 hours. Sat. aq. NaHCO$_3$ was added to this mixture (5 mL), then the reaction mixture was extracted with CHCl$_3$ (3×5 mL). The organic layer was dried over NaSO$_4$, and the residue was purified by silica gel column chromatography eluting with 10% MeOH in CHCl$_3$, yielding 9.0 mg of compound 309a (47%) as a colorless solid, R$_f$=0.24. $^1$H NMR (400 MHz, CDCl$_3$): δ 1.60–1.69 (m, 2H), 1.73–1.81 (m, 1H), 2.15–2.16 (m, 1H), 2.31–2.41 (m, 2H), 2.60–2.71 (m, 2H), 2.72–2.93 (m, 2H), 3.07–3.11 (m, 1H), 3.22–3.35 (m, 2H), 3.60–3.72 (m, 2H), 3.81–3.99 (m, 4H), 4.00–4.05 (m, 1H), 4.97–5.03 (m, 1H), 5.35 (bs, 1H), 5.63 (d, 1H, J=5.2 Hz), 6.66 (d, 2H, J=11.2 Hz), 8.14 (bs, 1H), 7.19–7.28 (m, 5H), 7.53 (d, 2H, J=11.2 Hz)

Compound 277

A solution of {(1S)-benzyl-(2R)-hydroxy-3-[(4-methoxy-benzenesulfonyl)-(5-oxopyrrolidin-(2R)-ylmethyl)amino]propyl}carbamic acid tert-butyl ester (305a, 11.0 mg, 0.0201 mmol) in 20% TFA in CH$_2$Cl$_2$ (5 mL) was stirred for 30 minutes. The reaction mixture then was concentrated and redissolved CH$_2$Cl$_2$ (2 mL). Triethylamine (0.00084 mL) was added to this solution, and after 5 minutes compound 40 (6.5 mg, 0.024 mmol) was added. After stirring for 20 minutes, the solvent was evaporated under vacuum, and the residue was purified by silica gel column chromatography eluting with 5% MeOH in CHCl$_3$, yielding 6.5 mg of compound 401a (54%) as a colorless solid, R$_f$=0.22. $^1$H NMR (400 MHz) CDCl$_3$): δ 1.46–1.56 (m, 1H), 1.59–1.67 (m, 2H), 1.93–2.08 (m, 3H), 2.18–2.25 (m, 2H), 2.28–2.41 (m, 3H), 2.60–2.72 (m, 2H), 2.95–3.22 (m, 5H), 3.54–3.60 (m, 1H), 3.80–3.87 (m, 3H), 3.88 (s, 3H), 3.92–4.00 (m, 1H), 4.35–4.41 (m, 1H), 4.92 (bs, 1H), 5.33 (m, 1H), 6.99 (d, 2H, J=8.8 Hz), 7.18–7.29 (m, 5H), 7.71 (d, 2H, J=8.8 Hz).

Compound 279

A solution of {(1S)-benzyl-(2R)-hydroxy-3-[(4-nitrobenzenesulfonyl)-(5-oxopyrrolidin-(2R)-yl-methyl)amino]propyl}carbamic acid tert-butyl ester (307a, 19.0 mg, 0.0337 mmol) in 20% TFA in CH$_2$Cl$_2$ (5 mL) was stirred for 30 minutes. The reaction mixture then was concentrated and redissolved CH$_2$Cl$_2$ (2 mL). Triethylamine (0.00091 mL) was added to this solution, and after 5 minutes compound 400 (12.0 mg, 0.0439 mmol) was added. After stirring for 20 minutes, the solvent was evaporated under vacuum, and the residue was purified by silica gel column chromatography eluting with 5% MeOH in CHCl$_3$, yielding 16.8 mg of 402a (81%) as a colorless solid, R$_f$=0.21. $^1$H NMR (400 MHz, CDCl$_3$): δ 1.44–1.53 (m, 1H), 1.56–1.62 (m, 2H), 1.90–2.06 (m, 5H), 2.18–2.24 (m, 1H), 2.28–2.41 (m, 2H), 2.60–2.69 (m, 1H), 2.70–2.78 (m, 1H), 2.99–3.22 (m, 4H), 3.23–3.35 (m, 1H), 3.54–3.62 (m, 1H), 3.80–3.90 (m, 3H), 3.95–4.02 (m, 1H), 4.31–4.40 (m, 1H), 4.91 (bs, 1H), 5.22 (m, 1H), 7.20–7.30 (m, 5H), 7.98 (d, 2H, J=8.7 Hz), 8.36 (d, 2H, J=8.7 Hz).

(5R)-Hydroxymethylpyrrolidin-2-one (302a)

To 5-oxopyrrolidine-(2R)-carboxylic acid (301a, 5.00 g, 38.7 mmol) in MeOH (50 mL) and DMF (0.5 mL) was added SOCl$_2$ (3.4 mL, 45.5 mmol) dropwise at 0° C. After stirring overnight, the solvent was evaporated under vacuum, CHCl$_3$ (70 mL) and saturated aq. NaHCO$_3$ (30 mL) were added; and the mixture was extracted with CHCl$_3$ (3×10 mL). The organic layer was dried over NaSO$_4$. Distillation under vacuum (1 mm) gave 3.35 g (60%) of 5-oxopyrrolidine-(2R)-carboxylic acid methyl ester, bp. 140° C. Sodium borohydride (44.28 mmol) at 0° C. was added to this ester (3.17 g, 22.14 mmol) in EtOH (75 mL). After stirring overnight, the reaction mixture was quenched with sat. aq. NH$_4$Cl solution. The white precipitate was filtered, and the residue was washed with ethyl acetate (EtOAc). Evaporation of the solvent gave 2.30 g (90%) of compound 302a, which was used without further purification. $^1$H NMR (300 MHz, CDCl$_3$): δ 1.67–1.79 (m, 1H), 2.03–2.12 (m, 1H), 2.15–2.35 (m, 2H), 3.35–3.43 (m, 1H), 3.56–3.62 (m, 1H), 3.69–3.77 (m, 1H), 4.81 (bs, 1H), 7.55 (bs, 1H).

(5R)-Aminomethylpyrrolidine-2-one (303a)

To a solution of (5R)-hydroxymethyl-pyrrolidin-2-one (302a, 0.800 g, 6.96 mmol) and Et$_3$N (1.94 mL, 13.91 mmol) in CH$_2$Cl$_2$ (40 ml) at 0° C. was added MsCl (0.591 mL, 7.65 mmol). After stirring overnight, CHCl$_3$ (70 mL) and saturated aq. NaHCO$_3$ (30 mL) were added, and the mixture was extracted with CHCl$_3$ (6×20 mL) and EtOAc (6×20 mL). The organic layer was dried over NaSO$_4$, and the residue was purified by silica gel column chromatography by eluting with 7% MeOH in CHCl$_3$, yielding 864 mg of the corresponding mesylate (65%) as a colorless solid, R$_f$=0.21. A solution of this mesylate (0.306 g, 1.60 mmol) and NaN$_3$ (0.208 g, 3.20 mmol) in DMF (5 mL) was stirred for 6 h at 80° C. Then the solvent was removed, and the residue was purified by silica gel column chromatography eluting with 8% MeOH in CHCl$_3$, yielding 236 mg of corresponding azide (98%) as a colorless solid, R$_f$=0.30. A solution of this azide (72.5 mg, 0.518 mmol) in EtOAc (10 mL) was hydrogenated with Pd/C (10%) at 20 psi for 4 hours. Filtration through a pad of silica gel (5 g) with MeOH (50 mL) gave 53 mg of compound 303a (90%). $^1$H NMR (300 MHz, CDCl$_3$): δ 1.64–1.71 (m, 1H), 2.11–2.19 (m, 1H), 2.20–2.27 (m, 2H), 2.57–2.64 (m, 1H), 2.65–2.77 (m, 1H), 2.81 (bs, 2H), 3.63–3.67 (m, 1H), 7.59 (bs, 1H).

{(1S)-Benzyl-(2R)-hydroxy-3-[(5-oxopyrrolidin-(2R)-ylmethyl)amino]propyl}carbamic acid tert-butyl ester (304a)

A solution of tert-butyl [S—(R*,R*)]-(–)-(1-oxiranyl-2-phenylethyl)carbamate (2, 65.0 mg, 0.247 mmol), (5R)-aminomethylpyrrolidin-2-one (303a, 120 mg, 0.105 mmol), and diisopropylethylamine ((iPr)$_2$EtN) (0.200 mL, 1.15 mmol) in isopropanol (10 mL) was heated under stirring at 70° C. for 14 hours. The solvent was evaporated under vacuum, and the residue was purified by silica gel column chromatography eluting with 15% MeOH in CHCl$_3$, yielding 71 mg of compound 272 (76%) as a colorless solid, R$_f$=0.22. $^1$H NMR (400 MHz, CDCl$_3$): δ 1.34 (s, 9H), 1.63–1.78 (m, 1H), 2.12–2.28 (m, 1H), 2.29–2.38 (m, 2H), 2.53–2.63 (m, 1H), 2.64–2.73 (m, 1H), 2.74–2.86 (m, 2H), 2.92–3.00 (m, 2H), 3.52–3.59 (m, 1H), 3.72–3.90 (m, 2H), 4.88 (d, 1H, J=9.0 Hz), 7.18–7.22 (m, 3H), 7.26–7.30 (m, 2H), 7.42 (bs, 1H).

Compound 281

A solution of compound 402a (15.0 mg, 0.024 mmol), zinc (50 mg, 0.77 mmol), CaCl$_2$ (2.0 mg, 0.018) in EtOH (1.5 mL), and water (0.5 mL) was refluxed for 4 hours. Sat. aq. NaHCO$_3$ (5 mL) was added to this mixture, then the mixture was extracted with CHCl$_3$ (3×5 mL). The organic layer was dried over Na$_2$SO$_4$, and the residue was purified by silica gel column chromatography eluting with 10% MeOH in CHCl$_3$, yielding 8.0 mg of compound 403a (57%) as a colorless solid, R$_f$=0.23. $^1$H NMR (400 MHz, CDCl$_3$): δ 149–1.56 (m, 1H), 1.59–1.64 (m, 2H), 1.83–1.92 (m, 3H), 1.93–2.05 (m, 2H), 2.15–2.25 (m, 1H), 2.30–2.41 (m, 2H), 2.58–2.65 (m, 1H), 2.65–2.73 (m, 1H), 2.95–3.03 (m, 1H), 3.04–3.20 (m, 4H), 3.53–3.62 (m, 1H), 3.78–3.88 (m, 3H), 3.92–4.0 (m, 1H), 4.35–4.41 (m, 1H), 4.92 (bs, 1H), 5.38 (m, 1H), 6.67 (d, 2H, J=8.7 Hz), 7.26–7.36 (m, 5H), 7.54 (d, 2H, J=8.7 Hz).

Compounds 284 and 285

Compound 284

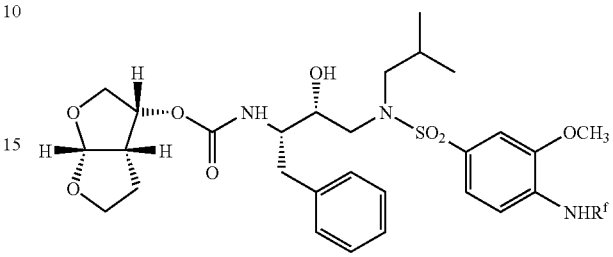

Compound 285

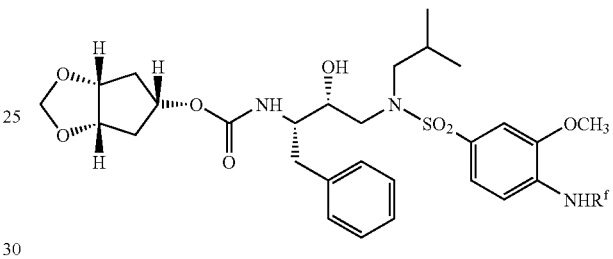

For compounds 284 and 285, R$^f$ is defined as hydro or C$_{1-6}$alkyl. Preferably, R$^f$ is hydro, methyl, or ethyl. Compounds 284 and 285 were prepared by the methods described above. The ligand

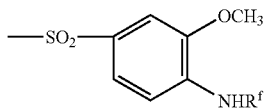

was prepared by the method disclosed in A. D. Rao et al., *J. Indian Chem. Soc.*, 62:3, pages 234–237 (1985).

Obviously, many modifications and variations of the invention as hereinbefore set forth can be made without departing from the spirit and scope thereof, and, therefore, only such limitations should be imposed as are indicated by the appended claims.

What is claimed is:
1. A compound having a formula

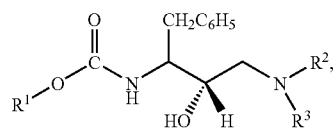

wherein R$^1$ is

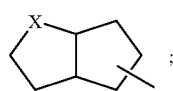

R² is selected from the group consisting of

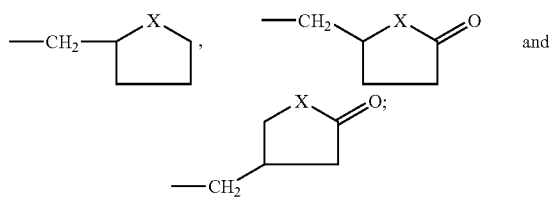

R³ is

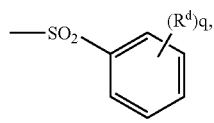

X is selected from the group consisting of O, NR$^e$, and S;
R$^d$ is selected from the group consisting of C$_{1-4}$alkyl, C$_{2-6}$alkenyl, C$_{1-3}$alkyleneC$_{3-8}$heterocycloalkyl, OR$^e$, C$_{1-3}$alkyleneOR$^e$, N(R$^e$)$_2$, SR$^e$, halo, nitro, CHO, cyano, NC, C(=O)R$^e$, OC(=O)R$^e$, C(=O)OR$^e$, C(=O)N(R$^e$)$_2$, CH=NOH, CH=CHCH$_2$OH, N(R$^e$)COR$^e$, and C$_{1-3}$alkyleneN(R$^e$)$_2$, or two R$^d$ groups are taken together to form a five-, six-, or seven-mernbered aliphatic ring optionally containing one or two of the moiety X;

R$^e$ is selected from the group consisting of hydro, C$_{1-6}$alkyl, C$_{2-6}$alkenyl, aryl, heteroaryl, C$_{1-8}$cycloalkyl, THP, Ts, Boc, and C$_{3-8}$heterocycloalkyl;

q is 0 through 3;

or a pharmaceutically acceptable salt thereof.

2. The compound of claim 1 wherein R¹ is

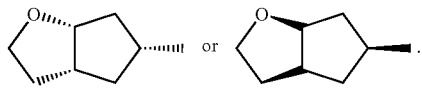

3. The compound of claim 1 wherein R² is selected from the group consisting of

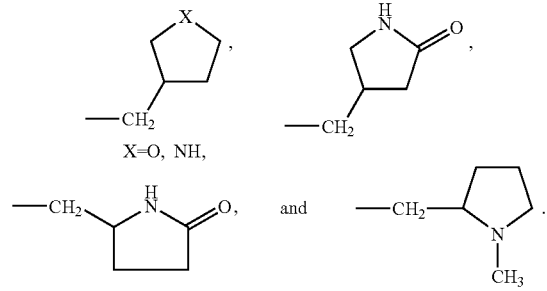

4. The compound of claim 1 wherein R² is selected from the group consisting of

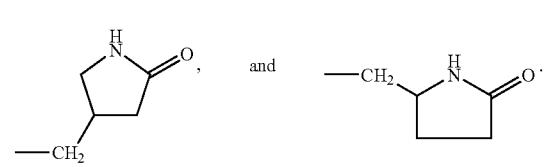

5. The compound of claim 2 wherein R$^d$, independently, is selected from the group consisting of CH$_2$OH, NH$_2$, OH, CH$_3$, CH$_2$CH$_3$, CH$_2$NH$_2$, CHO, Cl, F, nitro, OTHP, OCH$_3$, CH$_2$NHCH$_3$, CH=N—OH, and CH$_2$OCH$_3$, or two R$^d$ groups are taken together with the carbons to which they are attached to form

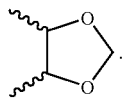

6. The compound of claim 1 wherein said compound has an IC$_{50}$ value vs. HIV-1 protease of less than about 500 nM.

7. The compound of claim 6 wherein said compound has an IC$_{50}$ value vs. HIV-1 protease of less than about 20 nM.

8. A compound of claim 1 selected from the group consisting of

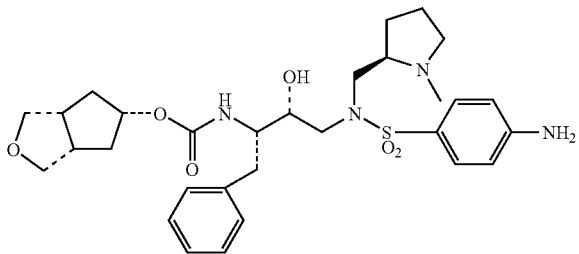

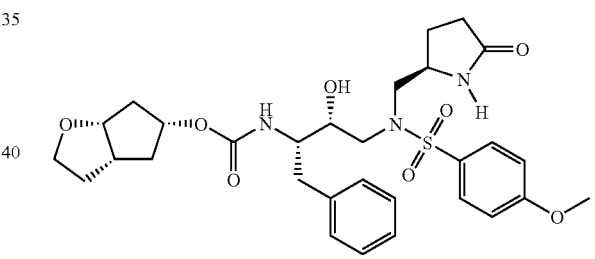

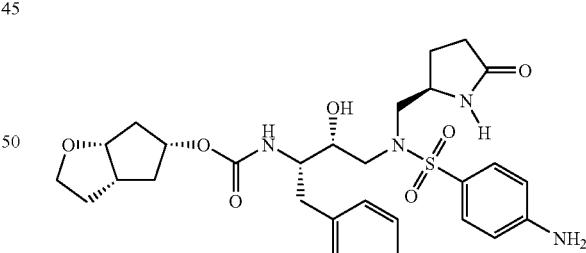

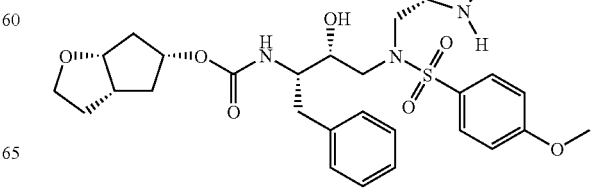

-continued
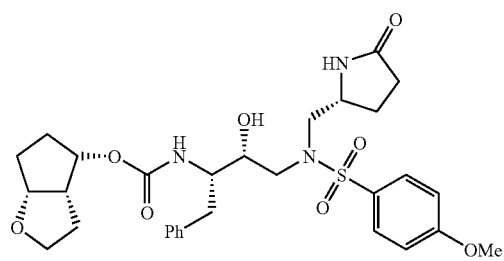
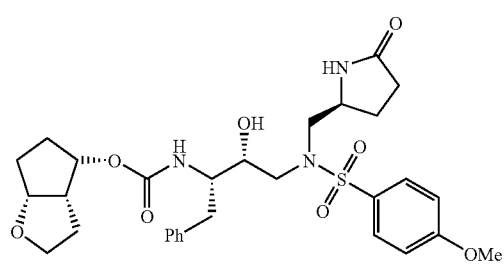
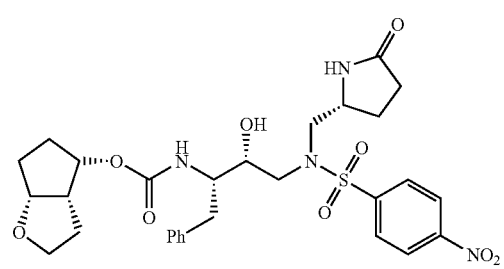
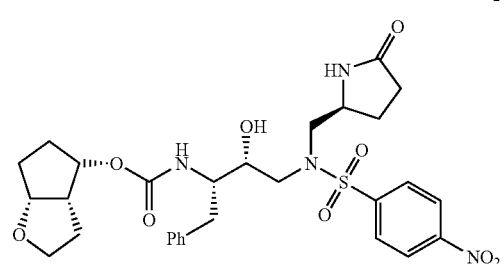
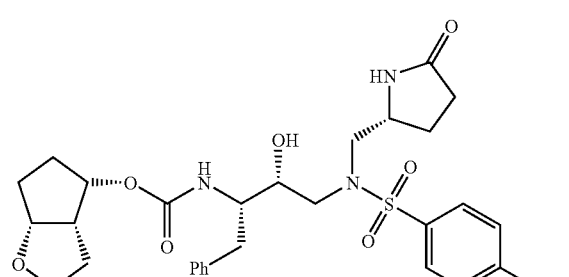
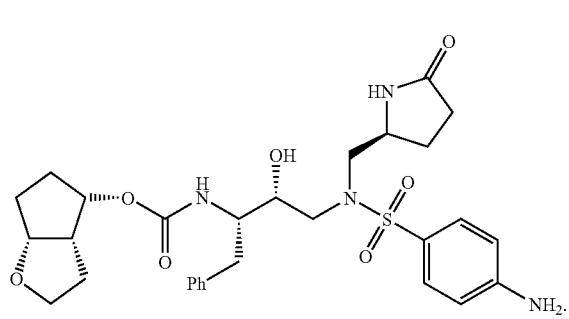
9. A compound having a formula
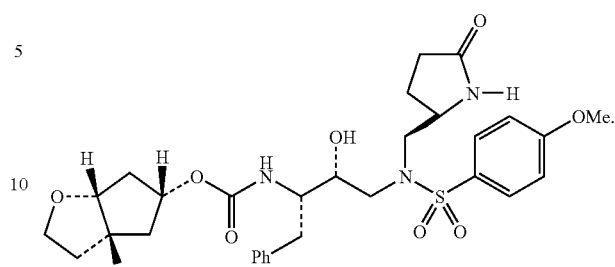
10. A compound having a formula
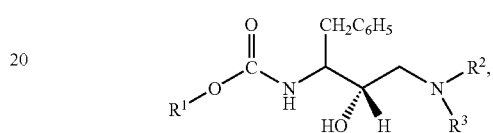
wherein R¹ is
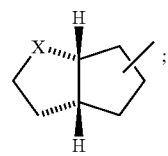
R² is selected from the group consisting of $C_{1-6}$alkyl, $C_{2-6}$alkenyl, $C_{1-3}$alkyleneN(R$^e$)$_2$, heterocycloalkyl, —NH$_2$, —NHBoc, $C_{1-3}$alkyleneheterocycloalkyl,
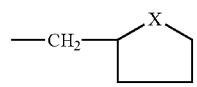
optionally substituted with oxo(=O),
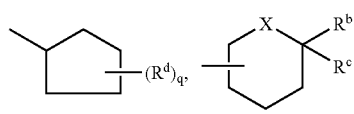
optionally substituted with oxo,
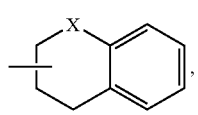
optionally substituted with oxo,
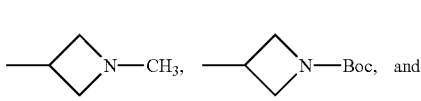

-continued

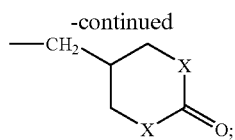

R³ is selected from the group consisting of

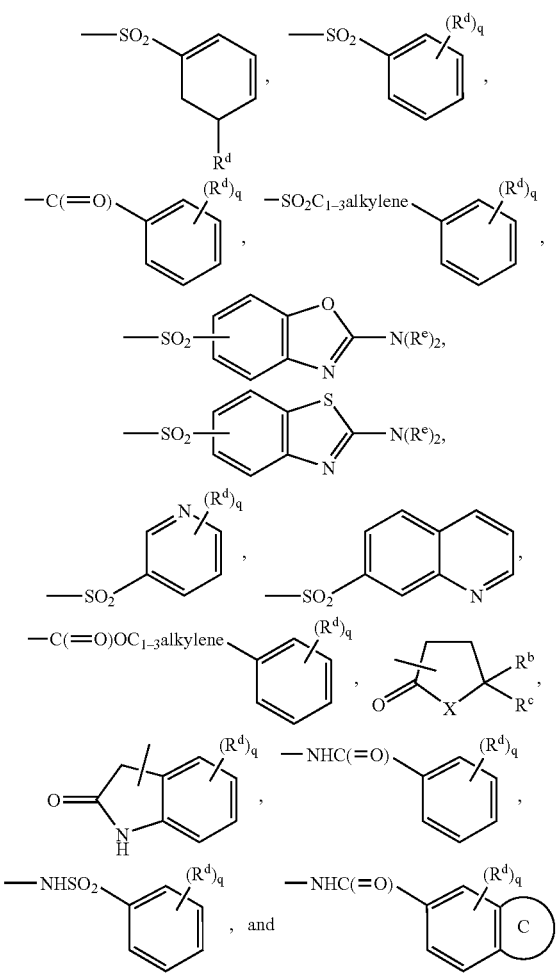

X is selected from the group consisting of O, NR$^e$, and S;

C is a five- or six-membered aliphatic ring containing one to three of the moiety X, and optionally substituted with oxo;

R$^b$ and R$^c$, independently, are selected from the group consisting of hydro, OH, C$_{1-3}$alkyl, C$_{1-3}$alkyleneOH, and C$_{1-3}$alkyleneN(R$^e$)$_2$, or R$^b$ and R$^c$ are taken together to form a five-, six-, or seven-membered aliphatic ring optionally containing one or two of the moiety X;

R$^d$ is selected from the group consisting of C$_{1-4}$alkyl, C$_{2-6}$alkenyl, C$_{1-3}$alkyleneC$_{3-8}$heterocycloalkyl, OR$^e$, C$_{1-3}$alkyleneOR$^e$, N(R$^e$)$_2$, SR$^e$, halo, nitro, CHO, cyano, NC, C(=O)R$^e$, OC(O)R$^e$, C(=O)OR$^e$, C(=O)N(R$^e$)$_2$, CH=NOH, CH=CHCH$_2$OH, N(R$^e$)COR$^e$, and C$_{1-3}$alkyleneN(R$^e$)$_2$, or two R$^d$ groups are taken together to form a five-, six-, or seven-membered aliphatic ring optionally containing one or two of the moiety X;

R$^e$ is selected from the group consisting of hydro, C$_{1-6}$alkyl, C$_{2-6}$alkenyl, aryl, heteroaryl, C$_{3-8}$cycloalkyl, THP, Ts, Boc, and C$_{3-8}$heterocycloalkyl;

q is 0 through 3;

or a pharmaceutically acceptable salt thereof.

11. A compound having a formula

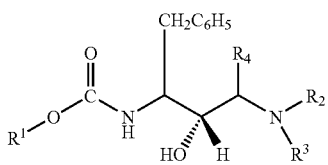

wherein R¹ is selected from the group consisting of C$_{1-6}$alkyl, aryl, C$_{1-3}$alkyleneheteroaryl,

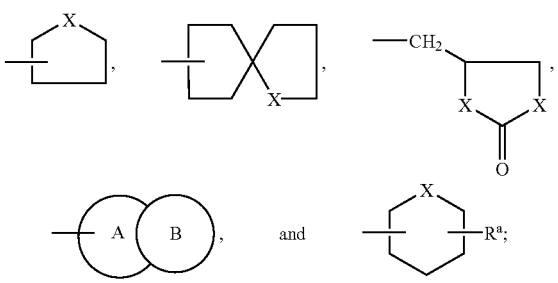

R² is selected from the group consisting of

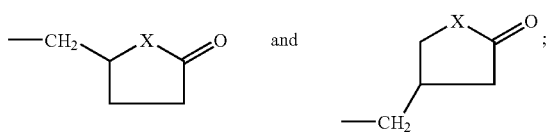

R³ is selected from the group consisting of

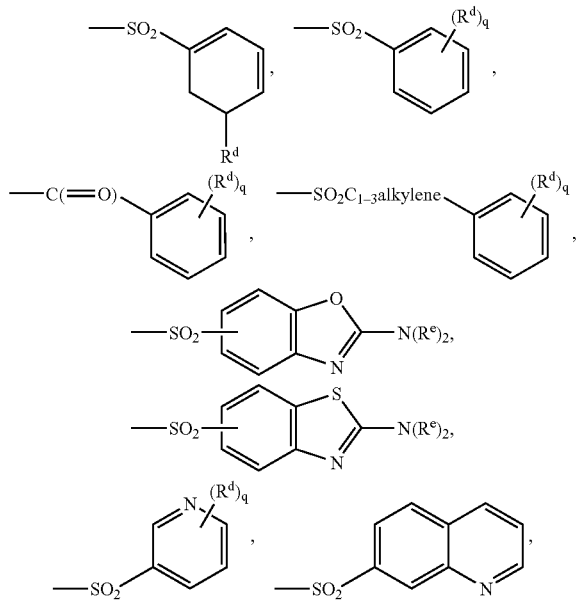

-continued

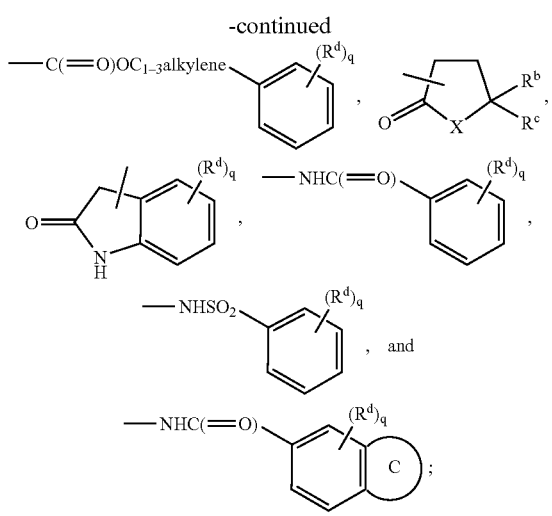

X is selected from the group consisting of O, NR$^e$, S, SO, and SO$_2$;

A and B, independently, are a five-, six-, or seven-membered aliphatic ring, wherein at least one ring contains one or two of the moiety X;

C is a five- or six-membered aliphatic ring containing one to three of the moiety X, and optionally substituted with oxo;

R$^b$ and R$^c$, independently, are selected from the group consisting of hydro, OH, C$_{1-3}$alkyl, C$_{1-3}$alkyleneOH, and C$_{1-3}$alkyleneN(R$^e$)$_2$, or R$^b$ and R$^c$ are taken together to form a five-, six-, or seven-membered aliphatic ring optionally containing one or two of the moiety X;

R$^d$ is selected from the group consisting of C$_{1-4}$alkyl, C$_{2-6}$alkenyl, C$_{1-3}$alkyleneC$_{3-8}$heterocycloalkyl, OR$^e$, C$_{1-3}$alkyleneOR$^e$, N(R$^e$)$_2$, SR$^e$, halo, nitro, CRO, cyano, NC, C(=O)R$^e$, OC(=O)R$^e$, C(=0)OR$^e$, C(=O)N(R$^e$)$_2$, CH=NOH, CH=CHCH$_2$OH, N(R$^e$)COR$^e$, and C$_{1-3}$alkyleneN(R$^e$)$_2$, or two R$^d$ groups are taken together to form a five-, six-, or seven-membered aliphatic ring optionally containing one or two of the moiety X;

R$^e$ is selected from the group consisting of hydro, C$_{1-6}$alkyl, C$_{2-6}$alkenyl, aryl, heteroaryl, C$_{3-8}$cycloalkyl, THP, Ts, Boc, and C$_{3-8}$heterocycloalkyl;

q is 0 through 3;

or a pharmaceutically acceptable salt thereof.

12. A composition comprising a compound of claim 1 and a pharmaceutically acceptable diluent or carrier.

13. A method of treating a male or female mammal suffering from HIV or AIDS wherein inhibition of HIV-1 protease provides a therapeutic benefit comprising administering to said mammal a therapeutically effective amount of a compound of claim 1.

14. The method of claim 13 wherein the mammal is a human.

15. A method of treating a male or female mammal suffering from HIV or AIDS wherein inhibition of HIV-1 protease provides a therapeutic benefit comprising administering to said mammal an effective amount of a pharmaceutical composition comprising a compound of claim 1 and a pharmaceutically acceptable diluent or carrier.

16. A method of treating a male or female mammal suffering from where HIV or AIDS wherein inhibition of HIV-1 protease provides a therapeutic benefit comprising administering a therapeutically effective amount of (a) a compound of claim 1, and (b) a second therapeutically active ingredient effective against HIV or AIDS.

17. The method of claim 16 wherein (a) and (b) are administered simultaneously, separately, or sequentially.

18. The method of claim 16 wherein the second therapeutically active agent is selected from the group consisting of a second HIV protease inhibitor, an antiviral agent, an immunomodulator, a nucleoside analog, a tat antagonist, a glycosidase inhibitor, and mixtures thereof.

19. The method of claim 18 wherein the second therapeutically active ingredient is selected from the group consisting of Ro 31-859, KNI-272, AZT, DDI, DDC, 3TC, D4T, PMEA, Ro 5-3335, Ro 24-7429, indinavir, ritonavir, saquinavir, nelfinavir, amprenavir, abacavir, castanospermine, castanospermine 6-butryl ester, N-butyl-1-deoxynojirimycin, N-butyl-1-deoxynojirimycin per-butryl ester, 097, acemannan, acyclovir, AD-439, AD5-519, adefovir clipivoxil, AL-721, alpha interferon, ansamycin, beta-fluoro-ddA, BMS-232623, BMS-234475, CI-1012, cidofovir, delaviridine, EL-10, efaviren, famciclovir, FTC, hypericin, Compound Q, ISIS 2922, lobucavir, nevirapine, novapren, peptide T, octapeptide, PNU-140690, probacol, stavudine, valacicbovir, virazole, zalcitabine, ABT-378, bropirimine, gamma interferon, interleukin-2, TNF, etanercept, infliximab, fluconalzole, piritrexim, trimetrexate, daunorubicin, leukotriene B4 receptor antagonist, and analogs and prodrugs thereof.

* * * * *

UNITED STATES PATENT AND TRADEMARK OFFICE
CERTIFICATE OF CORRECTION

PATENT NO. : 7,157,489 B2 Page 1 of 1
APPLICATION NO. : 10/382435
DATED : January 2, 2007
INVENTOR(S) : Arun K. Ghosh et al.

It is certified that error appears in the above-identified patent and that said Letters Patent is hereby corrected as shown below:

In the Claims:

At Column 129, line 28, "seven-mernbered" should be -- seven-membered --.

At Column 129, line 31, "$C_{1-8}$cycloalkyl" should be -- $C_{3-8}$cycloalkyl --.

At Column 133, line 50, "six-mernbered" should be -- six-membered --.

At Column 133, line 62, "OC(O)R$^e$" should be -- OC(=O)R$^e$ --.

At Column 135, line 38, "CRO" should be -- CHO --.

At Column 135, line 39, "C(=0)OR$^e$" should be -- C(=O)OR$^e$ --.

At Column 136, line 17, "from where HIV" should be -- from HIV --.

At Column 136, line 33, "castanospremine" should be -- castanospermine --.

At Column 136, line 36, "AD5-519" should be -- AD-519 --.

At Column 136, line 35, "per-butryl" should be -- per-butyl --.

At Column 136, line 42, "valacicbovir" should be -- valaciclovir --.

Signed and Sealed this

Sixteenth Day of October, 2007

JON W. DUDAS
*Director of the United States Patent and Trademark Office*